(12) United States Patent
Kim et al.

(10) Patent No.: US 9,990,722 B2
(45) Date of Patent: Jun. 5, 2018

(54) ELECTRONIC DEVICE PROVIDING A BIOEFFECT IMAGE

(71) Applicant: Samsung Display Co., LTD., Giheung-Gu, Yongin, Gyeonggi (KR)

(72) Inventors: Il-Nam Kim, Hwaseong-si (KR); Hak-Sun Kim, Seoul (KR); Won-Sang Park, Yongin-si (KR); Jong-Sung Bae, Hwaseong-si (KR); Jong-In Baek, Suwon-si (KR)

(73) Assignee: SAMSUNG DISPLAY CO., LTD., Gyeonggi-Do (KR)

( * ) Notice: Subject to any disclaimer, the term of this patent is extended or adjusted under 35 U.S.C. 154(b) by 0 days. days.

(21) Appl. No.: 14/529,799

(22) Filed: Oct. 31, 2014

(65) Prior Publication Data
US 2015/0324981 A1 Nov. 12, 2015

(30) Foreign Application Priority Data
May 12, 2014 (KR) .................. 10-2014-0056614

(51) Int. Cl.
G09G 5/00 (2006.01)
G06T 7/00 (2017.01)
A61N 5/06 (2006.01)
G09G 3/20 (2006.01)
H04M 1/725 (2006.01)

(52) U.S. Cl.
CPC .......... *G06T 7/0014* (2013.01); *A61N 5/0618* (2013.01); *G09G 3/2003* (2013.01); *A61N 2005/0644* (2013.01); *G09G 2310/0235* (2013.01); *G09G 2340/06* (2013.01); *G09G 2380/08* (2013.01); *H04M 1/72544* (2013.01)

(58) Field of Classification Search
None
See application file for complete search history.

(56) References Cited

U.S. PATENT DOCUMENTS 5,644,363 A  7/1997  Mead
5,818,421 A  10/1998  Ogino et al.
(Continued)

FOREIGN PATENT DOCUMENTS

DE  102010001018 A1  7/2011
EP      2610736 A1  7/2013
(Continued)

OTHER PUBLICATIONS

Extended European Search Report for Application No. 14198471.6-1652/2945117 dated Dec. 4, 2015.
EyeLeo prevents eye strain. Page 1 of 1 [online]. [retrieved on Oct. 7, 2015]. Retrieved from the Internet: <URL: http://eyeleo.com/overview.
(Continued)

*Primary Examiner* — Xiao Wu
*Assistant Examiner* — Mohammad H Akhavannik
(74) *Attorney, Agent, or Firm* — Cantor Colburn LLP

(57) ABSTRACT

An electronic device includes a processor configured to control an operation of the electronic device, a memory device coupled to the processor, where the memory device is configured to operate as a main memory of the electronic device, and a display device coupled to the processor, where the display device is configured to display an original image based on first image data for the original image at a first frame, and to display a bioeffect image based on second image data for the bioeffect image at a second frame.

15 Claims, 44 Drawing Sheets

(56) References Cited

U.S. PATENT DOCUMENTS

| | | | |
|---|---|---|---|
| 2006/0189879 A1* | 8/2006 | Miyajima | A61B 5/1135 600/534 |
| 2011/0159814 A1 | 6/2011 | Mallinson et al. | |
| 2012/0050307 A1* | 3/2012 | Mahowald | H05B 37/0218 345/590 |
| 2012/0259392 A1* | 10/2012 | Feng | A61N 5/0618 607/88 |
| 2013/0060306 A1* | 3/2013 | Colbauch | A61N 5/0618 607/88 |
| 2013/0216204 A1* | 8/2013 | Kulakov | H04N 7/163 386/278 |
| 2013/0296976 A1 | 11/2013 | Maxik et al. | |
| 2013/0314424 A1 | 11/2013 | Huang et al. | |
| 2015/0070337 A1* | 3/2015 | Bell | G09G 3/2003 345/207 |
| 2015/0255021 A1* | 9/2015 | Wu | G09G 3/3426 345/83 |

FOREIGN PATENT DOCUMENTS

| | | |
|---|---|---|
| JP | 1993244530 A | 9/1993 |
| JP | 08242411 | 9/1996 |
| JP | 2000339438 A | 12/2000 |
| JP | 2005165563 A | 6/2005 |
| JP | 2013153297 A | 8/2013 |
| KR | 1020090002306 A | 1/2009 |
| KR | 1020120087736 A | 8/2012 |
| KR | 1020120124256 A | 11/2012 |
| WO | 2007116341 A1 | 10/2007 |
| WO | 2008137489 A1 | 11/2008 |
| WO | 2012039695 A1 | 3/2012 |

OTHER PUBLICATIONS

Chinese Office Action for Application No. 201510038262.1 dated Apr. 16, 2018.

* cited by examiner

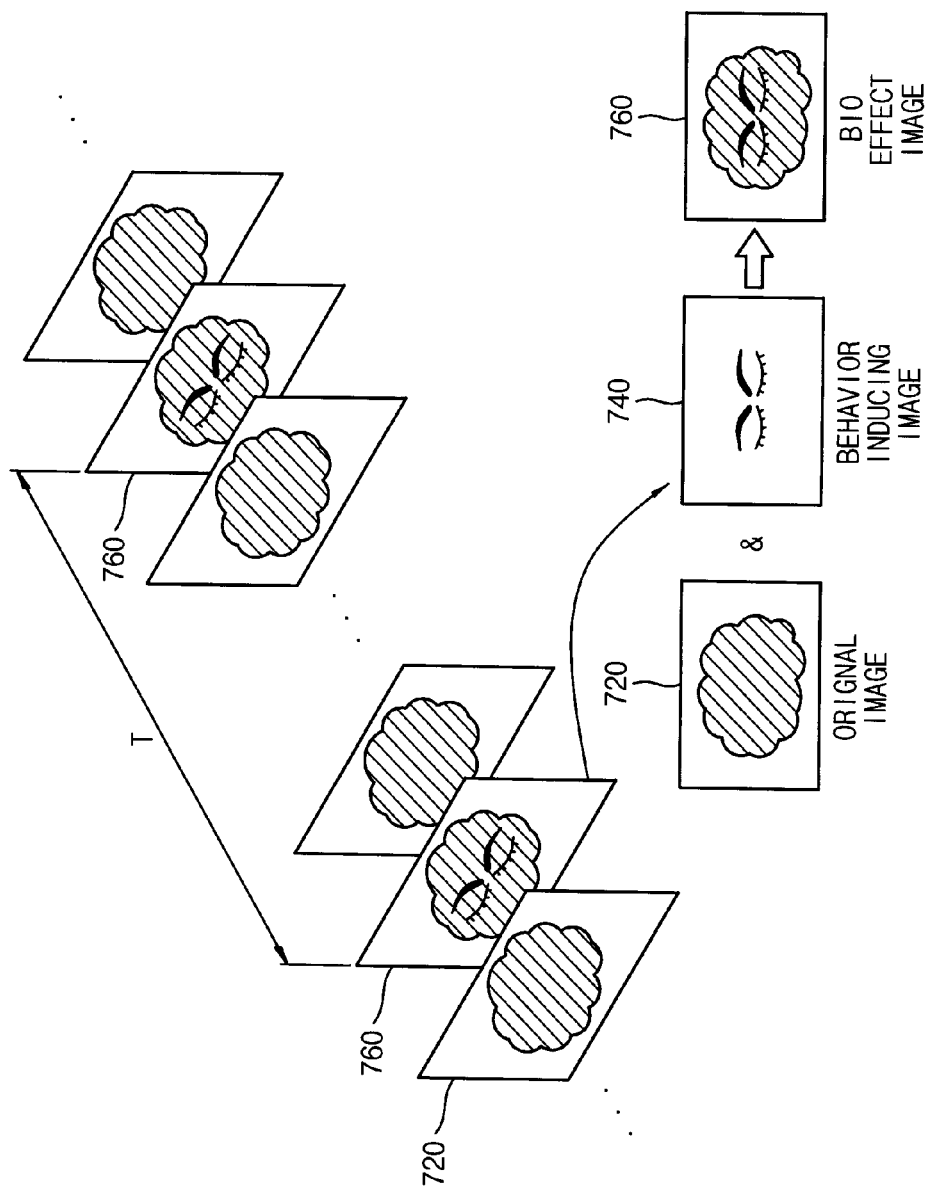

FIG. 16A
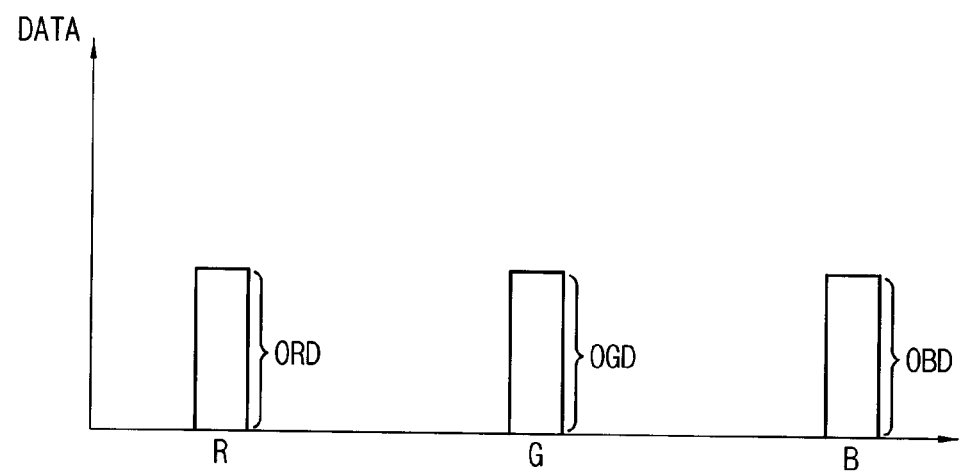
MODULATION
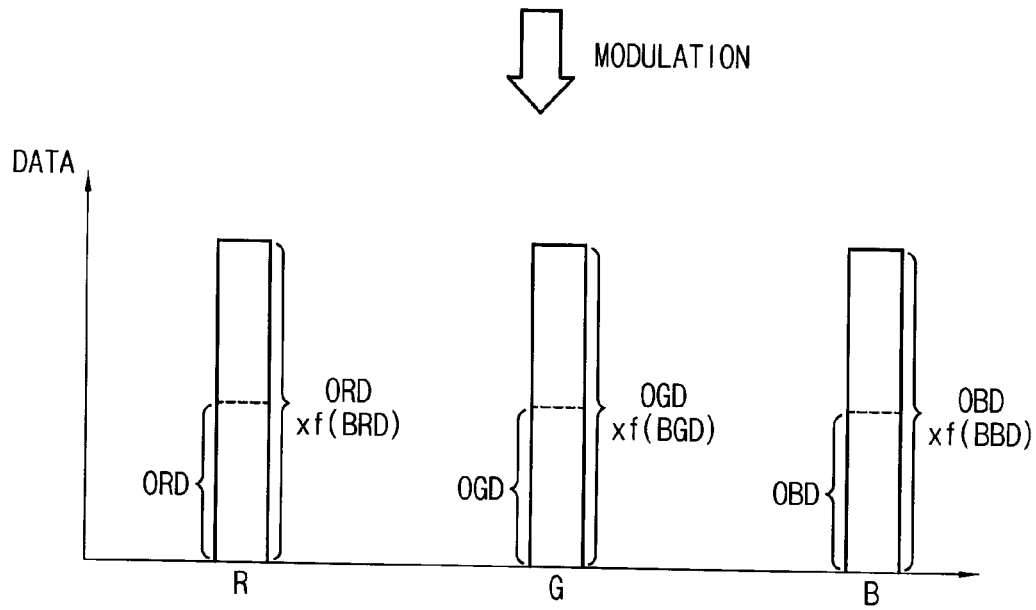

FIG. 16B
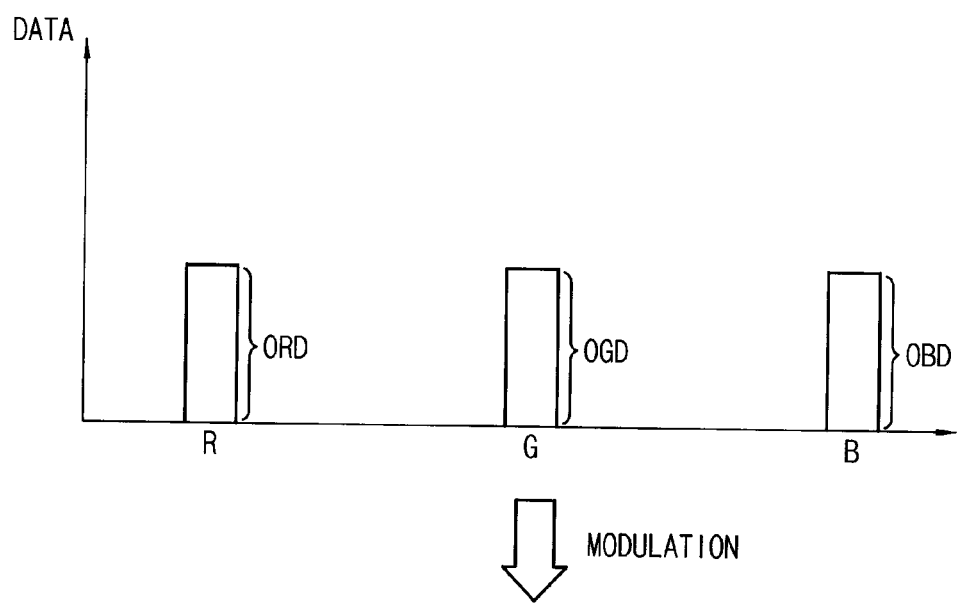
MODULATION
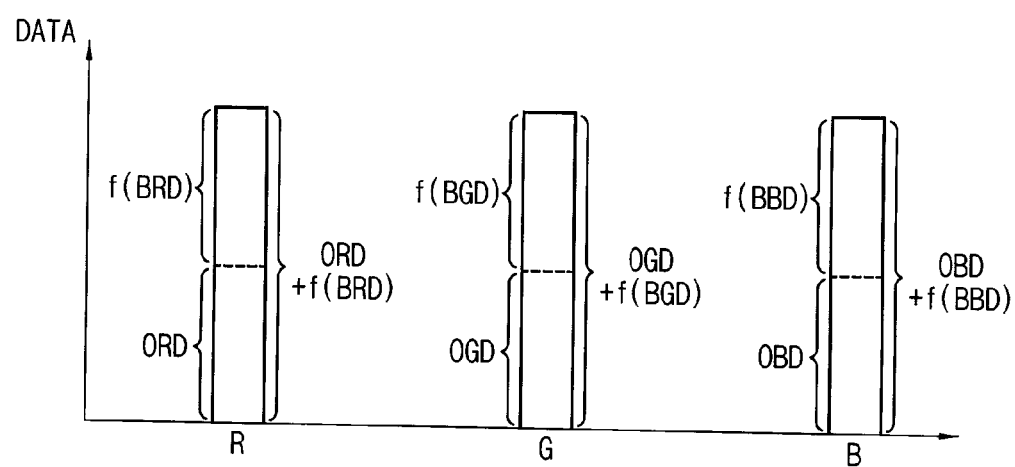

FIG. 18A
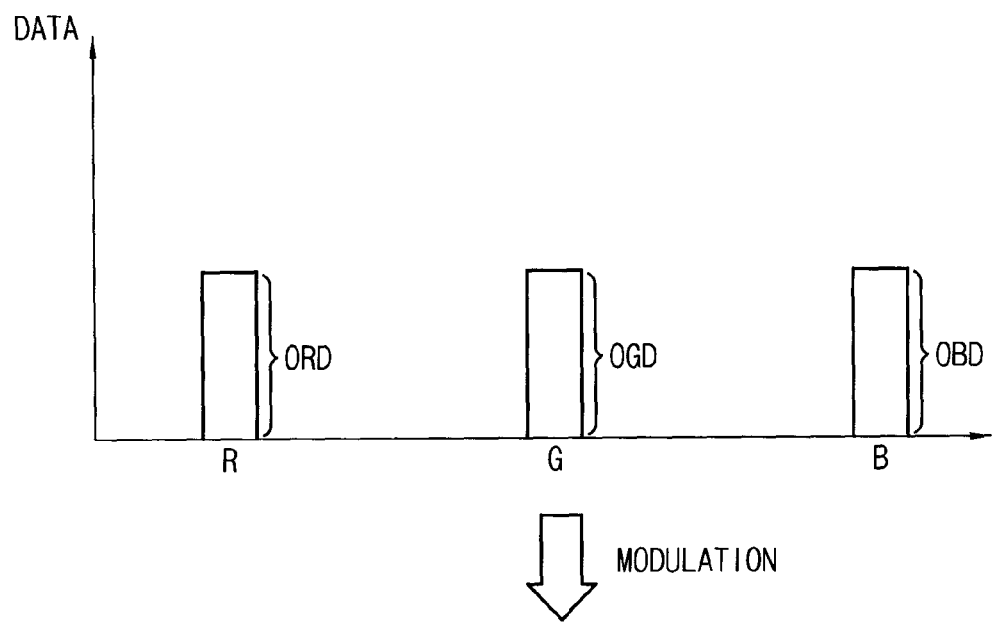
MODULATION
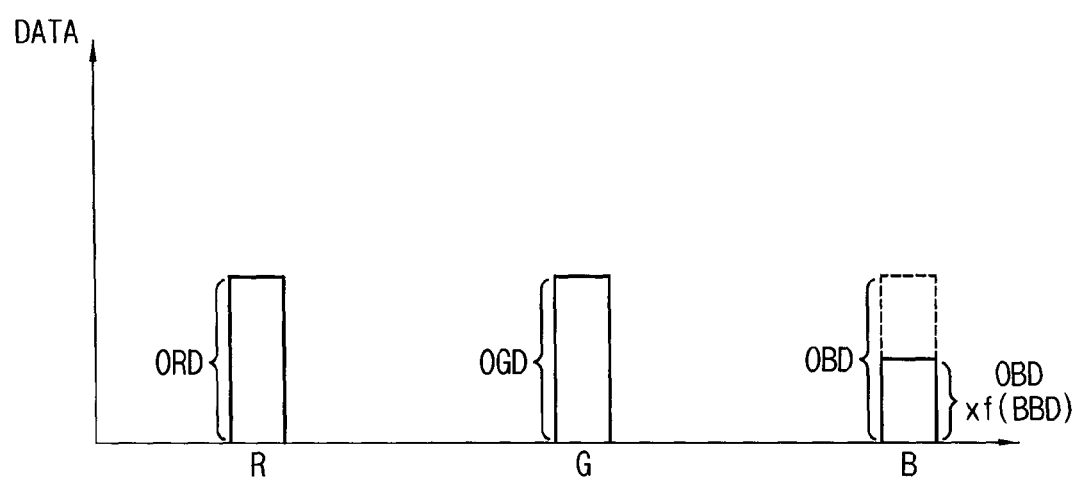

FIG. 18B
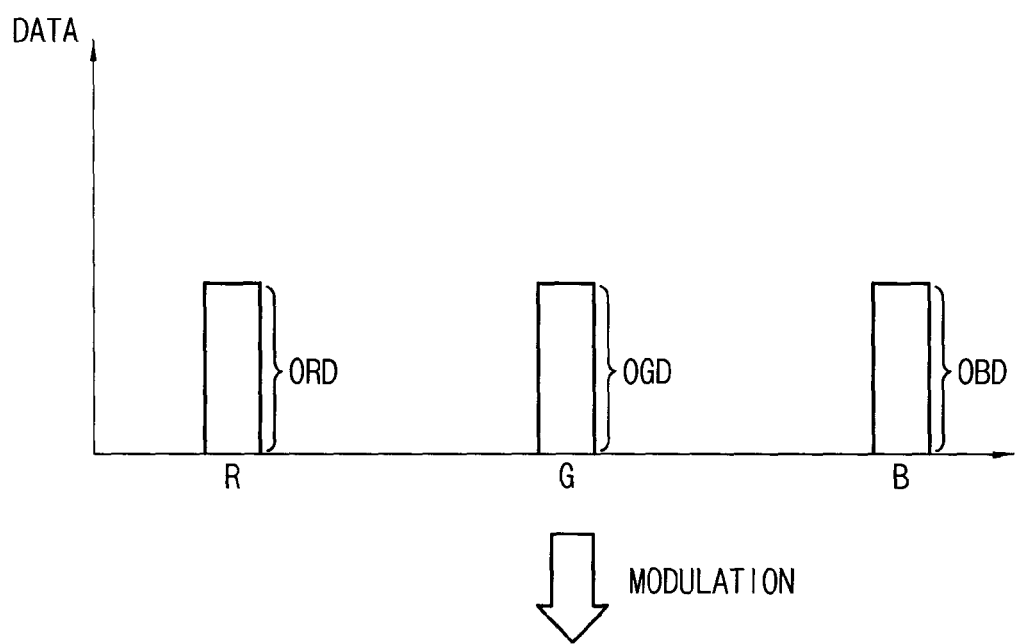
MODULATION
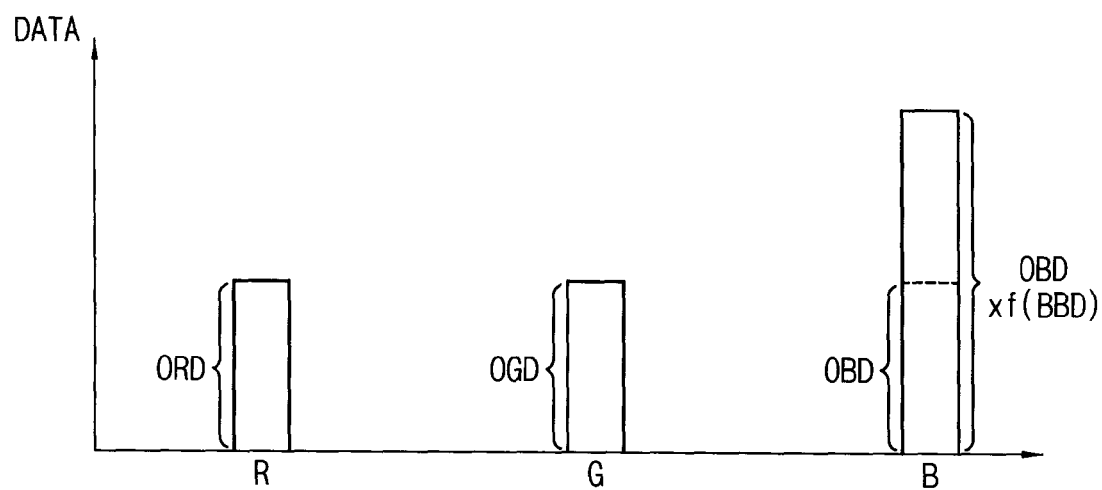

FIG. 21A
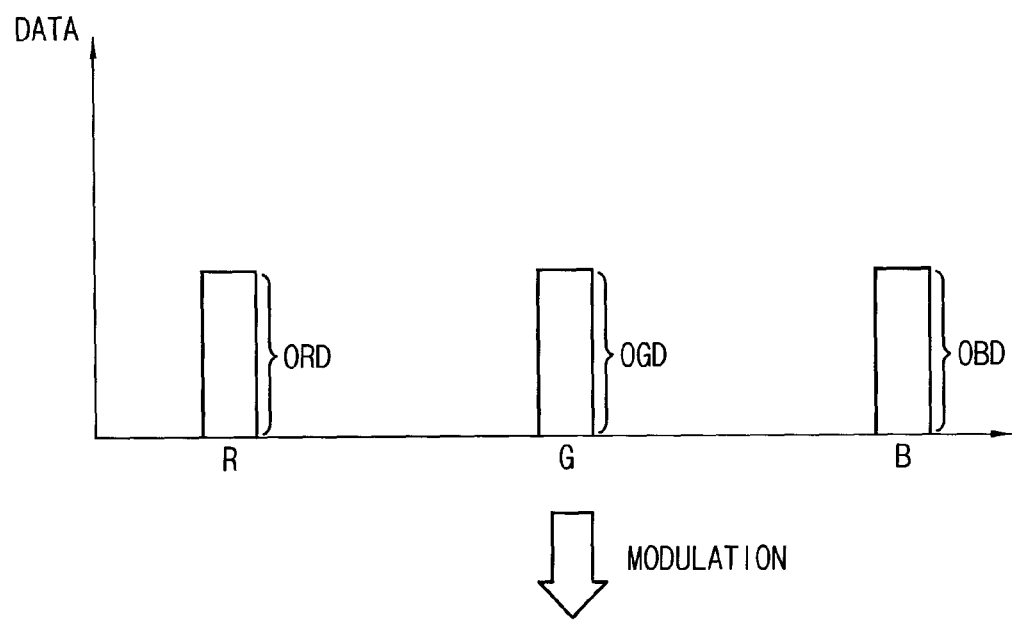
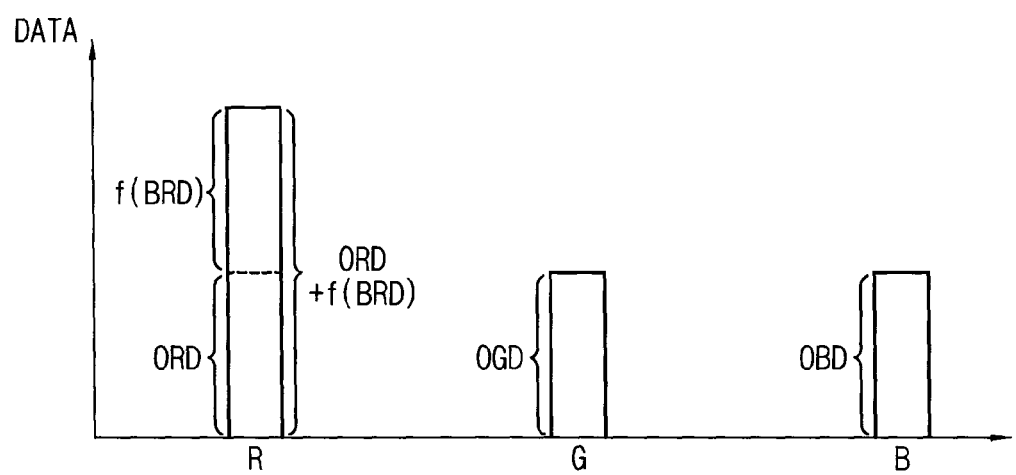

FIG. 21B
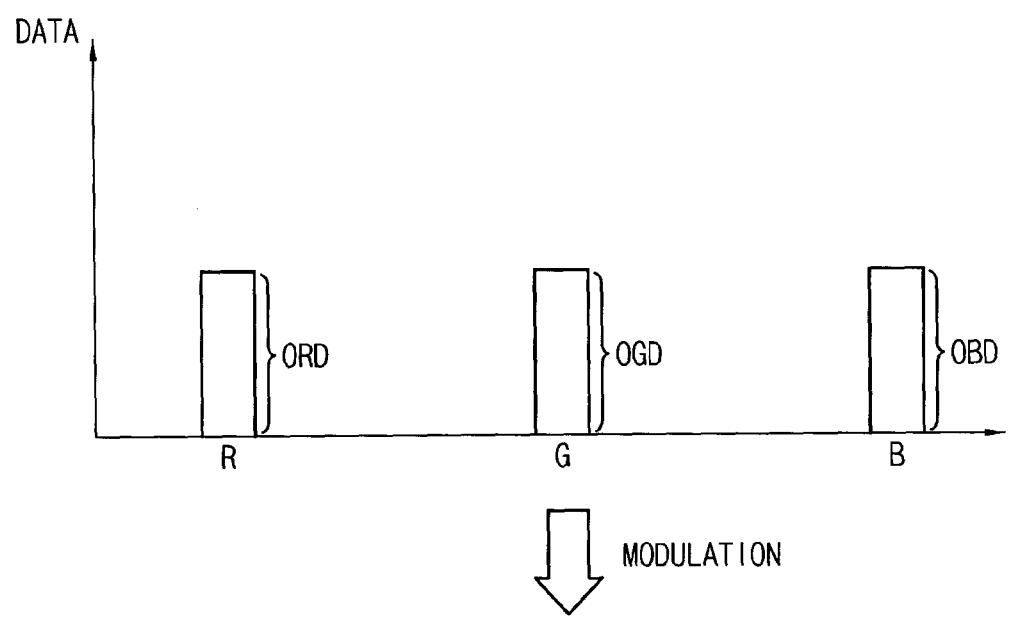
MODULATION
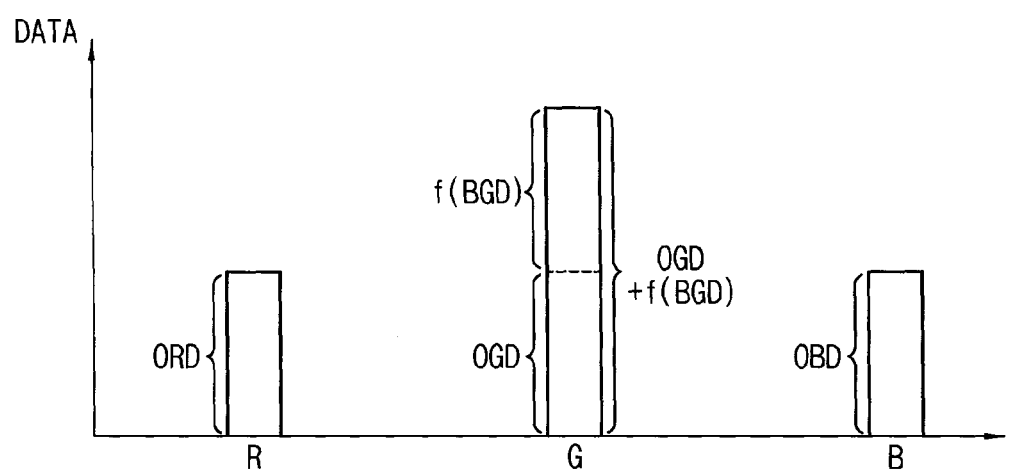

ELECTRONIC DEVICE PROVIDING A BIOEFFECT IMAGE

This application claims priority to Korean Patent Application No. 10-2014-0056614 filed on May 12, 2014, and all the benefits accruing therefrom under 35 U.S.C. § 119, the content of which in its entirety is herein incorporated by reference.

BACKGROUND

1. Technical Field

Exemplary embodiments of the invention relate to an electronic device. More particularly, exemplary embodiments of the invention relate to an electronic device that provides bioeffect images.

2. Description of the Related Art

Recently, a bioeffect device, such as a photo-therapy device, that radiates light to a human body has been developed. The bioeffect device may be used to provide bioeffect, such as skin care, biorhythm control or depression treatment, for example. However, a conventional bioeffect device is typically configured for only one particular type of treatment (such as anti-inflammatory therapy, pimple therapy, wrinkle therapy, skin lightening therapy, biorhythm control, or depression therapy). As a result, a user may require different bioeffect devices for different treatments. Furthermore, such a conventional bioeffect device may not be configured to display other images (such as visual images) while the user is undergoing photo-therapy.

SUMMARY

Exemplary embodiments relate to an electronic device that provides a bioeffect image.

According to exemplary embodiments, an electronic device includes a processor configured to control an operation of the electronic device, a memory device coupled to the processor, where the memory device is configured to operate as a main memory of the electronic device, and a display device coupled to the processor, where the display device is configured to display an original image based on first image data for the original image at a first frame, and to display a bioeffect image based on second image data for the bioeffect image at a second frame.

In some exemplary embodiments, the processor may include a graphic processing unit configured to control the display device, and the graphic processing unit may include a memory unit configured to store the second image data for the bioeffect image, and an image processing unit configured to provide the display device with the first image data at the first frame, and to provide the display device with the second image data stored in the memory unit at the second frame.

In some exemplary embodiments, the processor may include a graphic processing unit configured to control the display device, and the graphic processing unit may include an image processing unit configured to provide the display device with the first image data at the first frame, to generate the second image data by modulating the first image data, and to provide the display device with the generated second image data at the second frame.

In some exemplary embodiments, the electronic device may further include a graphic card coupled between the processor and the display device, where the graphic card is configured to control the display device, and the graphic card may include a memory unit configured to store the second image data for the bioeffect image, and an image processing unit configured to provide the display device with the first image data at the first frame, and to provide the display device with the second image data stored in the memory unit at the second frame.

In some exemplary embodiments, the electronic device may further include a graphic card coupled between the processor and the display device, where the graphic card is configured to control the display device, and the graphic card may include an image processing unit configured to provide the display device with the first image data at the first frame, to generate the second image data by modulating the first image data, and to provide the display device with the generated second image data at the second frame.

In some exemplary embodiments, the memory device may store the second image data for the bioeffect image, and an image processing code, and the image processing code may be executed by the processor to provide the display device with the first image data at the first frame, and to provide the display device with the second image data stored in the memory device at the second frame.

In some exemplary embodiments, the memory device may store an image processing code, and the image processing code may be executed by the processor to provide the display device with the first image data at the first frame, to generate the second image data by modulating the first image data, and to provide the display device with the generated second image data at the second frame.

In some exemplary embodiments, the display device may include a display panel, and an internal memory disposed on the display panel, and configured to store the second image data for the bioeffect image and an image processing code, and the image processing code stored in the internal memory of the display device may be executed by the processor to provide the display panel with the first image data at the first frame, and to provide the display panel with the second image data stored in the internal memory at the second frame.

In some exemplary embodiments, the display device may include a display panel, and a display driver configured to receive the first image data for the original image, to drive the display panel based on the first image data to display the original image at the first frame, and to drive the display panel based on the second image data to display the bioeffect image at the second frame.

In some exemplary embodiments, the display driver may include a memory unit configured to store the second image data for the bioeffect image, an image processing unit configured to receive the first image data, to output the first image data at the first frame, and to output the second image data stored in the memory unit at the second frame, and a driving unit configured to drive the display panel based on the first image data output from the image processing unit at the first frame, and to drive the display panel based on the second image data output from the image processing unit at the second frame.

In some exemplary embodiments, the memory unit may store image data for a behavior inducing image as the second image data for the bioeffect image, the image processing unit may provide the driving unit with the image data for the behavior inducing image stored in the memory unit at the second frame, and the driving unit may drive the display panel based on the image data for the behavior inducing image to display the behavior inducing image as the bioeffect image at the second frame.

In some exemplary embodiments, the behavior inducing image may be a blinking inducing image which induces a user to blink eyes of the user.

In some exemplary embodiments, the behavior inducing image may be displayed for a predetermined duration shorter than a duration perceptible by a user.

In some exemplary embodiments, the memory unit may store image data for a photo-therapy image as the second image data for the bioeffect image, the image processing unit may provide the driving unit with the image data for the photo-therapy image stored in the memory unit at the second frame, and the driving unit may drive the display panel based on the image data for the photo-therapy image to display the photo-therapy image as the bioeffect image at the second frame.

In some exemplary embodiments, the display driver may include an image processing unit configured to receive the first image data, to output the first image data at the first frame, to generate the second image data by modulating the first image data, and to output the second image data at the second frame, and a driving unit configured to drive the display panel based on the first image data output from the image processing unit at the first frame, and to drive the display panel based on the second image data output from the image processing unit at the second frame.

In some exemplary embodiments, the display driver may further include a memory unit configured to store image data for a behavior inducing image, the image processing unit may generate the second image data by synthesizing the first image data and the image data for the behavior inducing image at the second frame, and the driving unit may drive the display panel based on the second image data where the first image data and the image data for the behavior inducing image are synthesized to display, as the bioeffect image, an image where the original image and the behavior inducing image are synthesized at the second frame.

In some exemplary embodiments, the image where the original image and the behavior inducing image are synthesized may be displayed for a predetermined duration shorter than a duration that is perceptible by a user.

In some exemplary embodiments, the image processing unit may generate the second image data by adjusting at least one of red sub-pixel data, green sub-pixel data and blue sub-pixel data included in the first image data at the second frame, and the driving unit may drive the display panel based on the second image data where the at least one of the red sub-pixel data, the green sub-pixel data and the blue sub-pixel data is adjusted to display, as the bioeffect image, an image where at least one of red luminance, green luminance and blue luminance is adjusted from the original image at the second frame.

In some exemplary embodiments, the image processing unit may generate the second image data by decreasing the blue sub-pixel data from the first image data at the second frame, and the driving unit may drive the display panel based on the second image data where the blue sub-pixel data is decreased to display, as the bioeffect image, a biorhythm control image where the blue luminance is decreased from the original image to prevent suppression of melatonin secretion of a user at the second frame.

In some exemplary embodiments, the image processing unit may generate the second image data by increasing the blue sub-pixel data from the first image data at the second frame, and the driving unit may drive the display panel based on the second image data where the blue sub-pixel data is increased to display, as the bioeffect image, a biorhythm control image where the blue luminance is increased from the original image to suppress melatonin secretion of a user at the second frame.

In some exemplary embodiments, the image processing unit may generate the second image data by increasing the red sub-pixel data from the first image data at the second frame, and the driving unit may drive the display panel based on the second image data where the red sub-pixel data is increased to display, as the bioeffect image, a color weakness compensation image where the red luminance is increased from the original image to increase a visibility of a user having red color weakness at the second frame.

In some exemplary embodiments, the image processing unit may generate the second image data by increasing the green sub-pixel data from the first image data at the second frame, and the driving unit may drive the display panel based on the second image data where the green sub-pixel data is increased to display, as the bioeffect image, a color weakness compensation image where the green luminance is increased from the original image to increase a visibility of a user having green color weakness at the second frame.

In some exemplary embodiments, the image processing unit may generate the second image data by increasing the at least one of the red sub-pixel data, the green sub-pixel data and the blue sub-pixel data from the first image data at the second frame, and the driving unit may drive the display panel based on the second image data where the at least one of the red sub-pixel data, the green sub-pixel data and the blue sub-pixel data is increased to display, as the bioeffect image, a photo-therapy image where the at least one of the red luminance, the green luminance and the blue luminance is increased from the original image at the second frame.

In some exemplary embodiments, the image processing unit may generate third image data by decreasing the at least one of the red sub-pixel data, the green sub-pixel data and the blue sub-pixel data from the first image data at a third frame adjacent to the second frame, the driving unit may drive the display panel based on the third image data where the at least one of the red sub-pixel data, the green sub-pixel data and the blue sub-pixel data is decreased to display a compensating image where the at least one of the red luminance, the green luminance and the blue luminance is decreased from the original image at the third frame, and the original image may be perceived based on the photo-therapy image displayed at the second frame and the compensating image displayed at the third frame.

In some exemplary embodiments, the electronic device may further include a sensor configured to sense incident light.

In some exemplary embodiments, the sensor may measure chromaticity of the incident light, and, when the measured chromaticity of the incident light indicates a yellow color, the display device may display, as the bioeffect image, a biorhythm control image which prevents suppression of melatonin secretion of a user.

In some exemplary embodiments, the sensor may detect an eye blink of a user, and, if the user does not blink during a predetermined time, the display device may display a blinking inducing image as the bioeffect image.

In some exemplary embodiments, the sensor may sense infrared light as the incident light, and the electronic device may initiate or terminate a bioeffect mode in response to the infrared light.

In some exemplary embodiments, the sensor may be disposed at at least one of an active region of a display panel included in the display device, a peripheral region of the display panel, a printed circuit board coupled to the display panel, and an outside of the display device.

According to exemplary embodiments, there is provided an electronic device including a display device configured to display a bioeffect image where an original image and a predetermined image are synthesized at a first frame, and to display a compensating image where the original image and a complementary image, which is complementary to the predetermined image, are synthesized, at a second frame, and shutter glasses configured to be open at the first frame, and to be closed at the second frame.

In some exemplary embodiments, the bioeffect image may be provided to a first user who wears the shutter glasses at the first frame, and no image may be provided to the first user at the second frame.

In some exemplary embodiments, the bioeffect image may be provided to a second user who does not wear the shutter glasses at the first frame, and the compensating image is provided to the second user at the second frame, and the original image may be perceived by the second user based on the bioeffect image provided at the first frame and the compensating image provided at the second frame.

In some exemplary embodiments, the predetermined image may be a behavior inducing image, a color weakness compensation image, a biorhythm control image or a photo-therapy image.

According to exemplary embodiments, an electronic device includes a display device configured to display an original image at a first frame, and to display a bioeffect image at a second frame, first shutter glasses configured to be open at the first frame, and to be closed at the second frame, and second shutter glasses configured to be closed at the first frame, and to be open at the second frame.

BRIEF DESCRIPTION OF THE DRAWINGS

The above and other features of the invention will become more apparent by describing in detailed exemplary embodiments thereof with reference to the accompanying drawings, in which:

FIG. 15 is a diagram illustrating an exemplary embodiment of image frames displayed by the method of FIG. 14;

FIGS. 16A through 16C are diagrams for describing exemplary embodiments of modulation operations performed by the method of FIG. 14;

FIGS. 18A and 18B are diagrams for describing exemplary embodiments of a modulation operation performed by the method of FIG. 17;

FIGS. 21A through 21C are diagrams for describing exemplary embodiments of a modulation operation performed by the method of FIG. 20;

DESCRIPTION OF EMBODIMENTS

Figure 1:
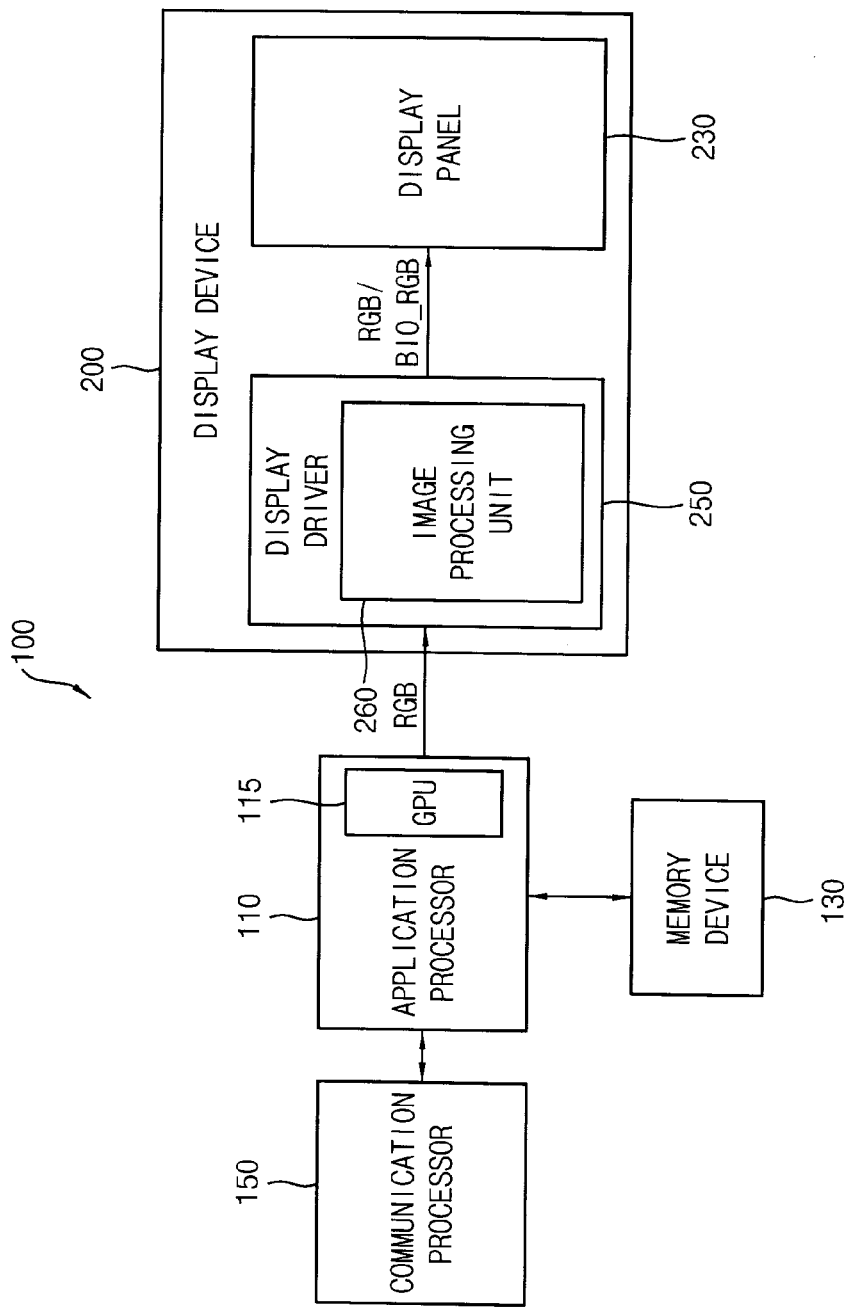
FIG. 1 is a block diagram illustrating an exemplary embodiment of a mobile device including a display device having a bioeffect image providing function, in accordance with the invention.

The invention now will be described more fully hereinafter with reference to the accompanying drawings, in which various embodiments are shown. This invention may, however, be embodied in many different forms, and should not be construed as limited to the embodiments set forth herein. Rather, these embodiments are provided so that this disclosure will be thorough and complete, and will fully convey the scope of the invention to those skilled in the art. Like reference numerals refer to like elements throughout.

It will be understood that when an element is referred to as being "on" another element, it can be directly on the other element or intervening elements may be therebetween. In contrast, when an element is referred to as being "directly on" another element, there are no intervening elements present.

It will be understood that, although the terms "first," "second," "third" etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this disclosure belongs. It will be further understood that terms, such as those defined in commonly used dictionaries, should be interpreted as having a meaning that is consistent with their meaning in the context of the relevant art and the disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the claims.

Hereinafter, exemplary embodiments of the invention will be described in detail with reference to the accompanying drawings.

FIG. 1 is a block diagram illustrating an exemplary embodiment of a mobile device including a display device having a bioeffect image providing function, in accordance with exemplary embodiments.

Referring to FIG. 1, an exemplary embodiment of a mobile device 100 includes an application processor 110, a memory device 130, a communication processor 150 and a display device 200. According to an exemplary embodiment, the mobile device 100 may be any mobile device, such as a cellular phone, a smart phone, a tablet computer, a personal digital assistant ("PDA"), a portable multimedia player ("PMP"), a digital camera, a music player, a portable game console, a navigation system or a video phone, for example.

The application processor 110 controls an operation of the mobile device 100. In one exemplary embodiment, for example, the application processor 110 may execute an operating system ("OS") and various applications, such as an internet browser, a game application or a video player, for example, to control the operation of the mobile device 100. The application processor 110 may include a graphic processing unit ("GPU") 115 that controls the display device 200. The GPU 115 may provide the display device 200 with first image data RGB for an original image, that is, image data with which the original image is displayed, and control signals (e.g., a vertical synchronization signal, a horizontal synchronization signal, a data enable signal, a clock signal, etc.) for controlling the display device 200.

The communication processor 150 may perform wired or wireless communication with an external device. In one exemplary embodiment, for example, the communication processor 150 may perform an Ethernet communication, near field communication ("NFC"), radio frequency identification ("RFID") communication, mobile telecommunication, memory card communication, universal serial bus ("USB") communication, wireless internet, wireless fidelity ("Wi-Fi"), global positioning system ("GPS"), Bluetooth® ("BT"), etc. The communication processor 150 may comprise a baseband chipset and may support global system for mobile communication ("GSM"), general packet radio system ("GPRS"), wideband code division multiple access ("WCDMA"), or high speed uplink/downlink packet access ("HSxPA"), for example. In some exemplary embodiments, the application processor 110 and the communication processor 150 may be implemented as a single chip. In other exemplary embodiments, the application processor 110 and the communication processor 150 may be implemented as separate chips.

The memory device 130 may be coupled to the application processor 110, and may operate as a main memory. In one exemplary embodiment, for example, the memory device 130 may store data processed by the application processor 110, may store data transferred by the communication processor 150, or may serve as a working memory. In one exemplary embodiment, for example, the memory device 130 may be a volatile memory device, such as a dynamic random access memory ("DRAM"), a static random access memory ("SRAM"), a mobile DRAM, a double data rate ("DDR") synchronous DRAM ("SDRAM"), a low power DDR ("LPDDR") SDRAM, or a graphic DDR ("GDDR") SDRAM. Alternatively, the memory device 130 may be a nonvolatile memory device, such as an electrically erasable programmable read-only memory ("EEPROM"), a flash memory, a phase change random access memory ("PRAM"), a resistance random access memory ("RRAM"), a nano floating gate memory ("NFGM"), a polymer random access memory ("PoRAM"), a magnetic random access memory ("MRAM"), or a ferroelectric random access memory ("FRAM"), etc.

The display device 200 may be coupled to the application processor 110, and may display an image based on the image data RGB provided by the GPU 115 in the application processor 110. The display device 200 may include a display panel 230 that displays an image, and a display driver 250 that drives the display panel 230. According to exemplary embodiments, the display panel 230 may be any type of display panel, such as an organic light emitting display ("OLED") panel, a liquid crystal display ("LCD") panel or a plasma display panel ("PDP"), for example.

The display driver 250 may receive the first image data RGB for the original image from the GPU 115, and may drive the display panel 230 based on the first image data RGB to display the original image corresponding to the first image data RGB. In some exemplary embodiments, the display driver 250 may be implemented as a single chip. At a predetermined frame, the display driver 250 may drive the display panel 230 based on second image data BIO_RGB for a bioeffect image instead of the first image data RGB to display the bioeffect image instead of the original image. In some exemplary embodiments, the bioeffect image may be inserted between frames of the original image. In other exemplary embodiments, the bioeffect image may be generated by modulating the original image (e.g., by synthesizing the original image with a predetermined image or by adjusting at least one of red luminance, green luminance and blue luminance of the original image).

In some exemplary embodiments, the bioeffect image may be a behavior inducing image for inducing a predetermined behavior of a user or a viewer. In one exemplary embodiment, for example, the bioeffect image may be a blinking inducing image that induces a user to blink eyes of the user. In other exemplary embodiments, the bioeffect image may be a biorhythm control image generated by adjusting predetermined sub-pixel data (e.g., blue sub-pixel data) to increase or decrease melatonin secretion of a user. In still other exemplary embodiments, the bioeffect image may be a color weakness compensation image where luminance of a particular color (e.g., red luminance or green luminance) is increased to enhance a visibility of a user having color weakness. In still other exemplary embodiments, the bioeffect image may be photo-therapy image for providing anti-inflammatory therapy, pimple therapy, wrinkle therapy, skin lightening therapy, depression therapy, sterilization therapy, etc.

As described above, an exemplary embodiment of the display driver 250 according to the invention may have a bioeffect image providing function. The display driver 250 may include an image processing unit 260 (e.g., an image processor) for performing the bioeffect image providing function.

The image processing unit 260 may receive the first image data RGB for the original image from the GPU 115, may output the first image data RGB as it is at a first frame, and may output the second image data BIO_RGB for the bioeffect image instead of the first image data RGB at a second frame.

In some exemplary embodiments, the display driver 250 may further include a memory unit (e.g., an additional memory device) that stores the second image data BIO_RGB for the bioeffect image, and the image processing unit 260 may output the second image data BIO_RGB stored in the memory unit instead of the first image data RGB at the second frame. The display driver 250 may further include a driving unit or a driver that drives the display panel 230 based on the first image data RGB output from the image processing unit 260 at the first frame, and drives the display panel 230 based on the second image data BIO_RGB output from the image processing unit 260 at the second frame. In some exemplary embodiments, the second image data BIO_RGB stored in the memory included in the display driver 250 may be binary image data having a value of '0' or '1' for each pixel. In other exemplary embodiments, the second image data BIO_RGB may have two or more bits for each pixel. In an exemplary embodiment, where the second image data BIO_RGB is the binary image data, the memory unit may have a small size, and thus the display driver 250 may have a small size. In some exemplary embodiments, the second image data BIO_RGB stored in the memory unit may have a size corresponding to the entire frame. In other exemplary embodiments, the second image data BIO_RGB may have a size corresponding to a portion of a frame. In such embodiments, the memory unit may have a small size, and thus the display driver 250 may have a small size.

In other exemplary embodiments, the image processing unit 260 may generate the second image data BIO_RGB by modulating the first image data RGB, and may output the generated second image data BIO_RGB to the driving unit at the second frame. In some exemplary embodiments, the image processing unit 260 may synthesize the first image data RGB and image data for a predetermined image (e.g., a behavior inducing image, a biorhythm control image, a color weakness compensation image, a photo-therapy image, etc.) to generate the bioeffect image where the original image is overlaid with the predetermined image. In one exemplary embodiment, for example, the bioeffect image where the original image is overlaid with the predetermined image may be generated by adding the image data for the predetermined image to the first image data RGB with a predetermined ratio or by multiplying the image data for the predetermined image and the first image data RGB with a predetermined ratio. In other exemplary embodiments, the image processing unit 260 may generate the second image data BIO_RGB by increasing or decreasing at least one of red sub-pixel data, green sub-pixel data and blue sub-pixel data included in the first image data RGB. In still other exemplary embodiments, the memory unit included in the display driver 250 may store information about a modulation operation performed by the image processing unit 260, and the image processing unit 260 may perform the modulation operation based on the information stored in the memory unit. In one exemplary embodiment, for example, the information stored in the memory unit may include positions of modulated data in a frame, values of data to be added or multiplied, indication of which one of the red, green and blue sub-pixel data are modulated, coefficients of the modulation operation, etc.

In an exemplary embodiment, as described above, the image processing unit 260 may output the second image data BIO_RGB for the bioeffect image instead of the received first image data RGB at one or more second frames per a predetermined number of frames, and the display driver 250 may drive the display panel 230 based on the second image data BIO_RGB to display the bioeffect image. Accordingly, in such an embodiment, the bioeffect image, such as the behavior inducing image, the photo-therapy image, the color weakness compensation image or the biorhythm control image, for example, may be provided to a user.

In some exemplary embodiments, the display device 200 may periodically display the bioeffect image. In such embodiments, the image processing unit 260 may output the second image data BIO_RGB for the bioeffect image at one or more second frames per a predetermined number of frames corresponding to a predetermined period. In one exemplary embodiment, for example, the image processing unit 260 may output the second image data BIO_RGB for the bioeffect image at one frame per second. Thus, in an exemplary embodiment of the display device 200 that operates at about 120 hertz (Hz), the bioeffect image may be displayed at one frame per 120 frames. In other exemplary embodiments, time intervals between frames at which the bioeffect images are displayed may not be fixed. In still other exemplary embodiments, the bioeffect image may be displayed at every frame.

In some exemplary embodiments, the display driver 250 may drive the display panel 230 to display the bioeffect image for a predetermined duration shorter than a duration that is perceptible by a user. In such embodiments, the display driver 250 may perform a subliminal driving operation. In one exemplary embodiment, for example, the display driver 250 may allow a user not to consciously perceive the bioeffect image by driving the display panel 230 to display the bioeffect image at a predetermined number or less of consecutive frames (e.g., 4 or less frames in case of 120 Hz driving) with a period longer than a predetermined time. Accordingly, exemplary embodiments of the mobile device 100 and the display device 200 including the display driver 250, according to the invention, may provide the bioeffect image without causing any inconvenience of the user.

In some exemplary embodiments, the display driver 250 may drive the display panel 230 to display the bioeffect image where the original image and a predetermined image (e.g., a behavior inducing image, a biorhythm control image, a color weakness compensation image, a photo-therapy image, etc.) are synthesized at odd-numbered frames, and may drive the display panel 230 to display a compensating image where the original image and a complementary image that is complementary to the predetermined image are synthesized at even-numbered frames. In one exemplary embodiment, for example, the display driver 250 may generate the bioeffect image by performing a modulation operation that increases red sub-pixel data of the first image data RGB for the original image at the odd-numbered frame, and may generate the compensating image by performing a modulation operation that decreases the red sub-pixel data of the first image data RGB for the original image at the even-numbered frame. Thus, the bioeffect image is provided to a user at the odd-numbered frame, and the compensating image is provided to the user at the even-numbered frame. Accordingly, in such embodiments, where the bioeffect image and the compensating image are alternately provided to the user, the user may perceive the original image based on the alternately provided bioeffect and compensating images while the effect by the bioeffect image (e.g., behavior inducing, photo-therapy, biorhythm control, etc.) is provided to the user. Therefore, such embodiments of the mobile device 100 and the display device 200 including the display driver 250 may provide the bioeffect image without causing any inconvenience of the user.

As described above, in an exemplary embodiment, the display driver 250 may drive the display panel 230 based on the second image data BIO_RGB for the bioeffect image instead of the first image data RGB for the original image at one or more frames per a predetermined number of frames. Accordingly, exemplary embodiments of the display device 200 and the mobile device 100 may provide the bioeffect image using the display driver 250 having the bioeffect image providing function. In some exemplary embodiments, the mobile device 100 and the display device 200 including the display driver 250 may provide the bioeffect image without causing any inconvenience of the user by displaying the bioeffect image for a short duration such that the bioeffect image is not consciously perceived by the user. In such embodiments, the display driver 250 may have the bioeffect image providing function in itself without data processing of an external device, and thus power consumption and a data processing amount of the mobile device 100 for providing the bioeffect image may be reduced. In such embodiment, the display driver 250, the display device 200 and the mobile device 100 may provide the bioeffect image while displaying the original image, and thus the user may be affected by the bioeffect image without sparing time only for the bioeffect.

In some exemplary embodiments, the mobile device 100 may further include an input device, such as a keypad or a touch screen, for example, and an output device, such as speaker, for example. In some exemplary embodiments, the mobile device 100 may further include a power supply for supplying the mobile device 100 with power, a camera image processor ("CIS"), etc.

In some exemplary embodiments, the mobile device 100 or components of the mobile device 100 may be packaged in various forms, such as package on package ("PoP"), ball grid arrays ("BGA"s), chip scale packages ("CSP" s), plastic leaded chip carrier ("PLCC"), plastic dual in-line package ("PDIP"), die in waffle pack, die in wafer form, chip on board ("COB"), ceramic dual in-line package ("CERDIP"), plastic metric quad flat pack ("MQFP"), thin quad flat pack ("TQFP"), small outline integrated circuit ("SOIC"), shrink small outline package ("SSOP"), thin small outline package ("TSOP"), system in package ("SIP"), multi chip package ("MCP"), wafer-level fabricated package ("WFP"), or wafer-level processed stack package ("WSP").

Figure 2:
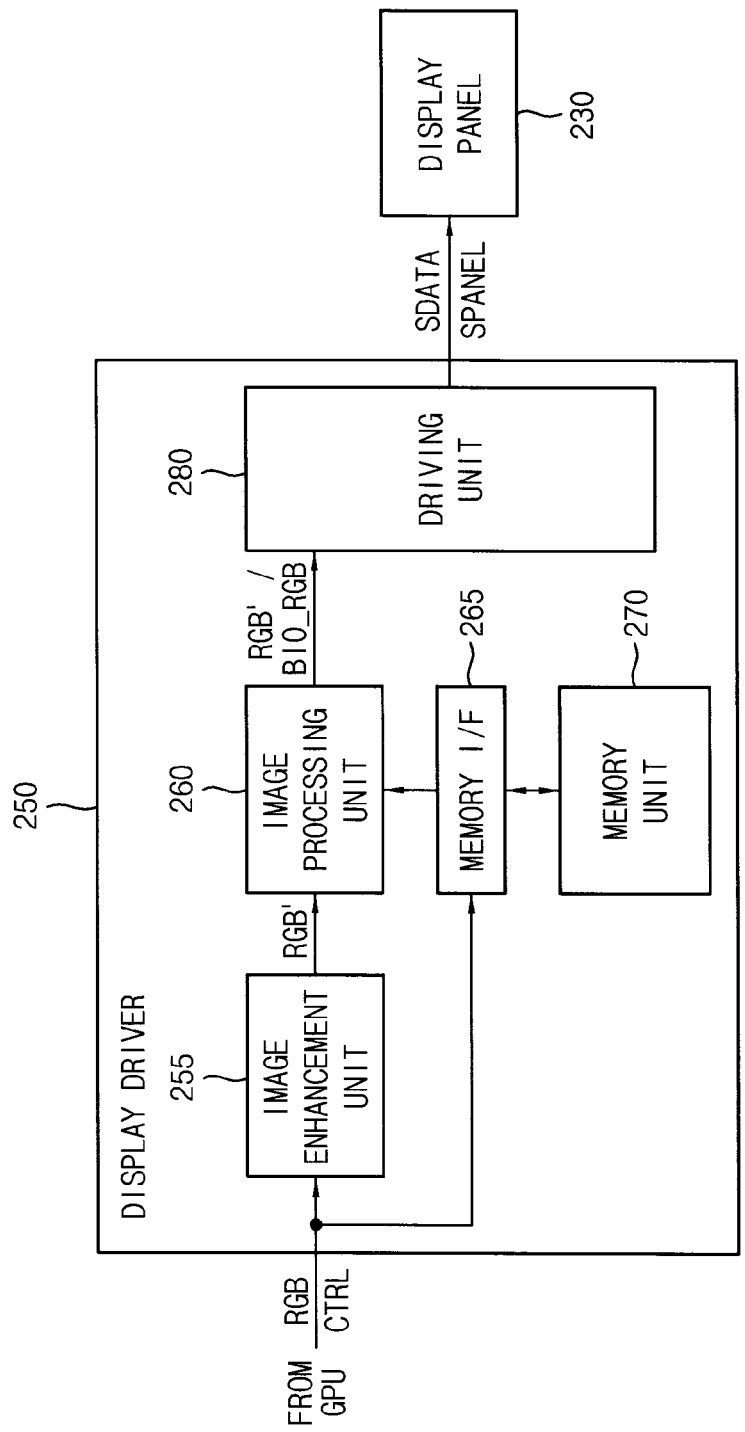
FIG. 2 is a block diagram illustrating an exemplary embodiment of a display driver having a bioeffect image providing function, in accordance with the invention.

FIG. 2 is a block diagram illustrating an exemplary embodiment of a display driver having a bioeffect image providing function, in accordance with exemplary embodiments.

Referring to FIG. 2, an exemplary embodiment of a display driver 250 may include an image enhancement unit 255, an image processing unit 260, a memory interface 265, a memory unit 270 and a driving unit 280. In some exemplary embodiments, the display driver 250 may be implemented as a single chip. The display driver 250 may further include a timing controller that controls operation timings of the display driver 250.

The image enhancement unit 255 may receive first image data RGB for an original image and predetermined control signals CTRL from a GPU. In one exemplary embodiment, for example, the control signals CTRL may include a vertical synchronization signal, a horizontal synchronization signal, a data enable signal, a clock signal, etc. The image enhancement unit 255 may perform an image enhancement process, such as luminance compensation, automatic backlight control ("ABC"), gamma correction or image quality improvement, for example, for the first image data RGB.

The memory unit 270 may store information about a bioeffect image. In some exemplary embodiments, the information about the bioeffect image may be written into the memory unit 270 when the display driver 250 is manufactured. In other exemplary embodiments, the information about the bioeffect image may be stored and updated in the memory unit 270 by an external device (e.g., the GPU) via the memory interface 265. In one exemplary embodiment, for example, while a display device including the display driver 250 operates in a sleep mode, the information about the bioeffect image may be stored and updated in the memory unit 270 via the memory interface 265. In some exemplary embodiments, the information about the bioeffect image may include second image data BIO_RGB for the bioeffect image. According to exemplary embodiments, the bioeffect image corresponding to the second image data BIO_RGB may be a behavior inducing image, a phototherapy image, a color weakness compensation image or a biorhythm control image. According to exemplary embodiments, the second image data BIO_RGB stored in the memory unit 270 may be binary image data, or may be image data having two or more bits for each pixel. In other exemplary embodiments, the information about the bioeffect image may include information about a modulation operation performed by the image processing unit 260. In one exemplary embodiment, for example, the information about the modulation operation may include positions of modulated data in a frame, values of data to be added or multiplied, indication of which one of the red, green and blue sub-pixel data are modulated, coefficients of the modulation operation, etc.

The image processing unit 260 may receive a processed first image data RGB', which is the first image data RGB to which the image enhancement process is performed by the image enhancement unit 255. The image processing unit 260 may provide the driving unit 280 with the first image data RGB' as it is in a normal mode. In a bioeffect mode, the processing unit 260 may provide the driving unit 280 with the processed first image data RGB' as it is at a first frame, and may provide the driving unit 280 with the second image data BIO_RGB for the bioeffect image instead of the processed first image data RGB' at a second frame. In some exemplary embodiments, the second image data BIO_RGB for the bioeffect image may be stored in the memory unit 270, and the image processing unit 260 may output the second image data BIO_RGB stored in the memory unit 270 instead of the first image data RGB at the second frame. In other exemplary embodiments, the image processing unit 260 may generate the second image data BIO_RGB by modulating the processed first image data RGB', and may output the generated second image data BIO_RGB to the driving unit 280 at the second frame. In one exemplary embodiment, for example, the image processing unit 260 may generate the second image data BIO_RGB by synthesizing the first image data RGB and image data for a predetermined image (e.g., the behavior inducing image, the photo-therapy image, the color weakness compensation image, the biorhythm control image, etc.). In other examples, the image processing unit 260 may generate the second image data BIO_RGB by increasing or decreasing at least one of red sub-pixel data, green sub-pixel data and blue sub-pixel data included in the processed first image data RGB'.

The driving unit 280 may drive a display panel based on the processed first image data RGB' or the second image data BIO_RGB provided from the image processing unit 260. In one exemplary embodiment, for example, the driving unit 280 may provide a data signal SDATA and a panel signal SPANEL (e.g., a scan signal, an emission control signal, etc.) to the display panel 230 to display an image corresponding to the processed first image data RGB' or the second image data BIO_RGB. In an exemplary embodiment, where the driving unit 280 receives the second image data BIO_RGB from the image processing unit 260, the driving unit 280 may drive the display panel 230 to display the bioeffect image based on the second image data BIO_RGB, and thus the bioeffect image may be provided to a user. In some exemplary embodiments, the driving unit 280 may include a gate driver, a source driver, etc.

As described above, an exemplary embodiment of the display driver 250 according to the invention may drive the display panel 230 based on the second image data BIO_RGB for the bioeffect image instead of the first image data RGB at one or more frames per a predetermined number of frames. Accordingly, the bioeffect image, such as the behavior inducing image, the photo-therapy image, the color weakness compensation image or the biorhythm control image, for example, may be provided to the user. In such an embodiment, the display driver 250 may have the bioeffect image providing function in itself without data processing of an external device, and thus power consumption and a data processing amount of a mobile device 100 for providing the bioeffect image may be reduced.

Figure 3:
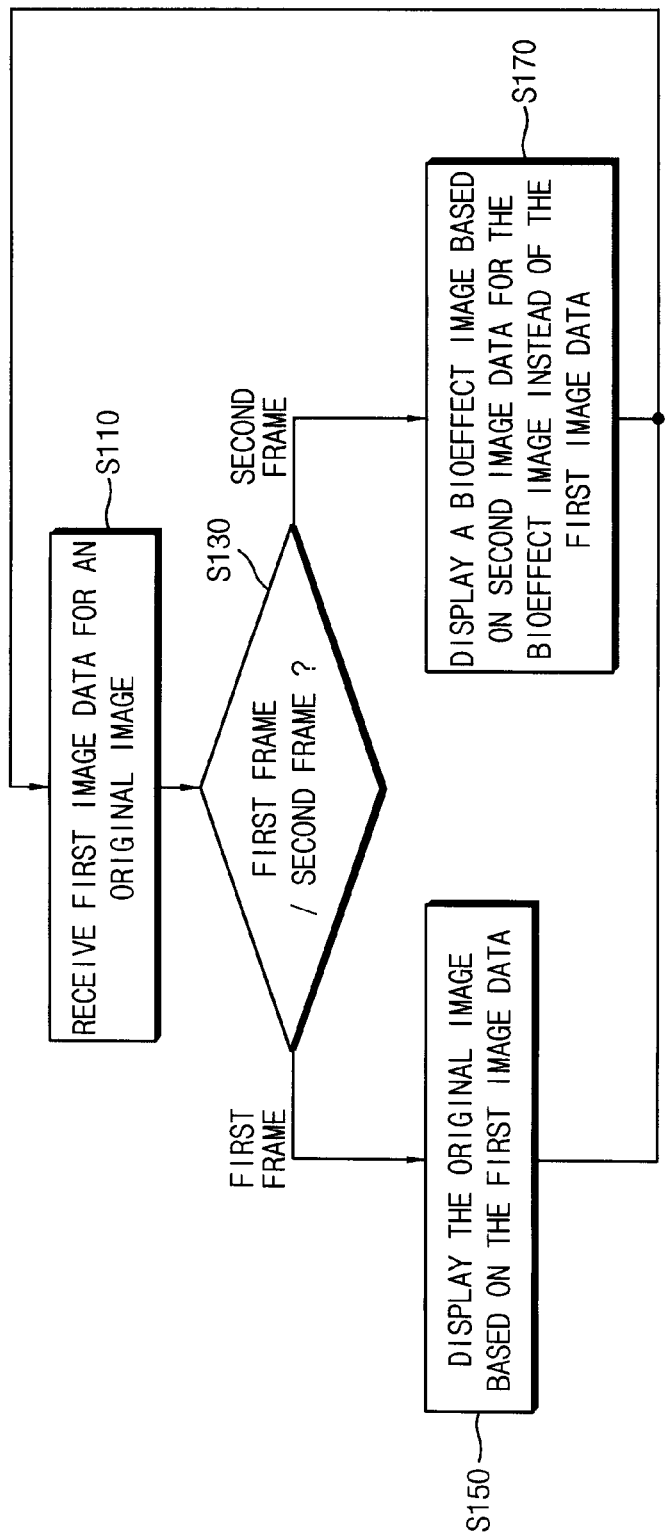
FIG. 3 is a flowchart illustrating an exemplary embodiment of a method of operating a display device to provide a bioeffect image, in accordance with the invention.

FIG. 3 is a flowchart illustrating an exemplary embodiment of a method of operating a display device to provide a bioeffect image, in accordance with the invention.

Referring to FIGS. 1 through 3, a display driver 250 may receive first image data RGB of a frame (S110). At a first frame (S130: FIRST FRAME), an image processing unit 260 included in the display driver 250 may output the received first image data RGB as it is. A driving unit 280 included in the display driver 250 may drive a display panel 230 based on the first image data RGB. The display panel 230 may display an original image corresponding to the first image data RGB (S150).

At a second frame after a predetermined number of first frames (S130: SECOND FRAME), the image processing unit 260 may output second image data BIO_RGB for a bioeffect image instead of the first image data RGB. The driving unit 280 may drive the display panel 230 based on the second image data BIO_RGB, and the display panel 230 may display the bioeffect image corresponding to the second image data BIO_RGB (S170). In some exemplary embodiments, the bioeffect image may be a behavior inducing image, a biorhythm control image, a color weakness compensation image, a photo-therapy image, etc. In other exemplary embodiments, the bioeffect image may be a synthesized image where the original image and at least one of the behavior inducing image, the biorhythm control image, the color weakness compensation image and the photo-therapy image are synthesized. In some exemplary embodiments, the bioeffect image may be periodically displayed. In one exemplary embodiment, for example, after the original image is displayed during N consecutive first frames, where N is an integer greater than 0, the bioeffect image may be displayed during M consecutive second frames, where M is an integer greater than 0. Thus, the bioeffect image may be displayed with a period of M+N frames.

In some exemplary embodiments, the display driver 250 may include a memory unit 270 that stores the second image data BIO_RGB for the bioeffect image, and the image processing unit 260 may output the second image data BIO_RGB stored in the memory unit 270 instead of the first image data RGB at the second frame.

In other exemplary embodiments, the image processing unit 260 may generate the second image data BIO_RGB by modulating the first image data RGB, and may output the second image data BIO_RGB to the driving unit 280 at the second frame. According to exemplary embodiments, the image processing unit 260 may generate the second image data BIO_RGB by synthesizing the first image data RGB and image data for a predetermined image (e.g., the behavior inducing image, the biorhythm control image, the color weakness compensation image, the photo-therapy image, etc.), or may generate the second image data BIO_RGB by increasing or decreasing at least one of red sub-pixel data, green sub-pixel data and blue sub-pixel data included in the first image data RGB.

As described above, in exemplary embodiments of and a mobile device or a display device including the display driver 250, since the display driver 250 has the bioeffect image providing function in itself without data processing of an external device, power consumption and a data processing amount of the mobile device for providing the bioeffect image may be reduced.

Figure 4:
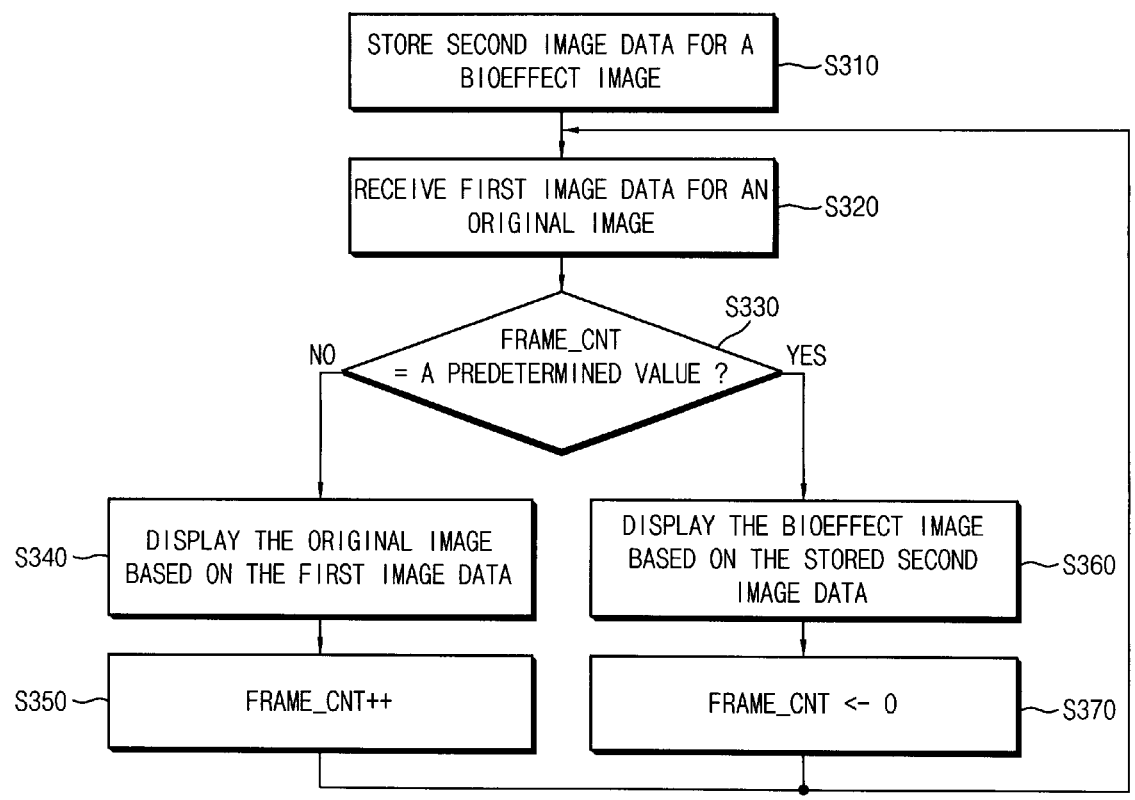
FIG. 4 is a flowchart illustrating another exemplary embodiment of a method of operating a display device to provide a bioeffect image, in accordance with the invention.
Figure 5:
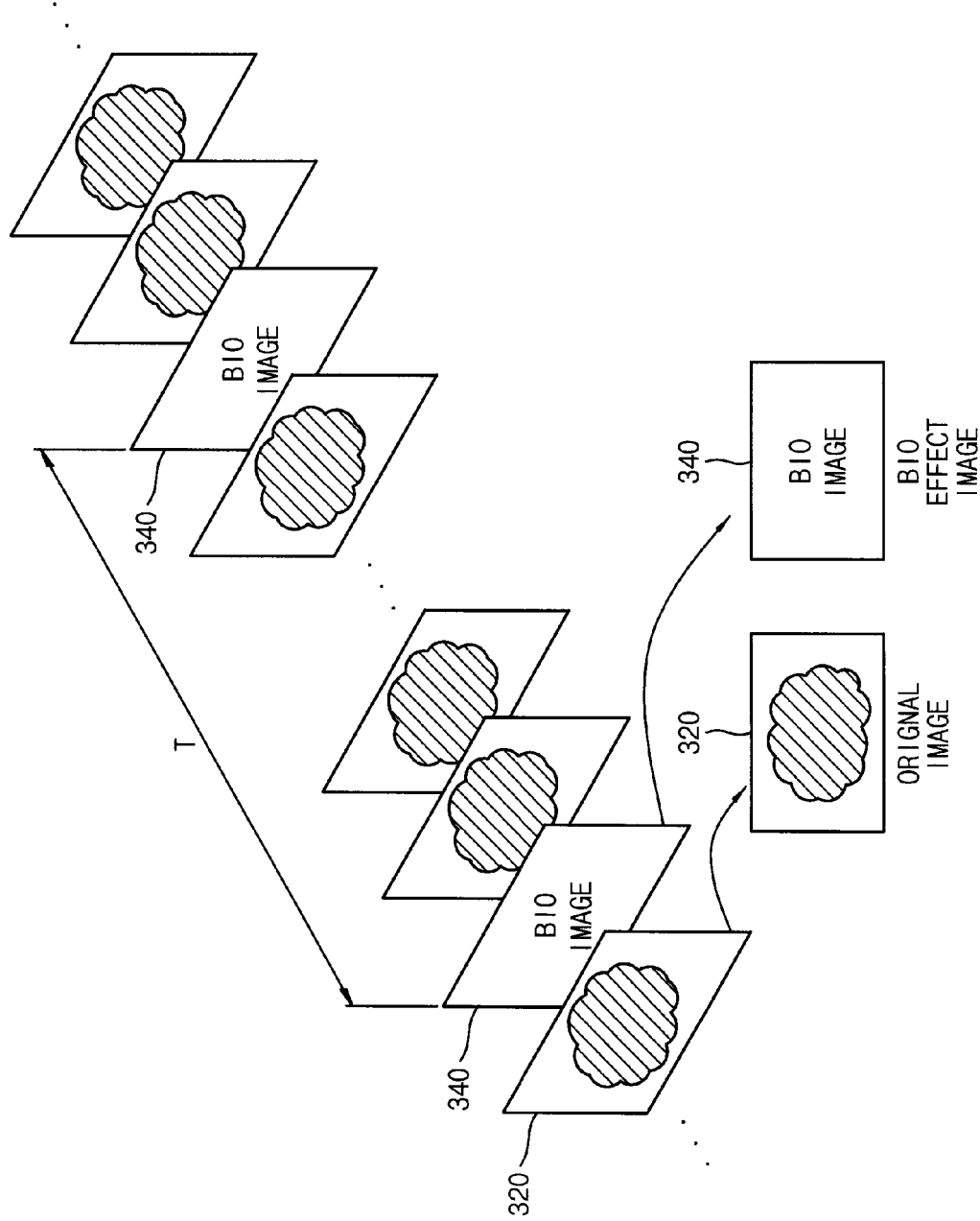
FIG. 5 is a diagram illustrating an exemplary embodiment of image frames displayed by the method of FIG. 4.

FIG. 4 is a flowchart illustrating another exemplary embodiment of a method of operating a display device to provide a bioeffect image, in accordance with the invention, and FIG. 5 is a diagram illustrating an exemplary embodiment of image frames displayed by the method of FIG. 4.

Referring to FIGS. 1, 2, 4 and 5, a memory unit 270 included in a display driver 250 may store second image data BIO_RGB for a bioeffect image 340 (S310). According to exemplary embodiments, the second image data BIO_RGB for the bioeffect image 340 may be image data for a behavior inducing image, image data for a biorhythm control image, image data for a color weakness compensation image or image data for a photo-therapy image.

The display driver 250 may receive first image data RGB corresponding to one frame (S320). To periodically display the bioeffect image 340, the display driver 250 may compare a frame count FRAME_CNT for indicating a number of received frames with a predetermine value corresponding to a desired period T (S330). When the frame count FRAME_CNT is not equal to or does not match the predetermined value (S330: NO), an image processing unit 260 included in the display driver 250 may output the received first image data RGB, a driving unit 280 included in the display driver 250 may drive a display panel 230 based on the first image data RGB, and the display panel 230 may display the original image 320 corresponding to the first image data RGB (S340). When the display panel 230 displays the original image 320 corresponding to the first image data RGB of a frame, the display driver 250 may increase the frame count FRAME_CNT by 1 (S350). A display device 200 including the display driver 250 may display the original image 320 until the frame count FRAME_CNT reaches the predetermined number.

When the frame count FRAME_CNT matches or is equal to the predetermined value (S330: YES), the image processing unit 260 may output the second image data BIO_RGB stored in the memory unit 270 instead of the first image data RGB, the driving unit 280 may drive the display panel 230 based on the second image data BIO_RGB, and the display panel 230 may display the bioeffect image 340 corresponding to the second image data BIO_RGB (S360). According to exemplary embodiments, the bioeffect image 340 may be a behavior inducing image, a biorhythm control image, a color weakness compensation image or a photo-therapy image. The display driver 250 may initialize the frame count FRAME_CNT to zero (0) (S370), and may repeat operations described above. Thus, the display device 200 may display the bioeffect image 340 with the period T.

Accordingly, as illustrated in FIG. 5, in an exemplary embodiment of a mobile device 100 or the display device 200 including the display driver 250, the original image 320 may be displayed, and the bioeffect image 340 may be displayed instead of the original image 320 at one or more frames per period T. As described above, in an exemplary embodiment of the mobile device 100 or the display device 200 including the display driver 250, where the display driver 250 has the bioeffect image providing function in itself without data processing of an external device, power consumption and a data processing amount of the mobile device 100 for providing the bioeffect image may be reduced.

Figure 6:
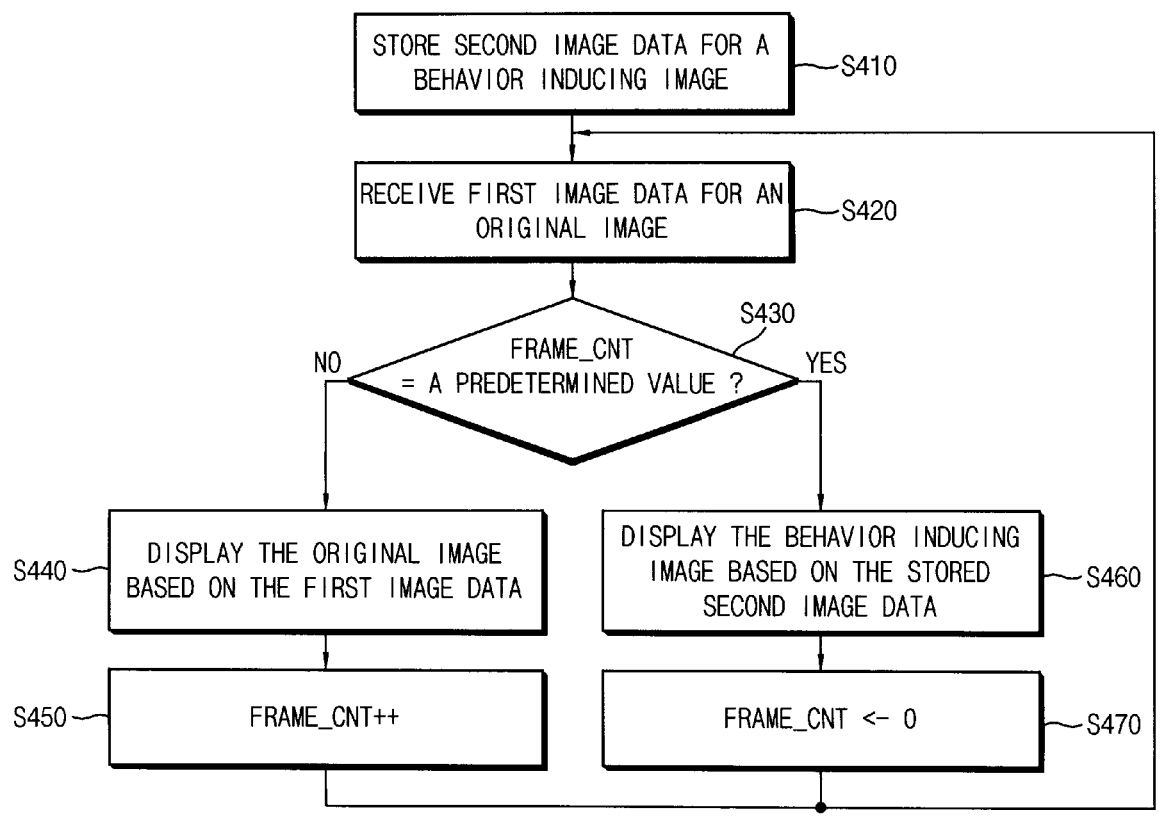
FIG. 6 is a flowchart illustrating an exemplary embodiment of a method of operating a display device to provide a behavior inducing image, in accordance with the invention.
Figure 7:
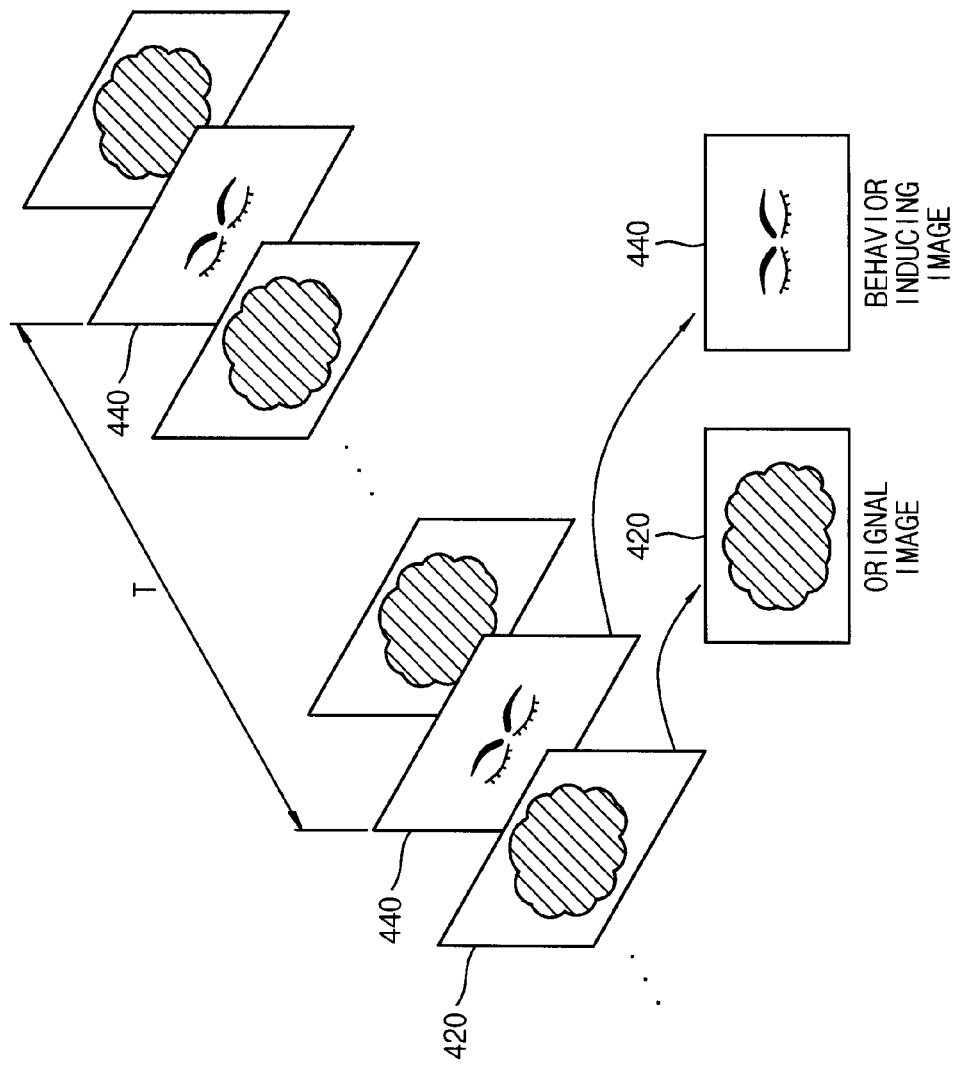
FIG. 7 is a diagram illustrating an exemplary embodiment of image frames displayed by the method of FIG. 6.

FIG. 6 is a flowchart illustrating an exemplary embodiment of a method of operating a display device to provide a behavior inducing image, in accordance with the invention, and FIG. 7 is a diagram illustrating an exemplary embodiment of image frames displayed by the method of FIG. 6.

Referring to FIGS. 1, 2, 6 and 7, a memory unit 270 included in a display driver 250 may store second image data BIO_RGB for a behavior inducing image 440 for inducing a predetermined behavior of a user (S410). In some exemplary embodiments, the behavior inducing image 440 may be a conformity image or a blinking inducing image that induces a user to blink eyes of the user based on a conformity effect.

The display driver 250 may receive first image data RGB corresponding to a frame (S420). To periodically display the behavior inducing image 440, the display driver 250 may compare a frame count FRAME_CNT for indicating a number of received frames with a predetermine value corresponding to a desired period T (S430). When the frame count FRAME_CNT does not match the predetermined value (S430: NO), an image processing unit 260 may output the received first image data RGB, a driving unit 280 may drive a display panel 230 based on the first image data RGB, and the display panel 230 may display the original image 420 corresponding to the first image data RGB (S440). When, the display panel 230 displays the original image 420 corresponding to the first image data RGB of a frame, the display driver 250 may increase the frame count FRAME_CNT by 1 (S450). A display device 200 including the display driver 250 may display the original image 420 until the frame count FRAME_CNT reaches the predetermined number.

When the frame count FRAME_CNT matches the predetermined value (S430: YES), the image processing unit 260 may output the second image data BIO_RGB stored in the memory unit 270 instead of the first image data RGB, the driving unit 280 may drive the display panel 230 based on the second image data BIO_RGB, and the display panel 230 may display the behavior inducing image 440 corresponding to the second image data BIO_RGB (S460). In one exemplary embodiment, for example, the behavior inducing image 440 may be the blinking inducing image, and the user to which the blinking inducing image is provided may blink the eyes of the user by the conformity effect. The display driver 250 may initialize the frame count FRAME_CNT to 0 (S470), and may repeat operations described above. Thus, the display device 200 may display the behavior inducing image 440 with the period T.

In some exemplary embodiments, the behavior inducing image 440 may be displayed for a predetermined duration shorter than a duration that is consciously perceptible by a user. In one exemplary embodiment, for example, the behavior inducing image 440 may be displayed during one frame per period T. In such embodiments, the behavior inducing image 440 may not be consciously perceived by the user, and thus any inconvenience of the user may not be caused.

In such embodiments, the behavior inducing image 440 may be provided as a subliminal stimulus to the user, such that the behavior inducing image 440 may induce a behavior of the user, for example, eye-blinking of the user by the conformity effect or subliminal learning.

Accordingly, as illustrated in FIG. 7, in an exemplary embodiment of a mobile device 100 or the display device 200 including the display driver 250, the original image 420 may be displayed, and the behavior inducing image 440 may be displayed instead of the original image 420 at one or more frames per period T.

Figure 8:
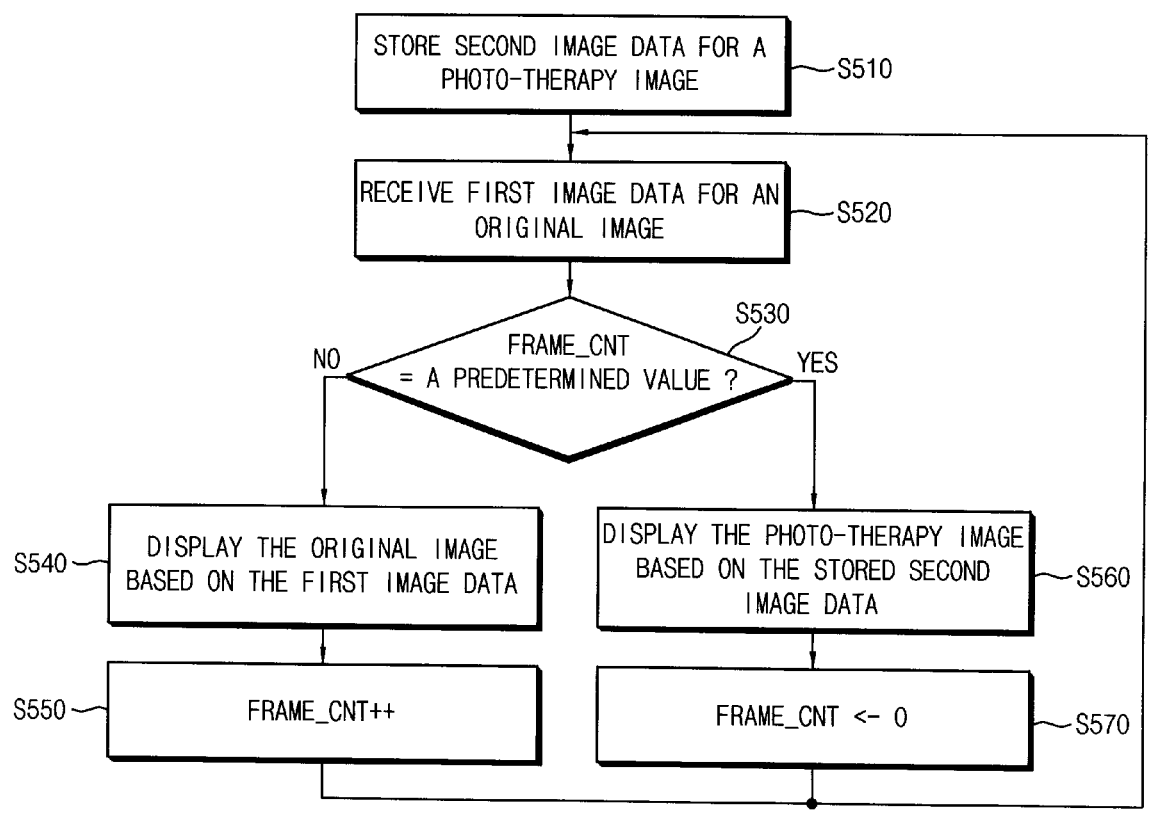
FIG. 8 is a flowchart illustrating an exemplary embodiment of a method of operating a display device to provide a photo-therapy image, in accordance with the invention.
Figure 9:
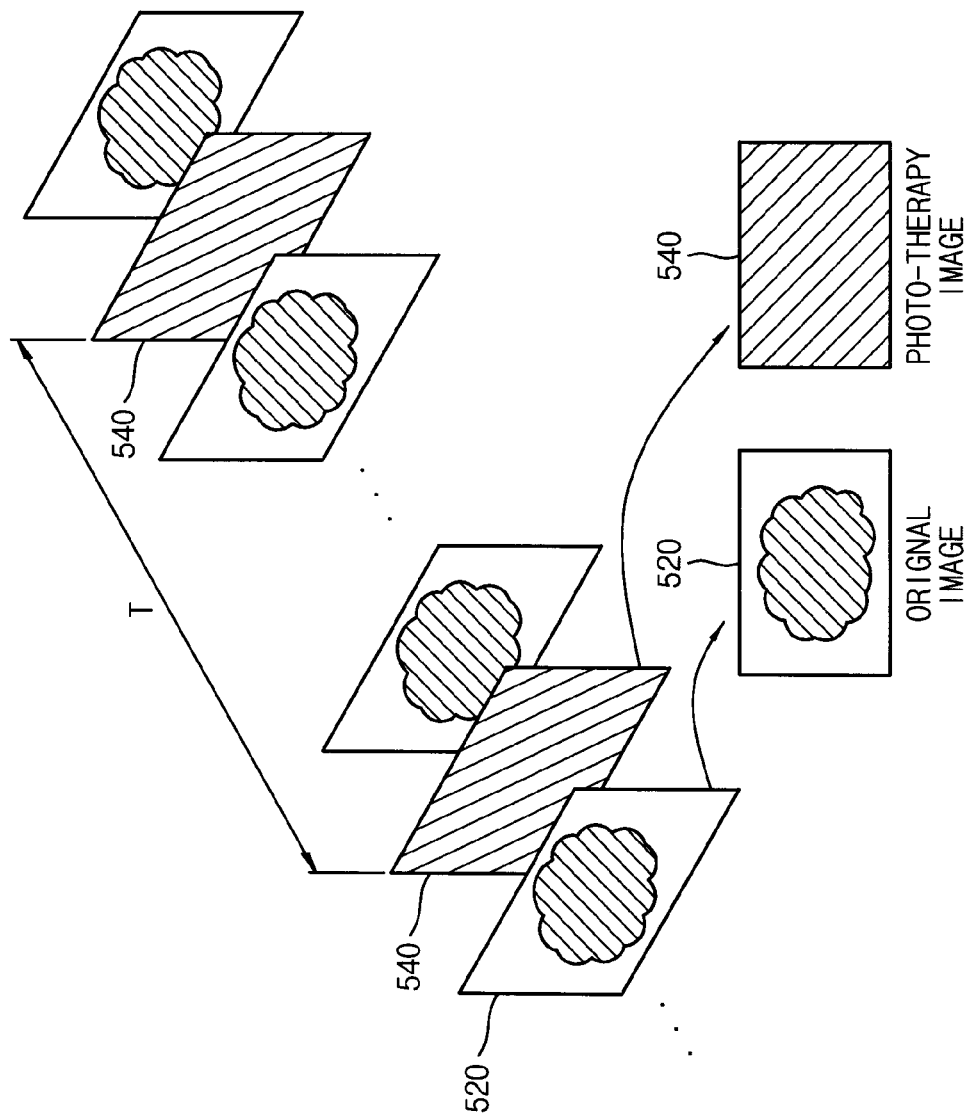
FIG. 9 is a diagram illustrating an exemplary embodiment of image frames displayed by the method of FIG. 8.

FIG. 8 is a flowchart illustrating an exemplary embodiment of a method of operating a display device to provide a photo-therapy image, in accordance with exemplary embodiments, FIG. 9 is a diagram illustrating an exemplary embodiment of image frames displayed by the method of FIG. 8, and FIGS. 10A through 10C are diagrams for describing exemplary embodiments of the photo-therapy image provided by the method of FIG. 8.

Referring to FIGS. 1, 2 and 8 through 10, a memory unit 270 included in a display driver 250 may store second image data BIO_RGB for a photo-therapy image 540 (S510). In some exemplary embodiments, the photo-therapy image 540 may be an anti-inflammatory therapy image, a pimple therapy image, a wrinkle therapy image, a skin lightening therapy image, a depression therapy image or a sterilization therapy image, for example.

The display driver 250 may receive first image data RGB corresponding to one frame (S520). To periodically display the photo-therapy image 540, the display driver 250 may compare a frame count FRAME_CNT for indicating a number of received frames with a predetermine value corresponding to a desired period T (S530). When the frame count FRAME_CNT does not match the predetermined value (S530: NO), an image processing unit 260 may output the received first image data RGB, a driving unit 280 may drive a display panel 230 based on the first image data RGB, and the display panel 230 may display the original image 520 corresponding to the first image data RGB (S540). When the display panel 230 displays the original image 520 corresponding to the first image data RGB of a frame, the display driver 250 may increase the frame count FRAME_CNT by 1 (S550). A display device 200 including the display driver 250 may display the original image 520 until the frame count FRAME_CNT reaches the predetermined number.

When the frame count FRAME_CNT matches the predetermined value (S530: YES), the image processing unit 260 may output the second image data BIO_RGB stored in the memory unit 270 instead of the first image data RGB, the driving unit 280 may drive the display panel 230 based on the second image data BIO_RGB, and the display panel 230 may display the photo-therapy image 540 corresponding to the second image data BIO_RGB (S560). In some exemplary embodiments, the photo-therapy image 540 may be displayed for a predetermined duration shorter than a duration that is consciously perceptible by a user.

Figure 10A:
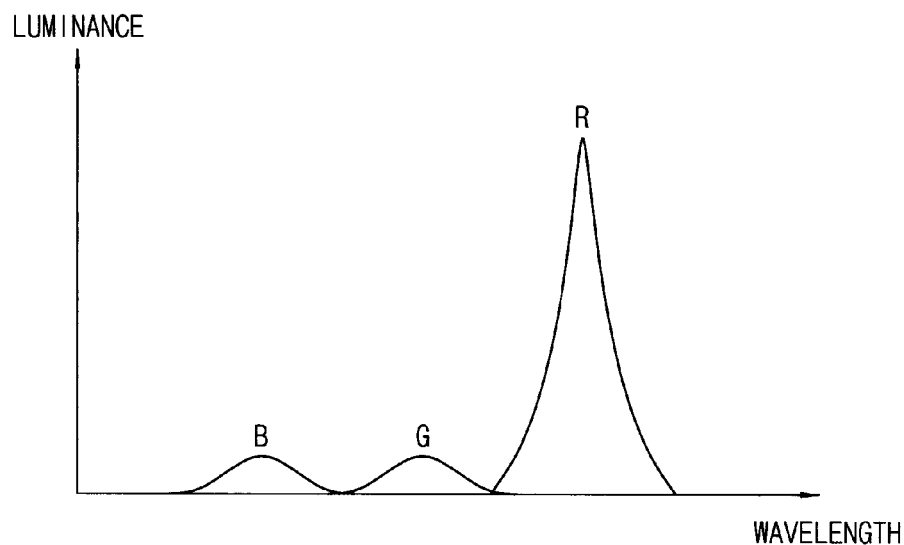
FIGS. 10A through 10C are diagrams for describing exemplary embodiments of a photo-therapy image provided by the method of FIG. 8.

In some exemplary embodiments, the second image data BIO_RGB stored in the memory unit 270 may include red sub-pixel data greater than green sub-pixel data and blue sub-pixel data for each pixel. In one exemplary embodiment, for example, the second image data BIO_RGB may include the green sub-pixel data having a value of zero (0), the blue sub-pixel data having a value of zero (0), and the red sub-pixel data having a value that is not zero (0) (e.g., a maximum value) for each pixel (S570). Accordingly, as illustrated in FIG. 10A, the photo-therapy image 540 may have red luminance higher than green luminance and blue luminance to provide the anti-inflammatory therapy, the pimple therapy or the wrinkle therapy.

Figure 10B:
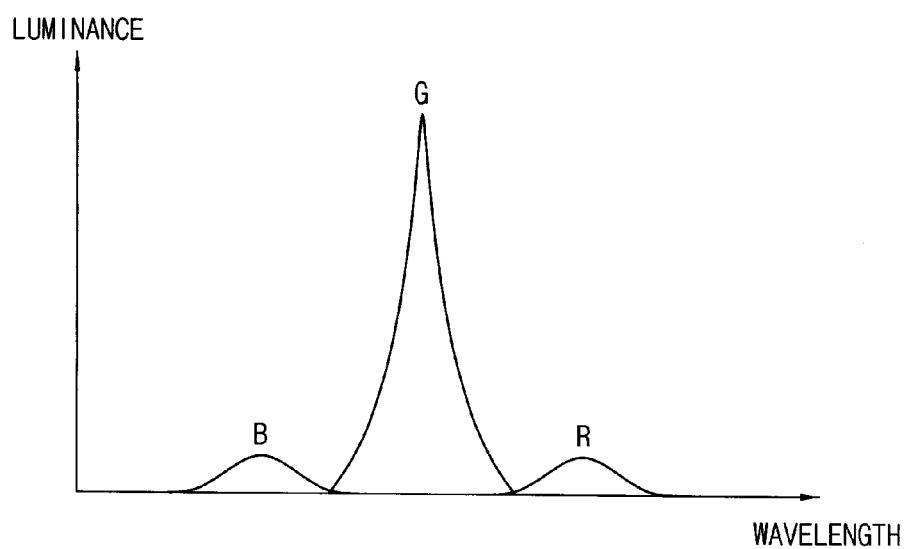

In other exemplary embodiments, the second image data BIO_RGB stored in the memory unit 270 may include the green sub-pixel data greater than the red sub-pixel data and the blue sub-pixel data for each pixel. In one exemplary embodiment, for example, the second image data BIO_RGB may include the red sub-pixel data having a value of zero (0), the blue sub-pixel data having a value of zero (0), and the green sub-pixel data having a value that is not zero (0) (e.g., the maximum value) for each pixel. Accordingly, as illustrated in FIG. 10B, the photo-therapy image 540 may have the green luminance higher than the red luminance and the blue luminance to provide the skin lightening therapy.

Figure 10C:
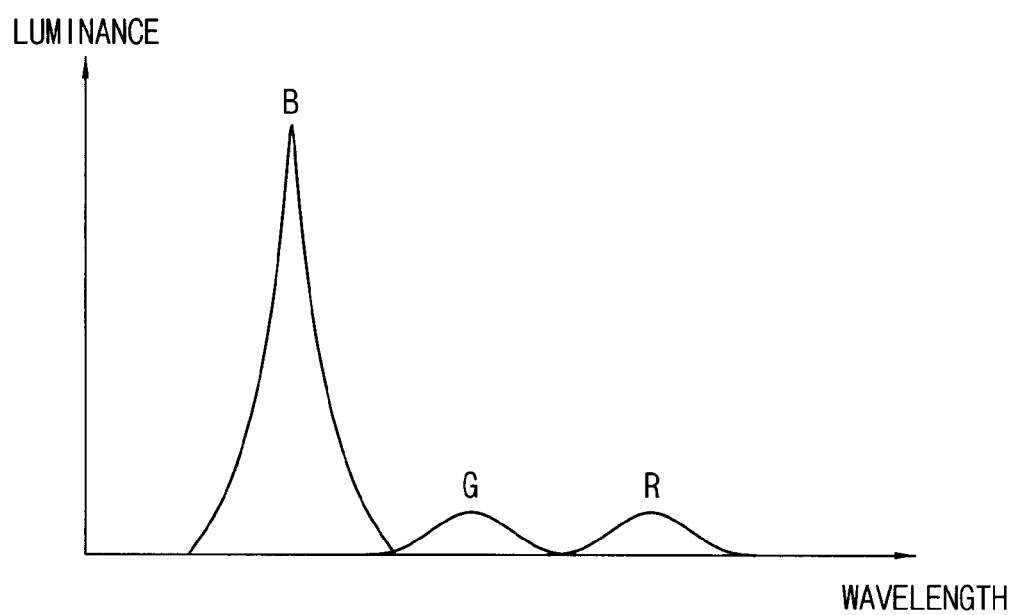

In still other exemplary embodiments, the second image data BIO_RGB stored in the memory unit 270 may include the blue sub-pixel data greater than the red sub-pixel data and the green sub-pixel data for each pixel. In one exemplary embodiment, for example, the second image data BIO_RGB may include the red sub-pixel data having a value of zero (0), the green sub-pixel data having a value of zero (00, and the blue sub-pixel data having a value that is not zero (0) (e.g., the maximum value) for each pixel. Accordingly, as illustrated in FIG. 10C, the photo-therapy image 540 may have the blue luminance higher than the red luminance and the green luminance to provide the depression therapy or the sterilization therapy.

Accordingly, as illustrated in FIG. 9, in an exemplary embodiment of a mobile device 100 or the display device 200 including the display driver 250, the original image 520 may be displayed, and the photo-therapy image 540 may be displayed instead of the original image 520 at one or more frames per period T.

Figure 11:
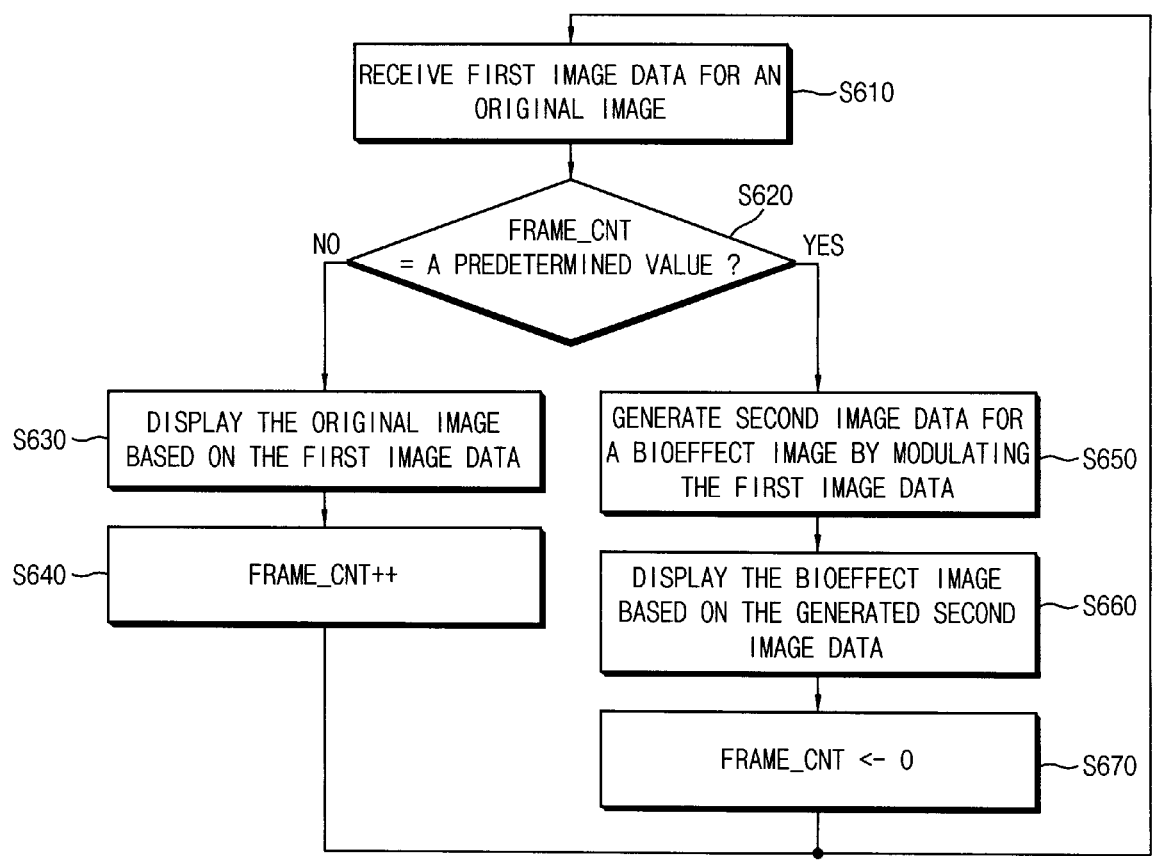
FIG. 11 is a flowchart illustrating another exemplary embodiment of a method of operating a display device to provide a bioeffect image, in accordance with the invention.
Figure 12:
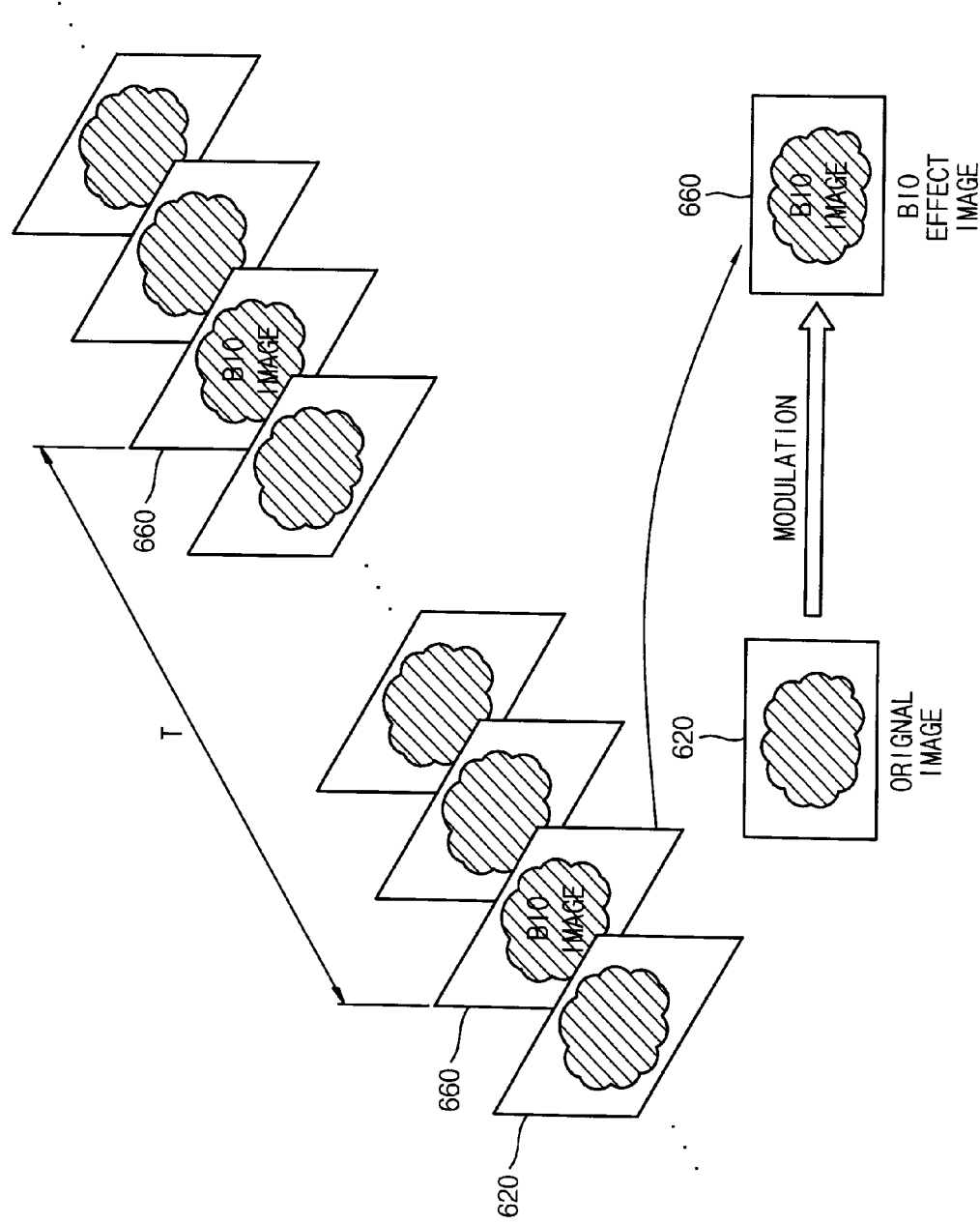
FIG. 12 is a diagram illustrating an exemplary embodiment of image frames displayed by the method of FIG. 11.

FIG. 11 is a flowchart illustrating another exemplary embodiment of a method of operating a display device to provide a bioeffect image, in accordance with the invention, and FIG. 12 is a diagram illustrating an exemplary embodiment of image frames displayed by the method of FIG. 11.

Referring to FIGS. 1, 2, 11 and 12, a display driver 250 may receive first image data RGB corresponding to one frame (S610). To periodically display a bioeffect image 660, the display driver 250 may compare a frame count FRAME_CNT for indicating a number of received frames with a predetermine value corresponding to a desired period T (S620). When the frame count FRAME_CNT does not match the predetermined value (S620: NO), an image processing unit 260 may output the received first image data RGB, a driving unit 280 may drive a display panel 230 based on the first image data RGB, and the display panel 230 may display an original image 620 corresponding to the first image data RGB (S630). When the display panel 230 displays an original image 620 corresponding to the first image data RGB of a frame, the display driver 250 may increase the frame count FRAME_CNT by 1 (S640). A display device 200 including the display driver 250 may display the original image 620 until the frame count FRAME_CNT reaches the predetermined number.

When the frame count FRAME_CNT matches the predetermined value (S620: YES), the image processing unit 260 may generate second image data BIO_RGB for the bioeffect image 660 by modulating the first image data RGB, and may output the second image data BIO_RGB to the driving unit 280 (S650). In some exemplary embodiments, the image processing unit 260 may synthesize the first image data RGB and image data for a predetermined image (e.g., a behavior inducing image, a biorhythm control image, a color weakness compensation image, a photo-therapy image, etc.) to generate the bioeffect image 600 where the original image 620 is overlaid with the predetermined image. In other exemplary embodiments, the image processing unit 260 may generate the second image data BIO_RGB by increasing or decreasing at least one of red sub-pixel data, green sub-pixel data and blue sub-pixel data included in the first image data RGB.

The driving unit 280 may drive the display panel 230 based on the second image data BIO_RGB, and the display panel 230 may display the bioeffect image 660 corresponding to the second image data BIO_RGB (S660). In some exemplary embodiments, the bioeffect image 660 may be a synthesized image where the original image 620 and at least one of the behavior inducing image, the biorhythm control image, the color weakness compensation image and the photo-therapy image are synthesized. The display driver 250 may initialize the frame count FRAME_CNT to zero (0) (S670), and may repeat operations described above. Thus, the display device 200 may display the bioeffect image 660 with the period T.

Accordingly, as illustrated in FIG. 12, in an exemplary embodiment of a mobile device 100 or the display device 200 including the display driver 250, the original image 620 may be displayed, and the bioeffect image 660 that is generated by modulating the original image 620 may be displayed at one or more frames per period T. As described above, in such an embodiment of the mobile device 100 the display device 200 including the display driver 250, the display driver 250 has the bioeffect image providing function in itself without data processing of an external device, and power consumption and a data processing amount of the mobile device 100 for providing the bioeffect image may be reduced.

Figure 13:
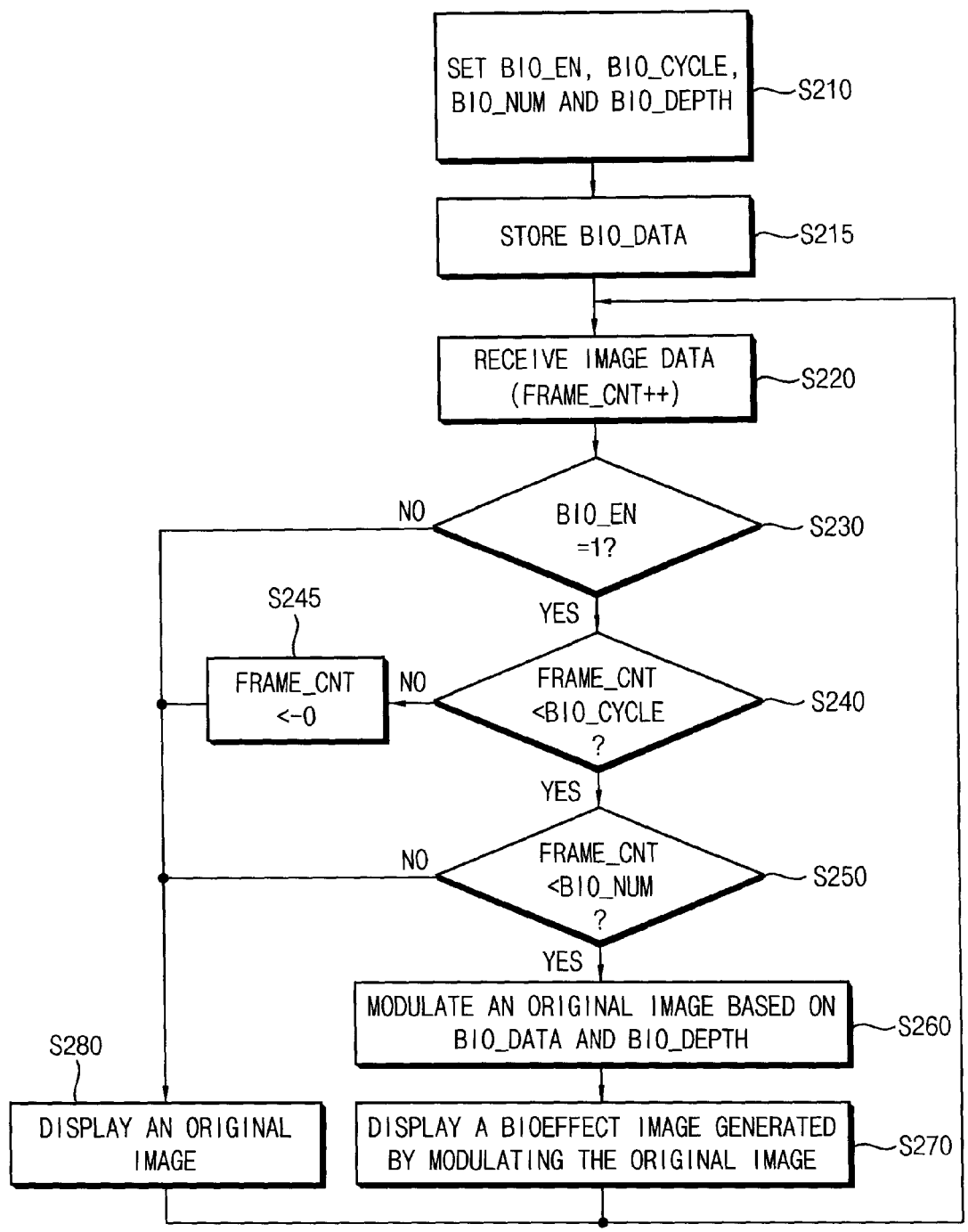
FIG. 13 is a flowchart illustrating another exemplary embodiment of a method of operating a display device to provide a bioeffect image, in accordance with the invention.

FIG. 13 is a flowchart illustrating another exemplary embodiment of a method of operating a display device to provide a bioeffect image, in accordance with the invention.

Referring to FIGS. 1, 2 and 13, setting values of a modulation operation for an original image to be performed by an image processing unit 260 may be set (S210). In one exemplary embodiment, for example, the setting values of the modulation operation may include BIO_EN representing whether a bioeffect image providing function is to be activated, BIO_CYCLE representing the number of frames corresponding to a period of the modulation operation, BIO_NUM representing the number of frames of a bioeffect image in one period, and BIO_DEPTH representing data weight or a data ratio of a predetermined image (e.g., a behavior inducing image, a biorhythm control image, a color weakness compensation image, a photo-therapy image, etc.) to the original image. According to exemplary embodiments, the setting values of the modulation operation may be set by a selection of the user, may be automatically set by an external device (e.g., by a GPU 115), or may be set to default values. In some exemplary embodiments, the setting values of the modulation operation may be set or updated while the display device 200 operates in a sleep mode.

A memory unit 270 may store information BIO_DATA for a bioeffect image (S215). According to exemplary embodiments, the information BIO_DATA for the bioeffect image may be written or updated when the display driver 250 is manufactured or when the display device 200 operates in the sleep mode. According to exemplary embodiments, the information BIO_DATA for the bioeffect image may include the setting values of the modulation operation and/or binary or more than two bit image data for the predetermined image to be synthesized to the original image.

The display driver 250 may receive first image data RGB corresponding to one frame (S220). The display driver 250 may increase a frame count FRAME_CNT for indicating a number of received frames by 1. When the bioeffect image providing function is not to be activated (e.g., BIO_EN=0) (S230: NO), the image processing unit 260 may not perform a modulation operation, and the display driver 250 may drive a display panel 230 based on the first image data RGB to display the original image (S280).

When the bioeffect image providing function is to be activated (e.g., BIO_EN=1) (S230: YES), and the frame count FRAME_CNT is less than the number of frames BIO_CYCLE corresponding to the period of the modulation operation and the number of frames BIO_NUM of the bioeffect image (S240: YES and S250: YES), the image processing unit 260 may perform the modulation operation that modulates the first image data RGB based on the information BIO_DATA for the bioeffect image (S260). In some exemplary embodiments, the image processing unit 260 may perform a synthesis operation that overlays the original image with the predetermined image (e.g., the behavior inducing image, the biorhythm control image, the color weakness compensation image, the photo-therapy image, etc.) with the set data weight/ratio BIO_DEPTH.

The display driver 250 may drive the display panel 230 to display the bioeffect image where the original image and the predetermined image are synthesized (S270). The display driver 250 may drive the display panel 230 to display the bioeffect image until the frame count FRAME_CNT reaches the number of the frames BIO_NUM of the bioeffect image.

When the frame count FRAME_CNT is greater than the number of frames BIO_NUM of the bioeffect image (S250: NO), the image processing unit 260 may not perform the modulation operation, and the display driver 250 may drive the display panel 230 based on the first image data RGB to display the original image (S280). Further, if the frame count FRAME_CNT is greater than the number of frames BIO_CYCLE corresponding to the period of the modulation operation (S240: NO), the display driver 250 may initialize the frame count FRAME_CNT to 0 (S245), and may repeat operations described above.

Accordingly, in an exemplary embodiment of a mobile device 100 or the display device 200 including the display driver 250, the bioeffect image where the original image and the predetermined image are synthesized may be displayed at first predetermined number of frames BIO_NUM per second predetermined number of frames BIO_CYCLE corresponding to the period. As described above, in such an embodiment, the display driver 250 has the bioeffect image providing function in itself without data processing of an external device, and power consumption and a data processing amount of the mobile device 100 for providing the bioeffect image may be reduced.

Figure 14:
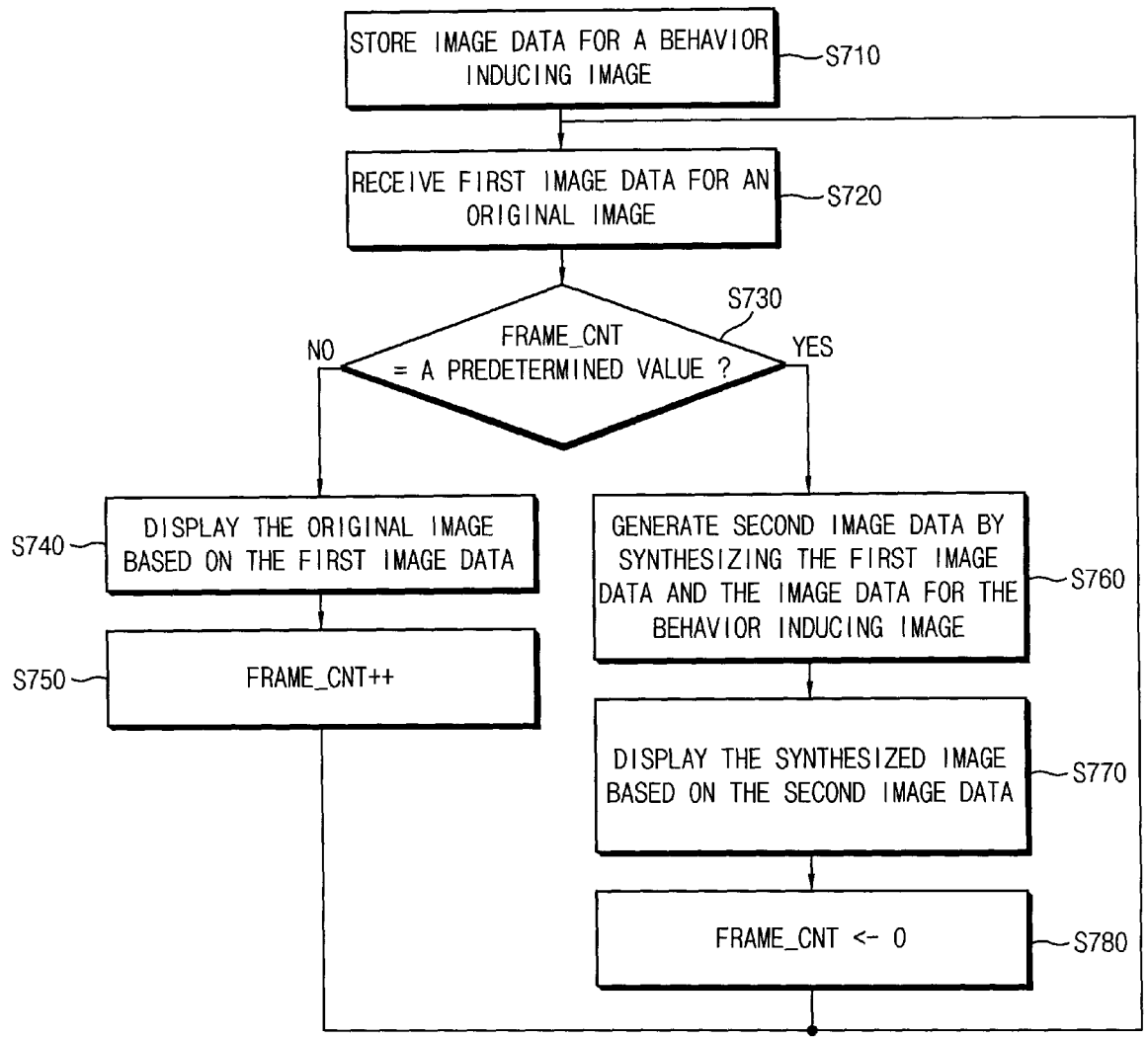
FIG. 14 is a flowchart illustrating an exemplary embodiment of a method of operating a display device to provide a behavior inducing image, in accordance with the invention.
Figure 16C:
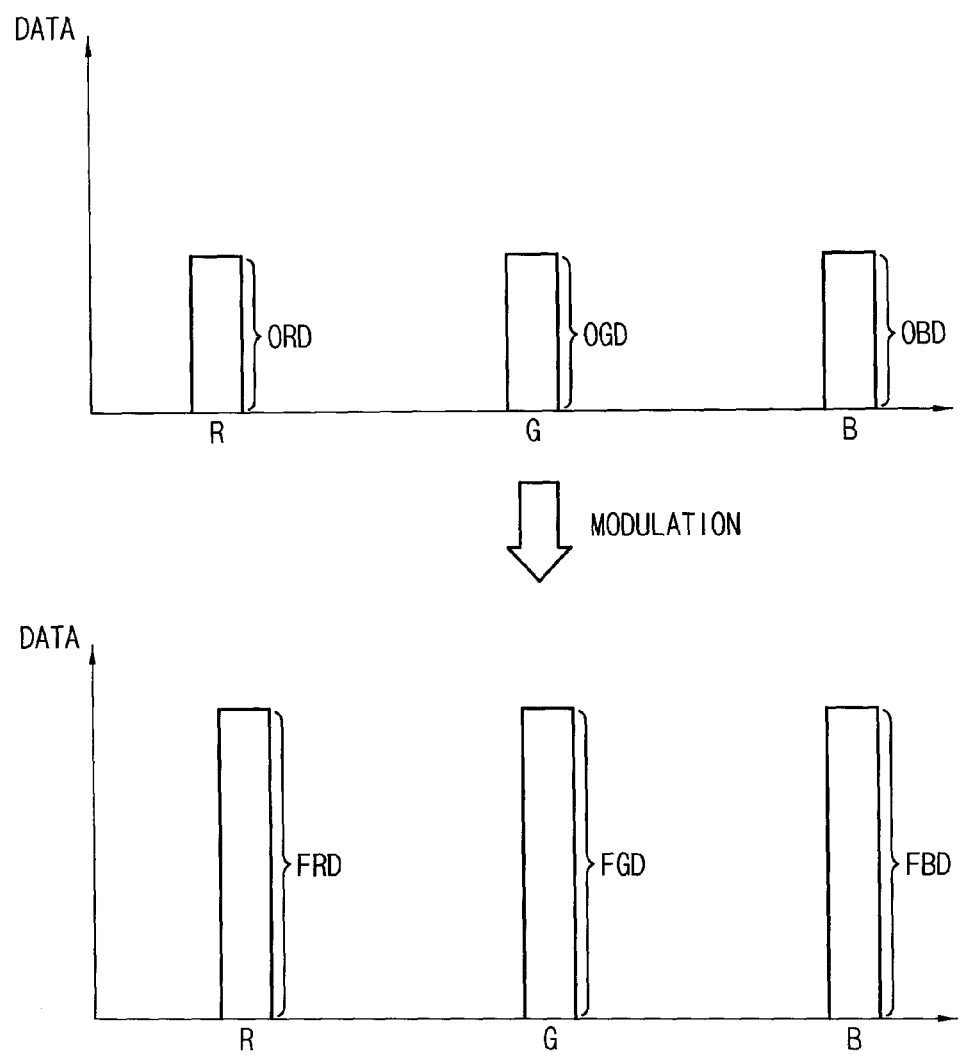

FIG. 14 is a flowchart illustrating an exemplary embodiment of a method of operating a display device to provide a behavior inducing image, in accordance with the invention, FIG. 15 is a diagram illustrating an exemplary embodiments of image frames displayed by the method of FIG. 14, and FIGS. 16A through 16C are diagrams for describing exemplary embodiments of a modulation operation performed by the method of FIG. 14.

Referring to FIGS. 1, 2 and 14 through 16C, a memory unit 270 included in a display driver 250 may store image data for a behavior inducing image 740 for inducing a predetermined behavior of a user (S710). In some exemplary embodiments, the behavior inducing image 740 may be a conformity image or a blinking inducing image that induces a user to blink eyes of the user based on a conformity effect.

The display driver 250 may receive first image data RGB corresponding to one frame (S720). To periodically display the behavior inducing image 740, the display driver 250 may compare a frame count FRAME_CNT for indicating a number of received frames with a predetermine value corresponding to a desired period T (S730). When the frame count FRAME_CNT does not match the predetermined value (S730: NO), an image processing unit 260 may output the received first image data RGB, a driving unit 280 may drive a display panel 230 based on the first image data RGB, and the display panel 230 may display the original image 720 corresponding to the first image data RGB (S740). When the display panel 230 displays the original image 720 corresponding to the first image data RGB of a frame, the display driver 250 may increase the frame count FRAME_CNT by 1 (S750). A display device 200 including the display driver 250 may display the original image 720 until the frame count FRAME_CNT reaches the predetermined number.

When the frame count FRAME_CNT matches the predetermined value (S730: YES), the image processing unit 260 may generate second image data BIO_RGB by synthesizing the first image data RGB and the image data for the behavior inducing image 740 stored in the memory unit 270 (S760).

In one exemplary embodiment, for example, as illustrated in FIG. 16A, the first image data RGB may include original red sub-pixel data ORD, original green sub-pixel data OGD and original blue sub-pixel data OBD for each pixel, and the image processing unit 260 may perform a modulation operation that multiplies the original red sub-pixel data ORD by a value f(BRD) determined by red sub-pixel data of the image data for the behavior inducing image 740, multiplies the original green sub-pixel data OGD by a value f(BGD) determined by green sub-pixel data of the image data for the behavior inducing image 740, and multiplies the original blue sub-pixel data OBD by a value f(BBD) determined by blue sub-pixel data of the image data for the behavior inducing image 740. In one exemplary embodiment, for example, the values f(BRD), f(BGD) and f(BBD) determined by the red, green and blue sub-pixel data of the image data for the behavior inducing image 740 may be changed according to the set data weight/ratio.

In another exemplary embodiment, as illustrated in FIG. 16B, the image processing unit 260 may perform a modulation operation that adds the value f(BRD) determined by the red sub-pixel data of the image data for the behavior inducing image 740 to the original red sub-pixel data ORD, adds the value f(BGD) determined by the green sub-pixel data of the image data for the behavior inducing image 740 to the original green sub-pixel data OGD, and adds the value f(BBD) determined by the blue sub-pixel data of the image data for the behavior inducing image 740 to the original blue sub-pixel data OBD.

In another exemplary embodiment, as illustrated in FIG. 16B, the image processing unit 260 may perform a modulation operation that converts the original red, green and blue sub-pixel data ORD, OGD and OBD to fixed values FRD, FGD and FBD.

The driving unit 280 may drive the display panel 230 based on the second image data BIO_RGB, and the display panel 230 may display a bioeffect image 760 where the original image 720 and the behavior inducing image 740 are synthesized (S770). In one exemplary embodiment, for example, the behavior inducing image 740 may be a blinking inducing image, and the user to which the bioeffect image 760 including the blinking inducing image is provided may blink the user's eyes by the conformity effect. The display driver 250 may initialize the frame count FRAME_CNT to zero (0) (S780), and may repeat operations described above. Thus, the display device 200 may display the bioeffect image 760 with the period T.

In some exemplary embodiments, the bioeffect image 760 where the original image 720 and the behavior inducing image 740 are synthesized may be displayed for a predetermined duration shorter than a duration that is consciously perceptible by a user. In such embodiments, the behavior inducing image 740 may not be consciously perceived by the user, and thus any inconvenience of the user may be effectively prevented. In such embodiments, the behavior inducing image 740 is provided as a subliminal stimulus to the user, such that the behavior inducing image 740 may induce a behavior of the user, for example, eye-blinking of the user, by the conformity effect or subliminal learning.

Accordingly, as illustrated in FIG. 15, in an exemplary embodiment of a mobile device 100 or the display device 200 including the display driver 250, the original image 720 may be displayed, and the bioeffect image 760 where the original image 720 and the behavior inducing image 740 are synthesized may be displayed instead of the original image 720 at one or more frames per period T.

Figure 17:
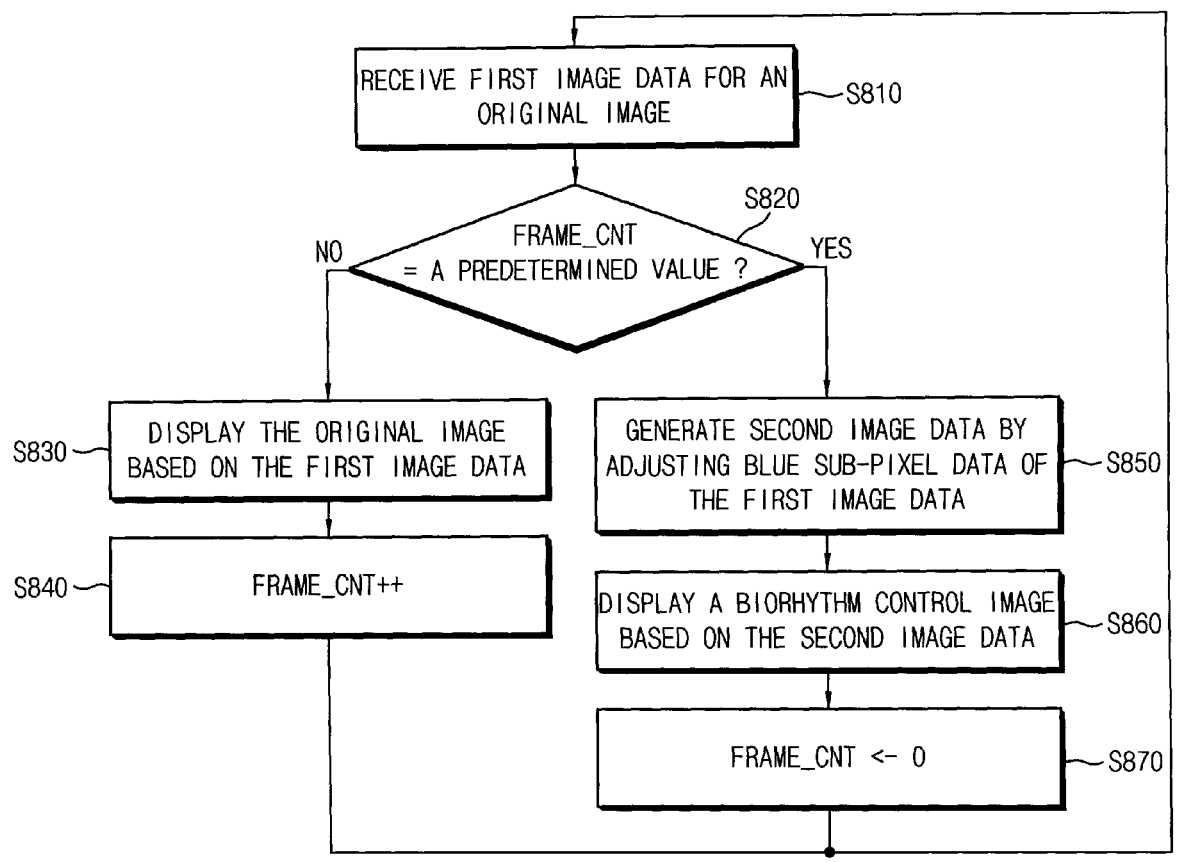
FIG. 17 is a flowchart illustrating an exemplary embodiment of a method of operating a display device to provide a biorhythm control image, in accordance with the invention.

FIG. 17 is a flowchart illustrating an exemplary embodiment of a method of operating a display device to provide a biorhythm control image, in accordance with the invention, and FIGS. 18A and 18B are diagrams for describing examples of modulation operations performed by the method of FIG. 17.

Referring to FIGS. 1, 2, 17, 18A and 18B, a display driver 250 may receive first image data RGB corresponding to one frame (S810). The display driver 250 may compare a frame count FRAME_CNT for indicating a number of received frames with a predetermine value corresponding to a desired period (S820). When the frame count FRAME_CNT does not match the predetermined value (S820: NO), an image processing unit 260 may output the received first image data RGB, a driving unit 280 may drive a display panel 230 based on the first image data RGB, and the display panel 230 may display an original image corresponding to the first image data RGB (S830). When the display panel 230 displays an original image corresponding to the first image data RGB of a frame, the display driver 250 may increase the frame count FRAME_CNT by 1 (S840). A display device 200 including the display driver 250 may display the original image until the frame count FRAME_CNT reaches the predetermined number.

When the frame count FRAME_CNT matches the predetermined value (S820: YES), the image processing unit 260 may generate second image data BIO_RGB for a bioeffect image (e.g., a biorhythm control image) by adjusting blue sub-pixel data included in the first image data RGB (S850).

In some exemplary embodiments, as illustrated in FIG. 18A, the image processing unit 260 may generate the second image data BIO_RGB by decreasing the blue sub-pixel data from the first image data RGB. In such embodiments, the driving unit 280 may drive the display panel 230 based on the second image data BIO_RGB where the blue sub-pixel data are decreased, and the display panel 230 may display the biorhythm control image that prevents suppression of melatonin secretion where the blue luminance is decreased from the original image (S860).

In other exemplary embodiments, as illustrated in FIG. 18B, the image processing unit 260 may generate the second image data BIO_RGB by increasing the blue sub-pixel data from the first image data RGB. In such embodiments, the driving unit 280 may drive the display panel 230 based on the second image data BIO_RGB where the blue sub-pixel data are increased, and the display panel 230 may display the biorhythm control image that suppresses melatonin secretion where the blue luminance is increased from the original image (S860).

The display driver 250 may initialize the frame count FRAME_CNT to zero (0) (S870), and may repeat operations described above. Thus, the display device 200 may display the biorhythm control image with the period.

Accordingly, in an exemplary embodiment of a mobile device 100 or the display device 200 including the display driver 250, the original image may be displayed, and the biorhythm control image where the blue luminance is adjusted from the original image at one or more frame per period.

Figure 19A:
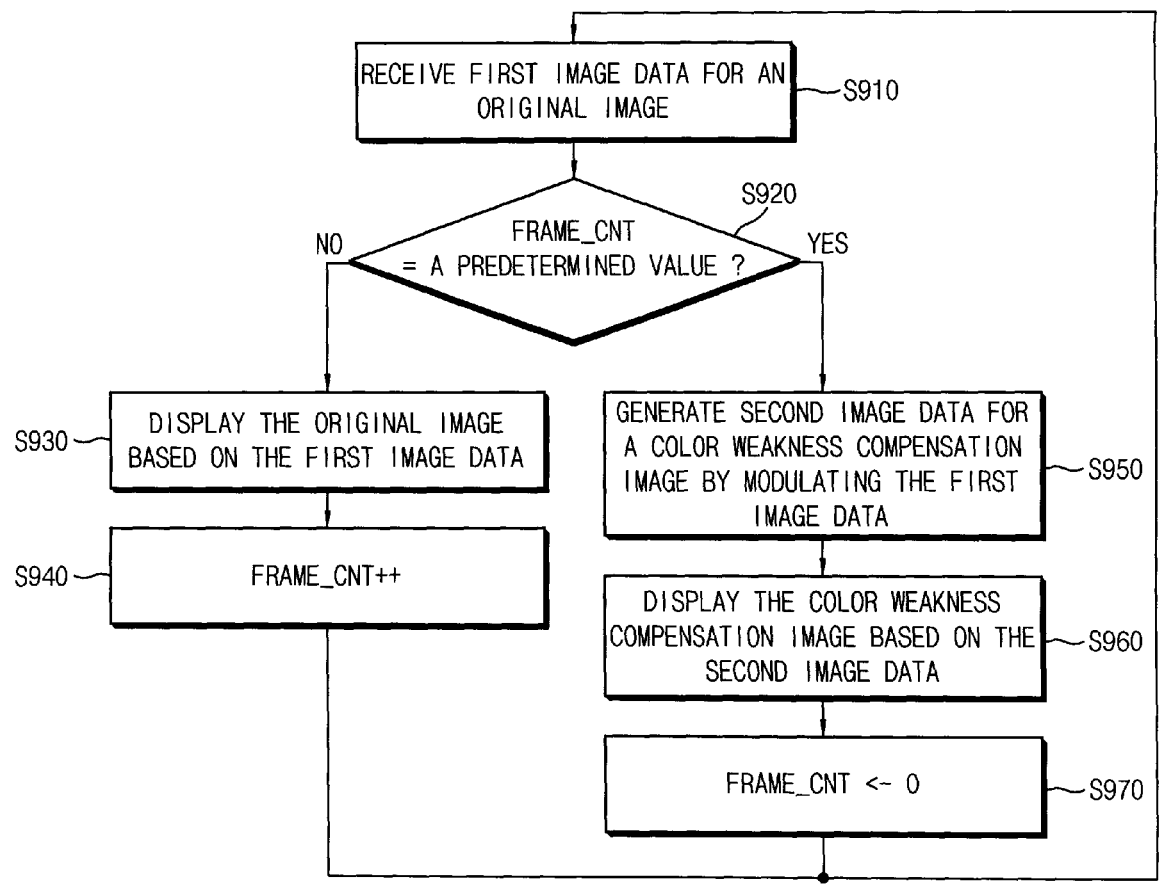
FIG. 19A is a flowchart illustrating an exemplary embodiment of a method of operating a display device to provide a color weakness compensation image, in accordance with the invention.
Figure 19B:
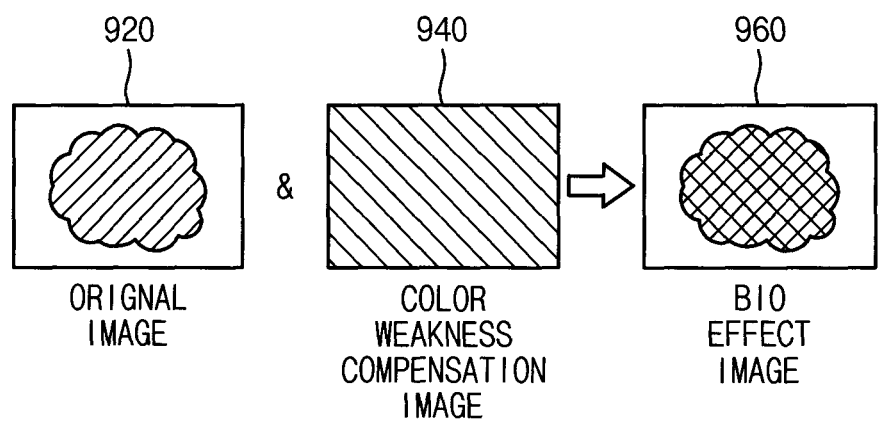
FIG. 19B is a diagram illustrating an exemplary embodiment of image frames displayed by the method of FIG. 19A.

FIG. 19A is a flowchart illustrating an exemplary embodiment of a method of operating a display device to provide a color weakness compensation image, in accordance with the invention, and FIG. 19B is a diagram illustrating an exemplary of image frames displayed by the method of FIG. 19A.

Referring to FIGS. 1, 2, 19A and 19B, a display driver 250 may receive first image data RGB corresponding to one frame (S910). The display driver 250 may compare a frame count FRAME_CNT for indicating a number of received frames with a predetermine value corresponding to a desired period (S920). When the frame count FRAME_CNT does not match the predetermined value (S920: NO), an image processing unit 260 may output the received first image data RGB, a driving unit 280 may drive a display panel 230 based on the first image data RGB, and the display panel 230 may display an original image 920 corresponding to the first image data RGB (S930). When the display panel 230 displays an original image 920 corresponding to the first image data RGB of a frame, the display driver 250 may increase the frame count FRAME_CNT by 1 (S940). A display device 200 including the display driver 250 may display the original image 920 until the frame count FRAME_CNT reaches the predetermined number.

When the frame count FRAME_CNT matches the predetermined value (S920: YES), the image processing unit 260 may generate second image data BIO_RGB for a bioeffect image 960 by modulating the first image data RGB (S950).

In some exemplary embodiments, as illustrated in FIG. 19B, the image processing unit 260 may generate the second image data BIO_RGB for bioeffect image 960 by synthesizing the first image data RGB and image data for a color weakness compensation image 940 to generate the bioeffect image 960 where the original image 920 and the color weakness compensation image 940 are overlaid or synthesized. The driving unit 280 may drive the display panel 230 based on the second image data BIO_RGB, and the display panel 230 may display the bioeffect image 960 where the original image 920 and the color weakness compensation image 940 are synthesized (S960). In one exemplary embodiment, for example, the color weakness compensation image 940 may be an image where red luminance is increased to enhance a visibility of a user having red color weakness, an image where green luminance is increased to enhance a visibility of a user having green color weakness, an image where red and green luminance is increased to enhance a visibility of a user having red and green color weakness.

In other exemplary embodiments, the image processing unit 260 may generate the second image data BIO_RGB by increasing red sub-pixel data of the first image data RGB (S950), the driving unit may drive the display panel 230 based on the second image data BIO_RGB having the increased red sub-pixel data, and the display panel 230 may display the color weakness compensation image where the red luminance is increased from the original image to enhance the visibility of the user having red color weakness (S960).

In still other exemplary embodiments, the image processing unit 260 may generate the second image data BIO_RGB by increasing green sub-pixel data of the first image data RGB (S950), the driving unit may drive the display panel 230 based on the second image data BIO_RGB having the increased green sub-pixel data, and the display panel 230 may display the color weakness compensation image where the green luminance is increased from the original image to enhance the visibility of the user having green color weakness (S960).

The display driver 250 may initialize the frame count FRAME_CNT to zero (0) (S970), and may repeat operations described above. Thus, the display device 200 may display the color weakness compensation image, or the image where the original image and the color weakness compensation image are synthesized with the period.

Accordingly, in an exemplary embodiment of a mobile device 100 or the display device 200 including the display driver 250, the original image may be displayed, and the biorhythm control image where the blue luminance is adjusted from the original image at one or more frames per period.

Figure 20:
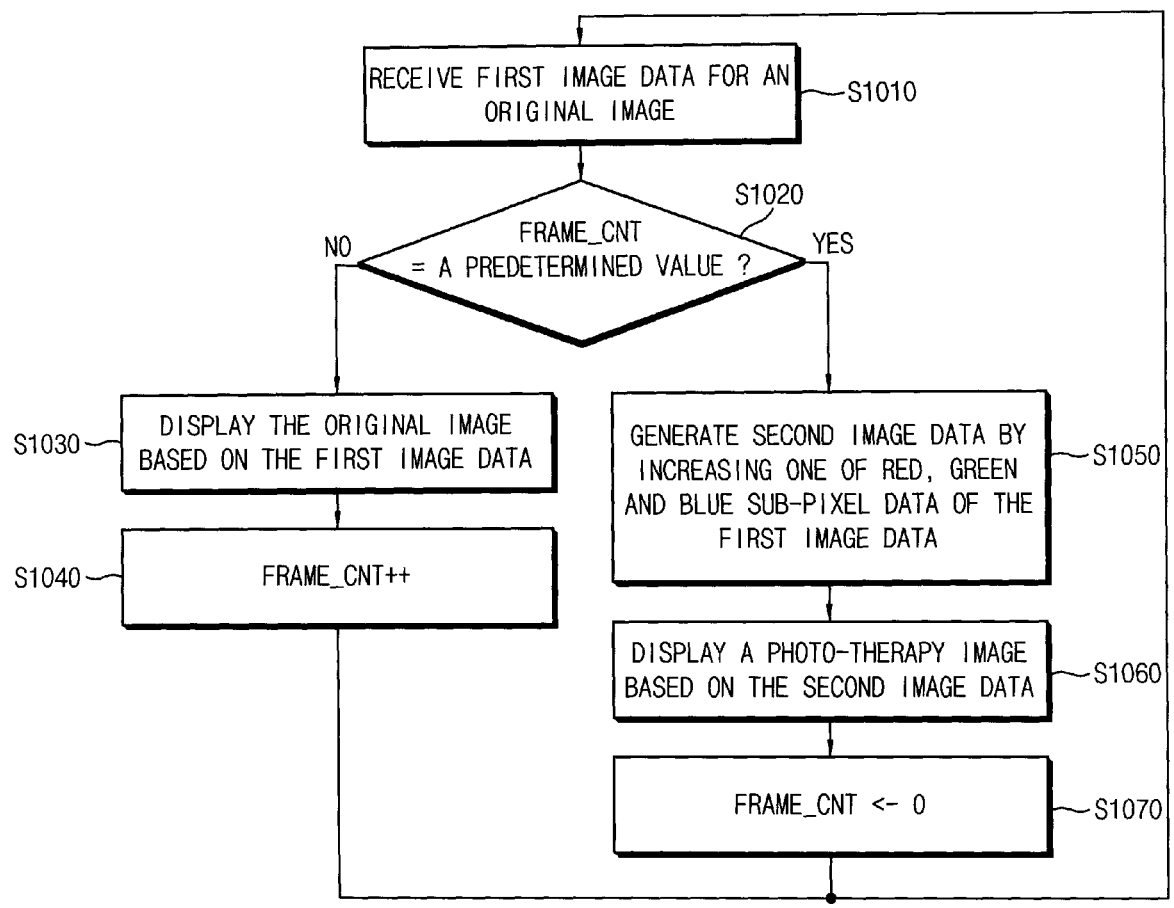
FIG. 20 is a flowchart illustrating an exemplary embodiment of a method of operating a display device to provide a photo-therapy image, in accordance with the invention.
Figure 21C:
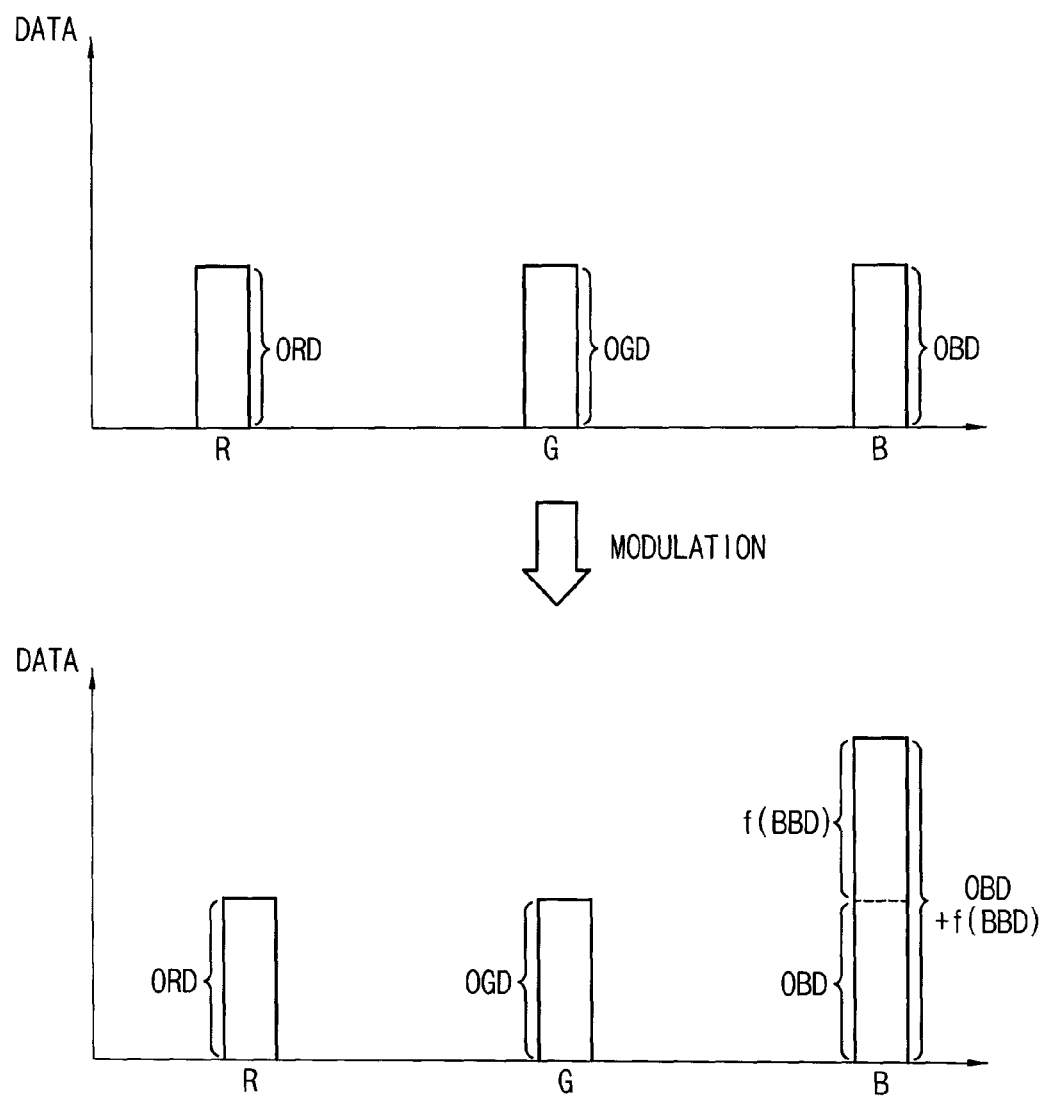

FIG. 20 is a flowchart illustrating an exemplary embodiment of a method of operating a display device to provide a photo-therapy image, in accordance with the invention, and FIGS. 21A through 21C are diagrams for describing examples of modulation operations performed by the method of FIG. 20.

Referring to FIGS. 1, 2 and 20 through 21C, a display driver 250 may receive first image data RGB corresponding to one frame (S1010). The display driver 250 may compare a frame count FRAME_CNT for indicating a number of received frames with a predetermine value corresponding to a desired period (S1020). When the frame count FRAME_CNT does not match the predetermined value (S1020: NO), an image processing unit 260 may output the received first image data RGB, a driving unit 280 may drive a display panel 230 based on the first image data RGB, and the display panel 230 may display an original image corresponding to the first image data RGB (S1030). When the display panel 230 displays an original image corresponding to the first image data RGB of a frame, the display driver 250 may increase the frame count FRAME_CNT by 1 (S1040). A display device 200 including the display driver 250 may display the original image until the frame count FRAME_CNT reaches the predetermined number.

When the frame count FRAME_CNT matches the predetermined value (S1020: YES), the image processing unit 260 may generate second image data BIO_RGB for a photo-therapy image by adjusting one of red sub-pixel data, green sub-pixel data and blue sub-pixel data included in the first image data RGB (S1050).

In some exemplary embodiments, as illustrated in FIG. 21A, the image processing unit 260 may generate the second image data BIO_RGB by increasing the red sub-pixel data of the first image data RGB. In such embodiments, the driving unit 280 may drive the display panel 230 based on the second image data BIO_RGB having the increased red sub-pixel data, and the display panel 230 may display the photo-therapy image where red luminance is increased from the original image (S1060). According to exemplary embodiments, the photo-therapy image having the increased red luminance may be an anti-inflammatory therapy image, a pimple therapy image or a wrinkle therapy image.

In other exemplary embodiments, as illustrated in FIG. 21B, the image processing unit 260 may generate the second image data BIO_RGB by increasing the green sub-pixel data of the first image data RGB. In such embodiments, the driving unit 280 may drive the display panel 230 based on the second image data BIO_RGB having the increased green sub-pixel data, and the display panel 230 may display the photo-therapy image where green luminance is increased from the original image (S1060). According to exemplary embodiments, the photo-therapy image having the increased green luminance may be a skin lightening therapy image.

In still other exemplary embodiments, as illustrated in FIG. 21C, the image processing unit 260 may generate the second image data BIO_RGB by increasing the blue sub-pixel data of the first image data RGB. In such embodiments, the driving unit 280 may drive the display panel 230 based on the second image data BIO_RGB having the increased blue sub-pixel data, and the display panel 230 may display the photo-therapy image where blue luminance is increased from the original image (S1060). According to exemplary embodiments, the photo-therapy image having the increased blue luminance may be a depression therapy image or a sterilization therapy image.

The display driver 250 may initialize the frame count FRAME_CNT to zero (0) (S1070), and may repeat operations described above. Thus, the display device 200 may display the photo-therapy image with the period.

In some exemplary embodiments, at a frame immediately before or after a frame at which the photo-therapy image is displayed, a compensating image that is complementary to the photo-therapy image may be displayed. In one exemplary embodiment, for example, the second image data BIO_RGB for the photo-therapy image are image data where the red sub-pixel data are increased from the first image data RGB, the image processing unit 260 may generate third image data where the red sub-pixel data are decreased from the first image data RGB, and the driving unit may drive the display panel 230 based on the third image data at the frame directly before or after the frame at which the photo-therapy image is displayed. Thus, immediately before or after the photo-therapy image having the increased red luminance is displayed, the compensating image having the decreased red luminance may be displayed. Accordingly, a user may perceive the original image based on the photo-therapy image and the compensating image. Therefore, the photo-therapy image may be provided to the user while the user does not perceive the photo-therapy image, and thereby not causing any inconvenience of the user.

Figure 22:
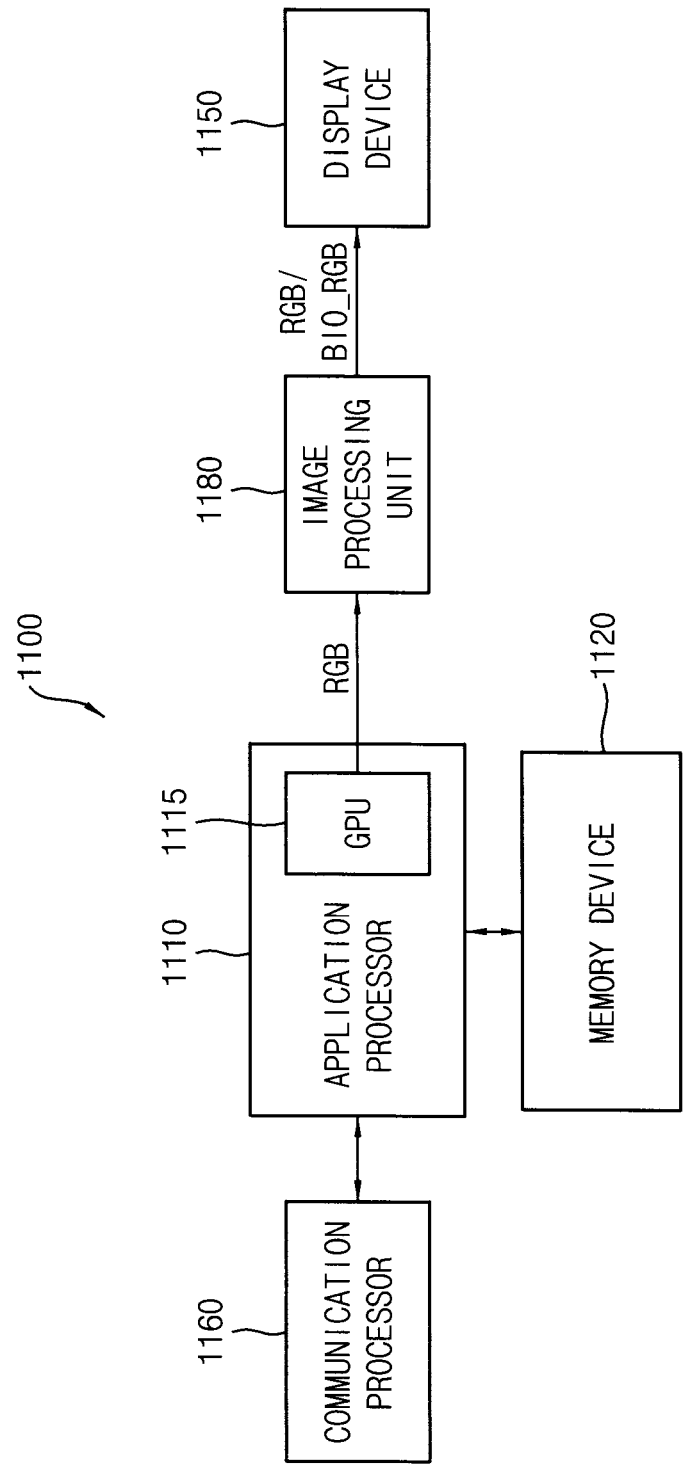
FIG. 22 is a block diagram illustrating another exemplary embodiment of a mobile device including an image processing unit having a bioeffect image providing function, in accordance with the invention.

FIG. 22 is a block diagram illustrating another exemplary embodiment of a mobile device including an image processing unit having a bioeffect image providing function, in accordance with the invention.

Referring to FIG. 22, an exemplary embodiment of a mobile device 1100 includes an application processor 1110, a memory device 1120, a communication processor 1160, a display device 1100 and an image processing unit 1180. The application processor 1110 may include a GPU 1115 that controls the display device 1150. The mobile device 1100 shown in FIG. 22 may have a similar configuration to a mobile device 100 shown in FIG. 1, except that the image processing unit 1180 is implemented as a separate device, integrated circuit or chip from a display driver.

In such an embodiment, as described above, the image processing unit 1180 may be implemented as a separate device, integrated circuit or chip from the application processor 1110 and the display device 1150. The image processing unit 1180 may receive first image data RGB for an original image from the GPU 1115, may provide the first image data RGB to the display device 1150 at a first frame, and may provide second image data BIO_RGB instead of the first image data RGB to the display device 1150. The display device 1150 may receive the first image data RGB for the original image, and may display the original image based on the first image data RGB at the first frame. At the second frame, the display device 1150 may receive the second image data BIO_RGB for the bioeffect image, and may display the bioeffect image based on the second image data BIO_RGB at the second frame. According to exemplary embodiments, the bioeffect image may be a behavior inducing image, a biorhythm control image, a color weakness compensation image or a photo-therapy image, or may be a synthesized image where the original image and one of the behavior inducing image, the biorhythm control image, the color weakness compensation image and the photo-therapy image are synthesized.

Figure 23:
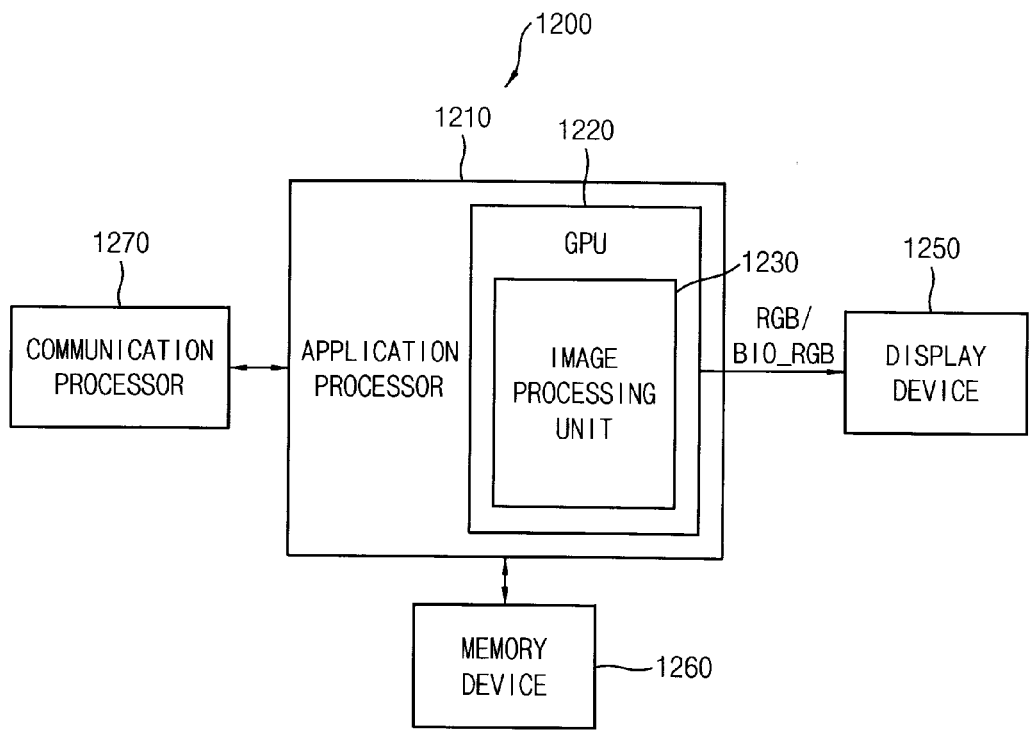
FIG. 23 is a block diagram illustrating another exemplary embodiment of a mobile device including a graphic processing unit having a bioeffect image providing function, in accordance with the invention.

FIG. 23 is a block diagram illustrating another exemplary embodiment of a mobile device including a GPU having a bioeffect image providing function, in accordance with the invention.

Referring to FIG. 23, an exemplary embodiment of a mobile device 1200 includes an application processor 1210, a memory device 1260, a communication processor 1270 and a display device 1250. The application processor 1210 may include a GPU 1220 that controls the display device 1250. The mobile device 1200 shown in FIG. 23 may have a similar configuration to a mobile device 100 shown in FIG. 1, except that an image processing unit 1230 is included in the GPU 1220 of the application processor 1210.

The image processing unit 1230 may provide first image data RGB for an original image to the display device 1250 at a first frame, and may provide second image data BIO_RGB for a bioeffect image instead of the first image data RGB to the display device 1250 at a second frame. In some exemplary embodiments, the GPU 1220 may further include a memory unit for storing the second image data BIO_RGB for the bioeffect image, and the image processing unit 1230 may provide the second image data BIO_RGB stored in the memory unit to the display device 1250 at the second frame. In other exemplary embodiments, the GPU 1220 may generate the second image data BIO_RGB by modulating the first image data RGB, and may provide the generated second image data BIO_RGB to the display device 1250 at the second frame.

The display device 1250 may receive the first image data RGB for the original image, and may display the original image based on the first image data RGB at the first frame. At the second frame, the display device 1250 may receive the second image data BIO_RGB for the bioeffect image, and may display the bioeffect image based on the second image data BIO_RGB at the second frame. According to exemplary embodiments, the bioeffect image may be a behavior inducing image, a biorhythm control image, a color weakness compensation image or a photo-therapy image, or may be a synthesized image where the original image and one of the behavior inducing image, the biorhythm control image, the color weakness compensation image and the photo-therapy image are synthesized.

Figure 24:
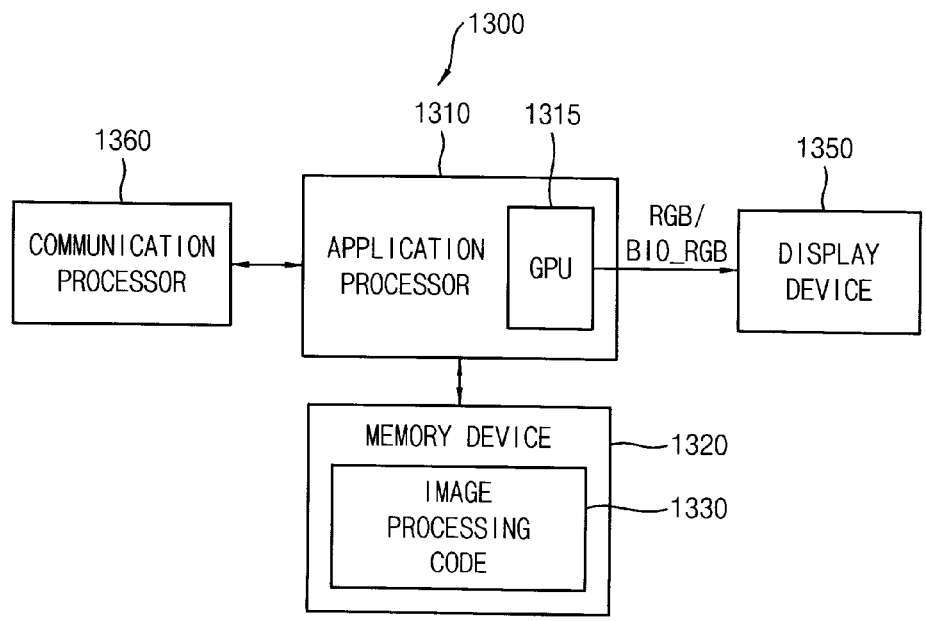
FIG. 24 is a block diagram illustrating another exemplary embodiment of a mobile device including an application processor performing a bioeffect image providing function by executing an image processing code, in accordance with exemplary embodiments.

FIG. 24 is a block diagram illustrating another exemplary embodiment of a mobile device including an application processor performing a bioeffect image providing function by executing an image processing code, in accordance with the invention.

Referring to FIG. 24, an exemplary embodiment of a mobile device 1300 includes an application processor 1310, a memory device 1320, a communication processor 1360 and a display device 1350. The application processor 1310 may include a GPU 1315 that controls the display device 1350. The mobile device 1300 shown in FIG. 24 may have a similar configuration to a mobile device 100 shown in FIG. 1, except that the bioeffect image providing function is performed based on an image processing code 1330 stored in the memory device 1320.

The memory device 1320 may store the image processing code 1330 for the bioeffect image providing function, and the application processor 1310 may execute the image processing code 1330 to selectively provide first image data RGB for an original image or second image data BIO_RGB for a bioeffect image to the display device 1350. In some exemplary embodiments, the memory device 1320 may further store the second image data BIO_RGB for the bioeffect image, and the image processing code 1330 executed by the application processor 1310 may provide the second image data BIO_RGB stored in the memory device 1320 instead of the first image data RGB at a predetermined frame. In other exemplary embodiments, the image processing code 1330 executed by the application processor 1310 may generate the second image data BIO_RGB by modulating the first image data RGB, and may provide the generated second image data BIO_RGB to the display device 1250 at the predetermined frame.

The display device 1350 may receive the first image data RGB or the second image data BIO_RGB, and may display the original image or the bioeffect image based on the first image data RGB or the second image data BIO_RGB.

As shown in FIG. 24 and described above, in an exemplary, the image processing code 1330 is stored in the memory device 1320 that is a main memory of the mobile device 1300, but not being limited thereto. In some alternative exemplary embodiments, the image processing code 1330 may be stored in an internal memory formed on a display panel 230 of the display device 1350. In one exemplary embodiment, for example, the display device 1350 may include a display panel 230, and an internal memory provided on the display panel 230, where the image processing code 1330 is stored in the internal memory. The image processing code 1330 stored in the internal memory may be executed by the application processor 1310 or another processor to selectively provide the first image data RGB or the second image data BIO_RGB to the display panel 230.

Figure 25:
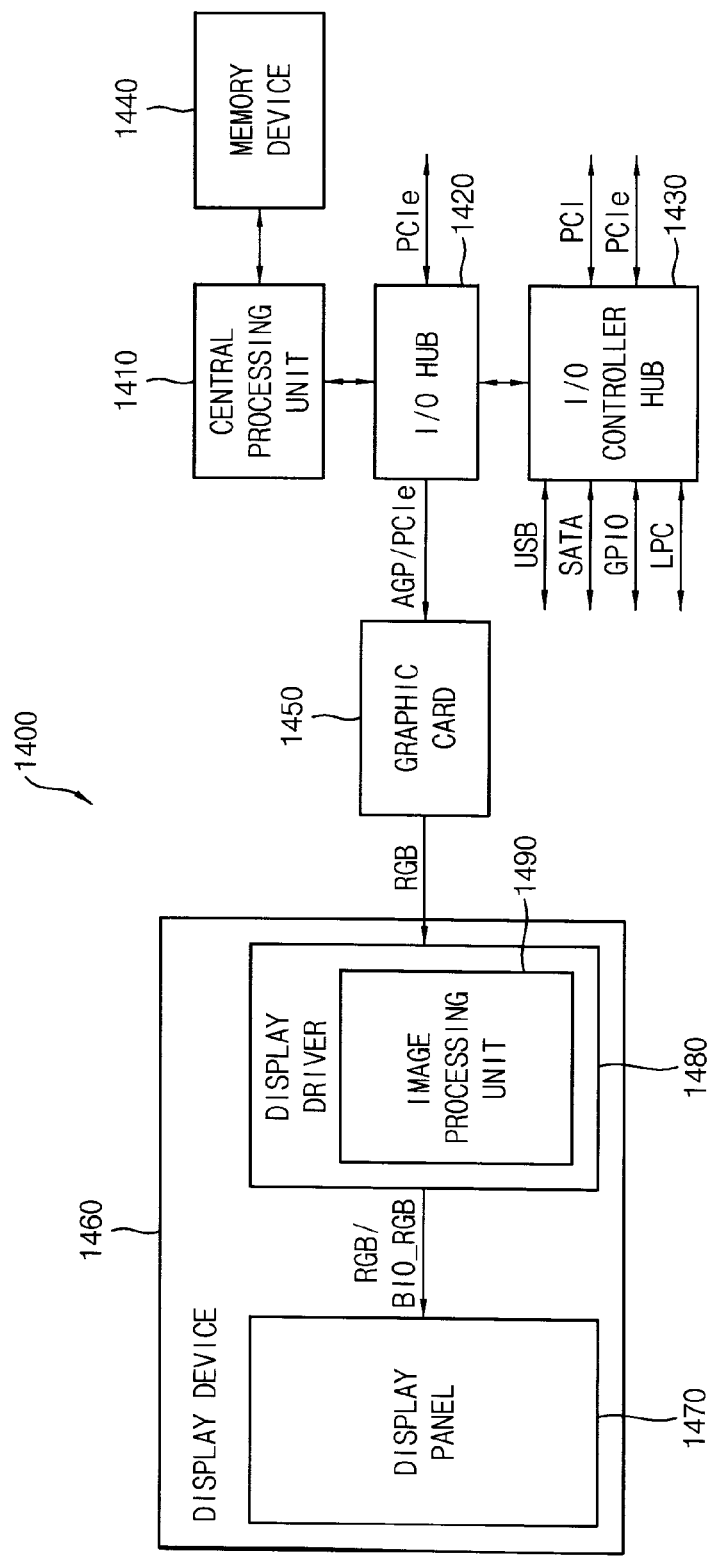
FIG. 25 is a block diagram illustrating an exemplary embodiment of a computing device including a display driver having a bioeffect image providing function, in accordance with the invention.

FIG. 25 is a block diagram illustrating an exemplary embodiment of a computing device including a display driver having a bioeffect image providing function, in accordance with the invention.

Referring to FIG. 25, an exemplary embodiment of a computing device 1400 includes a central processing unit ("CPU") 1410, an input/output hub 1420, an input/output controller hub 1430, at least one memory device 1440, a graphic card 1450 and a display device 1460. In some exemplary embodiments, the computing device 1400 may be any computing device, such as a personal computer ("PC"), a server computer, a workstation, a tablet computer, a laptop computer, a mobile phone, a smart phone, a PDA, a PMP, a digital camera, a digital television, a set-top box, a music player, a portable game console, a navigation device, etc. In such an embodiment, the computing device 1400 may include an image processing unit 1490 in a display driver 1480 of the display device 1460, as described above with reference to FIG. 1.

The CPU 1410 may control an operation of the computing device 1400. The CPU 1410 may perform specific calculations or tasks to control the operation of the computing device 1400. The CPU 1410 may include a processor core. In one exemplary embodiment, for example, the CPU 1410 may be a single core processor or a multi-core processor, such as a dual-core processor, a quad-core processor, a hexa-core processor, etc. In an exemplary embodiment, the computing system 1400 may include a single CPU 1410, as shown in FIG. 25, but not being limited thereto. In some alternative exemplary embodiments, the computing system 1400 may include a plurality of CPUs.

The CPU 1410 may include a memory controller that controls an operation of the memory device 1440. The memory device 1440 may be coupled to the CPU 1410, and may operate as a main memory of the computing device 1400. The memory controller included in the CPU 1410 may be referred to as an integrated memory controller ("IMC"). In other exemplary embodiments, the memory controller may be included in the input/output hub 1420. The input/output hub 1420 including the memory controller may be referred to as a memory controller hub ("MCH").

The input/output hub 1420 may manage data transfer between the CPU 1410 and devices, such as the graphic card 1450. The input/output hub 120 may be coupled to the CPU 1410 via one of various interfaces including a front side bus ("FSB"), a system bus, a HyperTransport, a lightning data transport ("LDT"), a QuickPath interconnect ("QPI"), and a common system interface ("CSI"). In an exemplary, as shown in FIG. 25, the computing system 1400 includes one input/output hub 1420, but not being limited thereto. In some alternative exemplary embodiments, the computing system 1400 may include a plurality of input/output hubs. The input/output hub 1420 may provide various interfaces with the devices including an accelerated graphics port ("AGP") interface, a peripheral component interface-express ("PCIe"), and a communications streaming architecture ("CSA") interface.

The input/output controller hub 1430 may perform data buffering and interface arbitration to efficiently operate various system interfaces. The input/output controller hub 1430 may be coupled to the input/output hub 1420 via various interfaces including a direct media interface ("DMI"), a hub interface, an enterprise Southbridge interface ("ESI"), and PCIe. The input/output controller hub 1430 may provide various interfaces with peripheral devices. In one exemplary embodiment, for example, the input/output controller hub 1430 may provide a universal serial bus ("USB") port, a serial advanced technology attachment ("SATA") port, a general purpose input/output ("GPIO"), a low pin count ("LPC") bus, a PCI, and a PCIe.

In some exemplary embodiments, the CPU 1410, the input/output hub 1420 and the input/output controller hub 1430 may be implemented as separate chipsets or separate integrated circuits. In other exemplary embodiments, at least two of the CPU 1410, the input/output hub 1420 and the input/output controller hub 1430 may be integrated as a single chipset.

The graphic card 1450 may be coupled to the input/output hub 1420 via the AGP or the PCIe. The graphic card 1450 may control the display device 1450 for displaying an image. The graphic card 1450 may include an internal processor and an internal memory to process the image. In some exemplary embodiments, an internal graphic device may be integrated into the input/output hub 1420. The internal graphic device may be referred to as an integrated graphics, and an input/output hub including the memory controller and the internal graphic device may be referred to as a graphics and memory controller hub ("GMCH").

The display device 1460 may include a display panel 1470 for displaying an image, and a display driver 1480 for driving the display panel 1470. According to exemplary embodiments, the display panel 1470 may be any display panel, such as an OLED panel, an LCD panel, a PDP, etc. The display driver 1480 may receive first image data RGB for an original image from the graphic card 1450, and may drive the display panel 1470 based on the first image data RGB to display the original image at a first frame. At a second frame, the display driver 1480 may drive the display panel 1470 based on second image data BIO_RGB for a bioeffect image instead of the first image data RGB to display the bioeffect image. According to exemplary embodiments, the bioeffect image may be a behavior inducing image, a biorhythm control image, a color weakness compensation image or a photo-therapy image, or may be a synthesized image where the original image and one of the behavior inducing image, the biorhythm control image, the color weakness compensation image and the photo-therapy image are synthesized.

Figure 26:
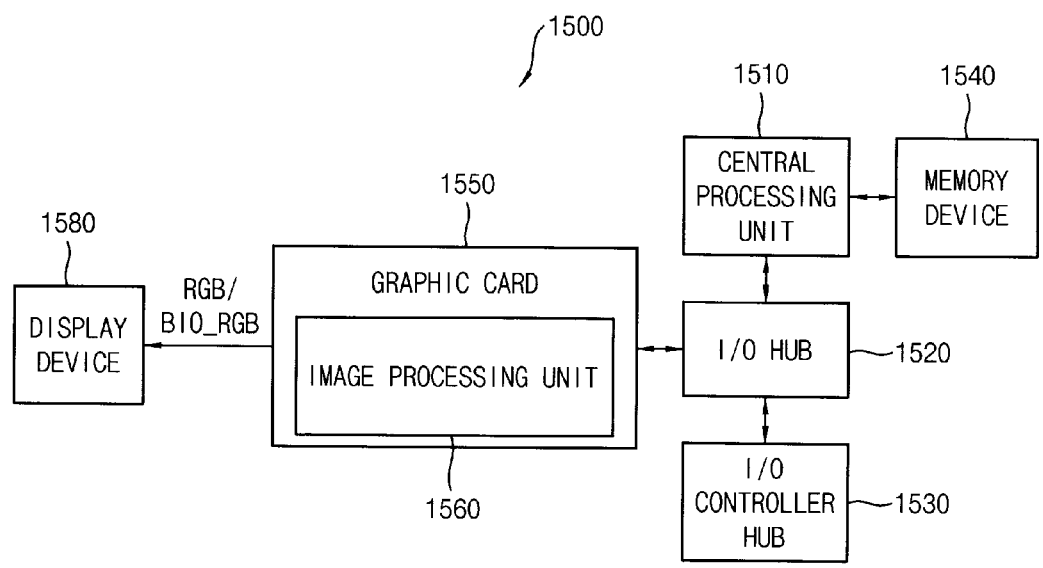
FIG. 26 is a block diagram illustrating another exemplary embodiment of a computing device including a graphic card having a bioeffect image providing function, in accordance with the invention.

FIG. 26 is a block diagram illustrating another exemplary embodiment of a computing device including a graphic card having a bioeffect image providing function, in accordance with the invention.

Referring to FIG. 26, an exemplary embodiment of a computing device 1500 includes a CPU 1510, an input/output hub 1520, an input/output controller hub 1530, at least one memory device 1540, a graphic card 1550 and a display device 1580. The computing device 1500 shown in FIG. 26 may have a similar configuration to a computing device 1400 shown in FIG. 25, except that an image processing unit 1560 is included in the graphic card 1550.

The graphic card 1550 may be coupled between the CPU 1510 and the display device 1550 via the input/output hub 1520, and may control the display device 1550. The graphic card 1550 including the image processing unit 1560 may selectively provide first image data RGB for an original image or second image data BIO_RGB for a bioeffect image to the display device 1550 to display the original image or the bioeffect image. In some exemplary embodiments, the graphic card 1550 may further include a memory unit for storing the second image data BIO_RGB for the bioeffect image, and the image processing unit 1560 may provide the second image data BIO_RGB stored in the memory unit to the display device 1550. In other exemplary embodiments, the graphic card 1550 may generate the second image data BIO_RGB by modulating the first image data RGB, and may provide the generated second image data BIO_RGB to the display device 1550. According to exemplary embodiments, the bioeffect image may be a behavior inducing image, a biorhythm control image, a color weakness compensation image or a photo-therapy image, or may be a synthesized image where the original image and one of the behavior inducing image, the biorhythm control image, the color weakness compensation image and the photo-therapy image are synthesized.

Figure 27:
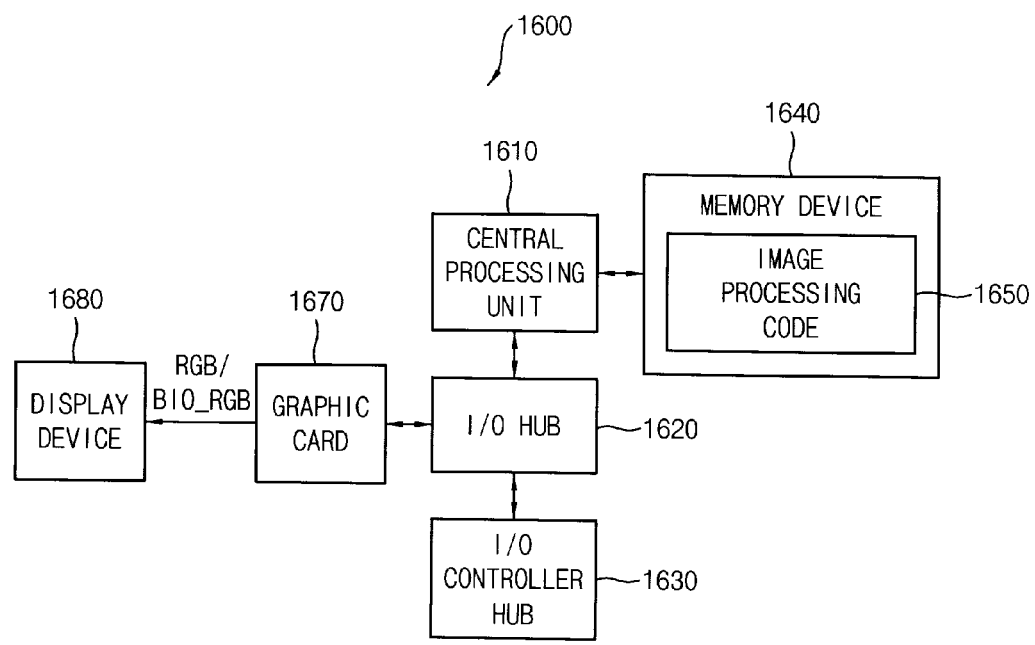
FIG. 27 is a block diagram illustrating another exemplary embodiment of a computing device including a central processing unit performing a bioeffect image providing function by executing an image processing code, in accordance with the invention.

FIG. 27 is a block diagram illustrating another exemplary embodiment of a computing device including a CPU performing a bioeffect image providing function by executing an image processing code, in accordance with the invention.

Referring to FIG. 27, an exemplary embodiment of a computing device 1600 includes a CPU 1610, an input/output hub 1620, an input/output controller hub 1630, a memory device 1640, a graphic card 1670 and a display device 1680. The memory device 1640 may store an image processing code 1650. The computing device 1600 shown in FIG. 27 may have a similar configuration to a computing device 1400 shown in FIG. 25, except that the bioeffect image providing function is performed based on the image processing code 1650 stored in the memory device 1640.

The memory device 1640 may store the image processing code 1650 for the bioeffect image providing function, and the CPU 1610 may execute the image processing code 1650 to selectively provide first image data RGB for an original image or second image data BIO_RGB for a bioeffect image to the display device 1680. In some exemplary embodiments, the memory device 1640 may further store the second image data BIO_RGB for the bioeffect image, and the image processing code 1650 executed by the CPU 1610 may provide the second image data BIO_RGB stored in the memory device 1640 instead of the first image data RGB at a predetermined frame. In other exemplary embodiments, the image processing code 1650 executed by the CPU 1610 may generate the second image data BIO_RGB by modulating the first image data RGB, and may provide the generated second image data BIO_RGB to the display device 1680 at the predetermined frame. According to exemplary embodiments, the image processing code 1650 may be included in an OS, or may be implemented as a separate executable program.

In an exemplary embodiment, as shown in FIG. 27, the image processing code 1650 is stored in the memory device 1640 that is a main memory of the computing device 1600, but not being limited thereto. In some alternative exemplary embodiments, the image processing code 1650 may be stored in an internal memory formed on a display panel 1470 of the display device 1680.

Figure 28:
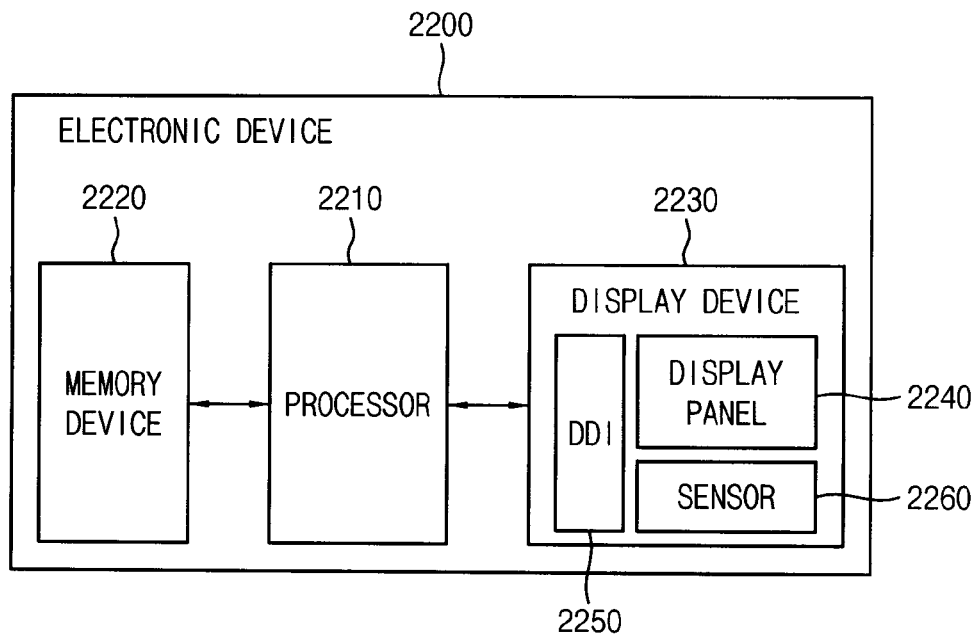
FIG. 28 is a block diagram illustrating an exemplary embodiment of an electronic device including a sensor, in accordance with the invention.
Figure 29A:
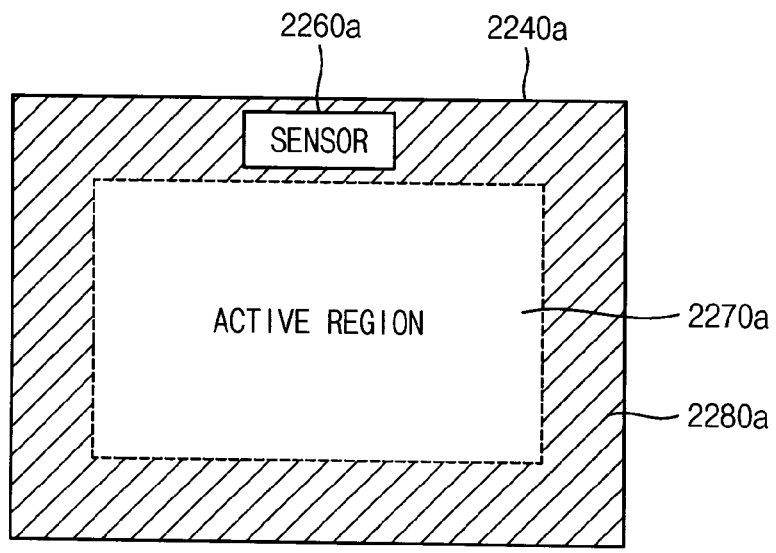
FIGS. 29A through 29C are block diagrams for describing exemplary embodiments of a sensor of the electronic device, in accordance with the invention.
Figure 29B:
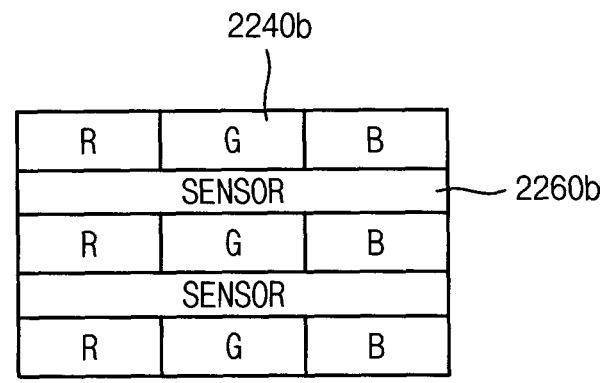
Figure 29C:
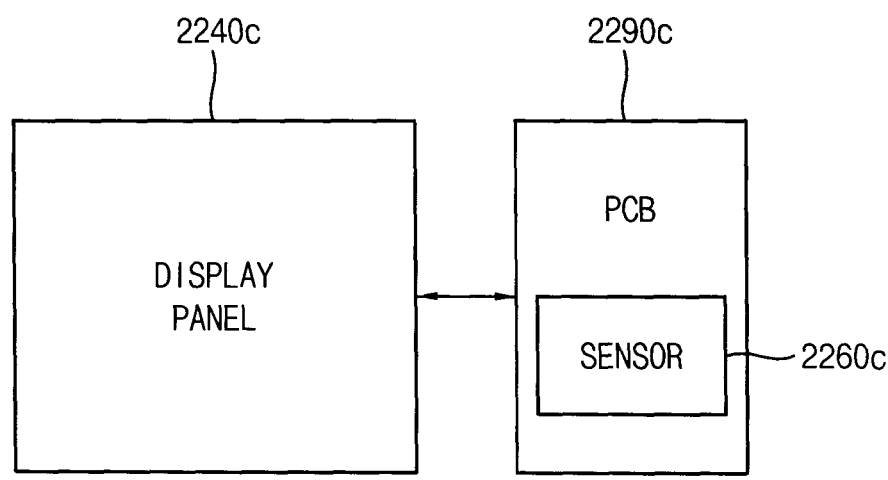

FIG. 28 is a block diagram illustrating an exemplary embodiment of an electronic device including a sensor, in accordance with the invention, and FIGS. 29A through 29C are block diagrams illustrating exemplary embodiments of a sensor of the electronic device, in accordance with the invention.

Referring to FIG. 28, an exemplary embodiment of an electronic device 2200 may include a processor 2210, a memory device 2220 and a display device 2230. The electronic device 2200 may be a mobile device or a computing device. The display device 2230 may include a display panel 2240, a display driver 2250 and a sensor 2260. In such an embodiment, the display device 2230 may further include the sensor 2260.

The sensor 2260 may sense light. In some exemplary embodiments, the sensor 2260 may sense incident light or ambient light. In one exemplary embodiment, for example, the sensor 2260 may be a photo sensor that measures chromaticity of the incident light or the ambient light. The display device 2230 may provide a biorhythm control image based on the measured chromaticity of the incident light (or the ambient light). In one exemplary embodiment, for example, when the chromaticity of the incident light is close to a yellow color, the display driver 2250 may generate the biorhythm control image having reduced blue luminance by decreasing blue sub-pixel data from image data for an original image. The biorhythm control image having reduced blue luminance may prevent suppression of melatonin secretion of a user. Although the blue luminance is reduced, the user may not perceive the reduction of the blue luminance since the chromaticity of the incident light (or the ambient light) is close to the yellow color. In other exemplary embodiments, the sensor 2260 may detect an eye blink of a user. In one exemplary embodiment, for example, the sensor 2260 may be an image sensor that captures an image of the user. The display device 2230 may provide a behavior inducing image that induces the user to blink eyes based on the detected eye blink. In still other exemplary embodiments, the sensor 2260 may sense incident infrared light. The display device 2230 may initiate or terminate a bioeffect mode in response to the infrared light.

According to exemplary embodiments, the sensor 2260 may be disposed or provided at an active region or a peripheral region of the display panel 2240. In some exemplary embodiments, as illustrated in FIG. 29A, the sensor 2260a may be disposed at the peripheral region 2280a surrounding the active region 2270a of the display panel 2240a. In other exemplary embodiments, as illustrated in FIG. 29A, the sensor 2260b may be disposed at the active region of the display panel 2240b. In one exemplary embodiment, for example, the sensor 2260b may be disposed between sub-pixels or pixels. In still other exemplary embodiments, as illustrated in FIG. 29C, the sensor 2260c may be disposed on a printed circuit board 2290c coupled to the display panel 2240c.

Figure 30:
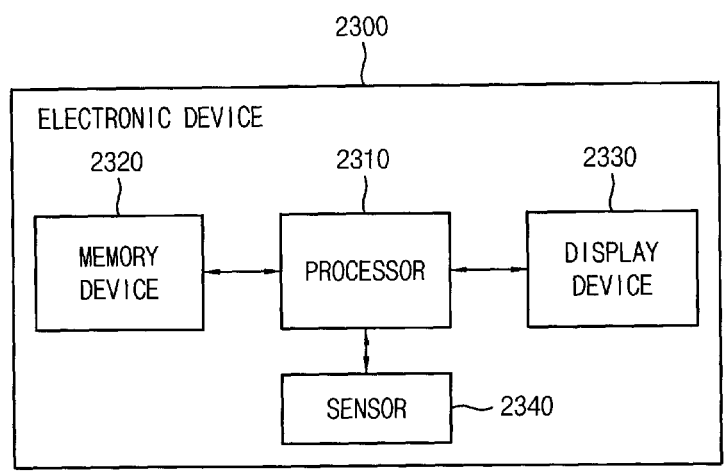
FIG. 30 is a block diagram illustrating another exemplary embodiment of an electronic device including a sensor, in accordance with the invention.

FIG. 30 is a block diagram illustrating another exemplary embodiment of an electronic device including a sensor, in accordance with the invention.

Referring to FIG. 30, an exemplary embodiment of an electronic device 2300 may include a processor 2310, a memory device 2320, a display device 2330 and a sensor 2340. The electronic device 2300 may be a mobile device or a computing device. The electronic device 2300 shown in FIG. 30 may have a similar configuration to an electronic device 2200 shown in FIG. 26, except that the sensor 2340 is disposed outside the display device 2230, and any repetitive detailed description thereof will be omitted.

Figure 31:
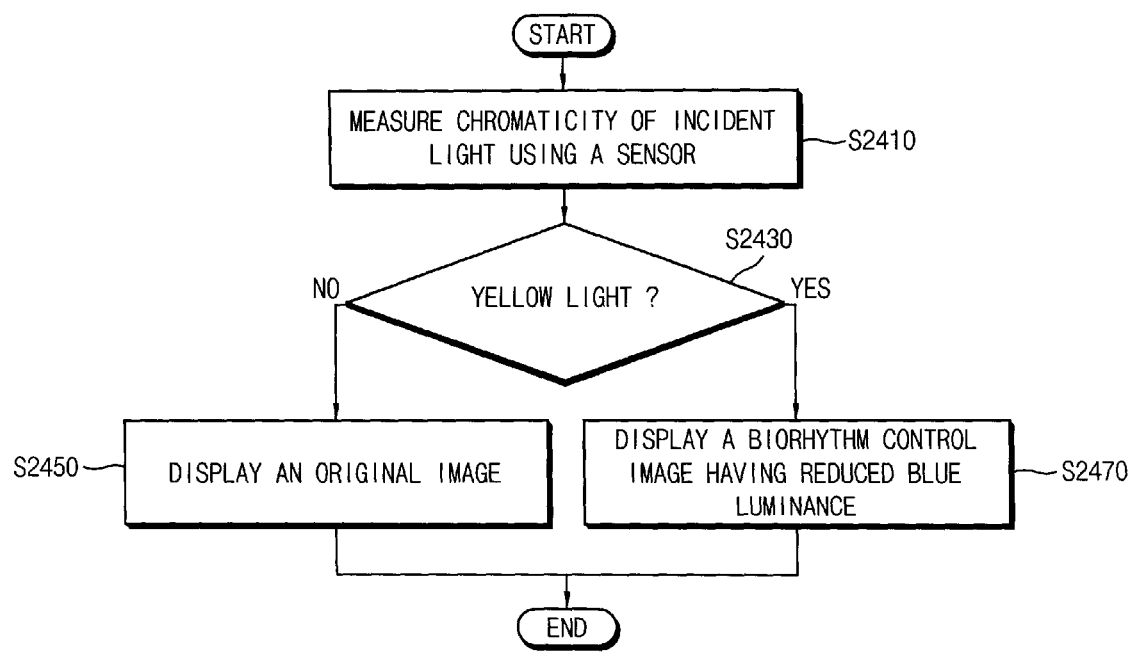
FIG. 31 is a flowchart illustrating an exemplary embodiment of a method of operating a display device to provide a biorhythm control image using a sensor, in accordance with the invention.

FIG. 31 is a flowchart illustrating an exemplary embodiment of a method of operating a display device to provide a biorhythm control image using a sensor, in accordance with the invention.

Referring to FIG. 31, an exemplary embodiment of an electronic device may measure chromaticity or color coordinate of incident light or ambient light using a sensor (S2410). In such an embodiment, when the measured chromaticity does not indicate a yellow color (S2430: NO), a display device may display an original image (S2450).

In such an embodiment, when the measured chromaticity indicates the yellow color (S2430: YES), the display device may display a biorhythm control image where blue luminance is reduced compared with the original image (S2470). The biorhythm control image having reduced blue luminance may effectively prevent suppression of melatonin secretion of a user. In such an embodiment, when the blue luminance is reduced, the user may not perceive the reduction of the blue luminance since the chromaticity of the incident light (or the ambient light) is the yellow color. Accordingly, the biorhythm control image that effectively prevents suppression of melatonin secretion may be provided to the user without causing any inconvenience of the user.

Figure 32:
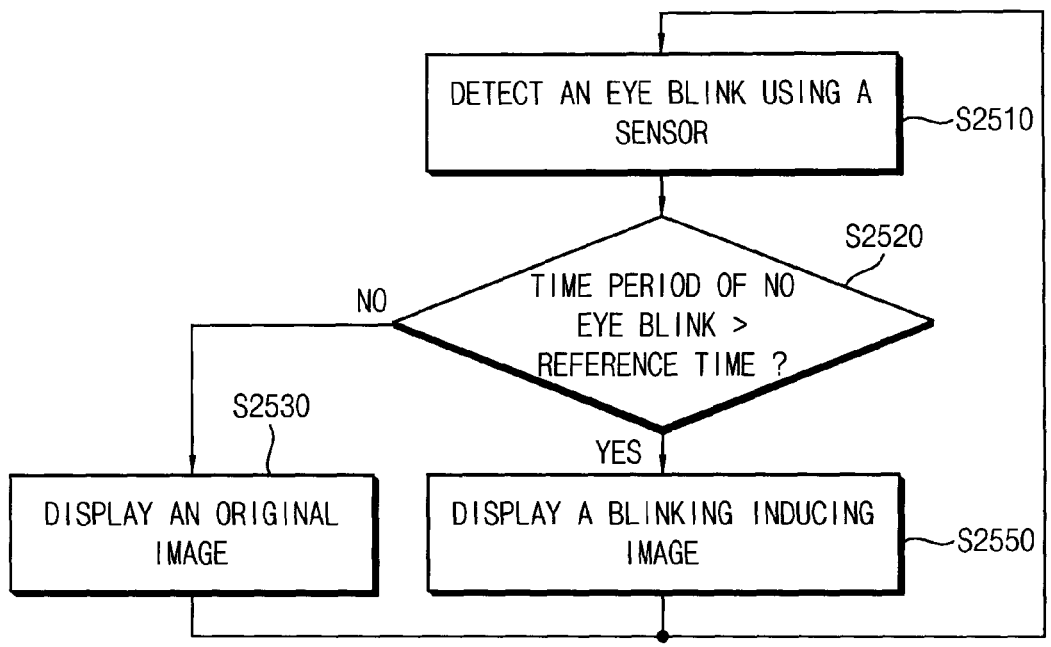
FIG. 32 is a flowchart illustrating an exemplary embodiment of a method of operating a display device to provide a blinking inducing image using a sensor, in accordance with the invention.

FIG. 32 is a flowchart illustrating an exemplary embodiment of a method of operating a display device to provide a blinking inducing image using a sensor, in accordance with the invention.

Referring to FIG. 32, an exemplary embodiment of an electronic device may detect an eye blink of a user using a sensor (S2510). According to exemplary embodiments, the sensor may be a complementary metal-oxide-semiconductor ("CMOS") image sensor or a charge-coupled device ("CCD") image sensor that captures an image of the user.

In such an embodiment, when a time period during which the user does not blink eyes is shorter than a predetermined reference time (S2520: NO), the electronic device may display an original image (S2530). In such an embodiment, when the time period during which the user does not blink eyes is longer than the predetermined reference time (S2520: YES), the electronic device may display a behavior inducing image that induces the user to blink the eyes, or a synthesized image where the original image and the behavior inducing image are synthesized (S2550). Accordingly, in such an embodiment, xerophthalmia of the user may be effectively prevented.

Figure 33:
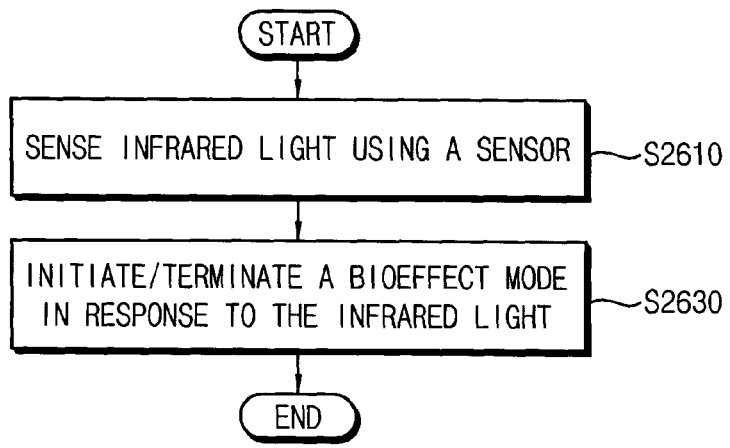
FIG. 33 is a flowchart illustrating an exemplary embodiment of a method of operating a display device that controls a bioeffect mode using a sensor, in accordance with the invention.

FIG. 33 is a flowchart illustrating an exemplary embodiment of a method of operating a display device that controls a bioeffect mode using a sensor, in accordance with the invention.

Referring to FIG. 33, an exemplary embodiment of an electronic device may sense infrared light using a sensor (S2610). In some exemplary embodiments, the sensor may be an infrared light sensor or an infrared radiation ("IR") sensor.

The electronic device may initiate or terminate a bioeffect mode in response to the sensed infrared light (S2630). According to exemplary embodiments, the electronic device may further adjust a period of a bioeffect image, a type of the bioeffect image or the like, in response to the sensed infrared light.

Figure 34:
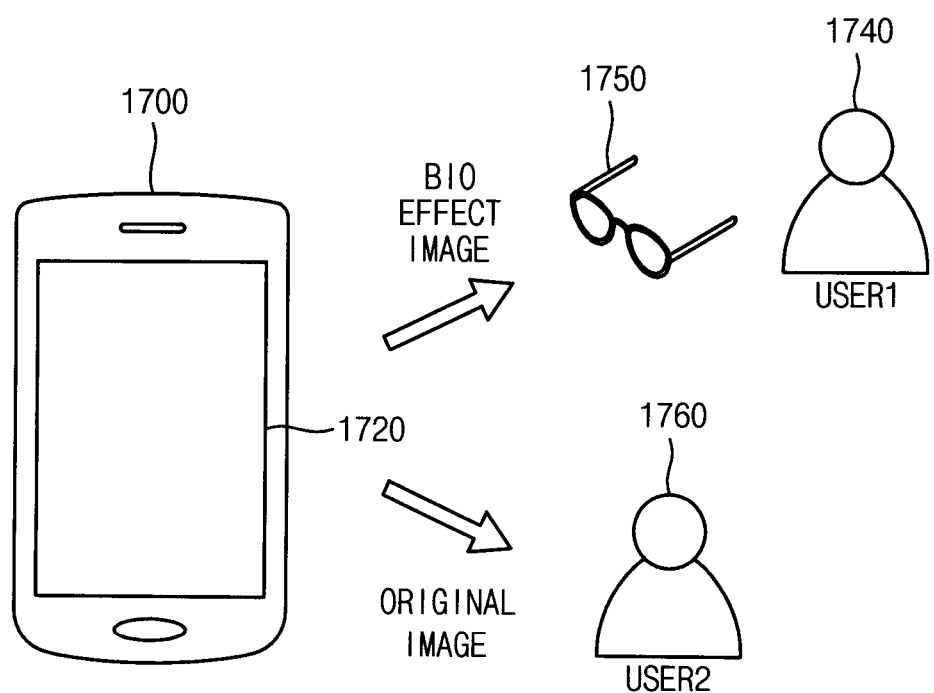
FIG. 34 is a diagram illustrating an exemplary embodiment of an electronic device that selectively provides a bioeffect image or an original image to users by using shutter glasses, in accordance with the invention.
Figure 35:
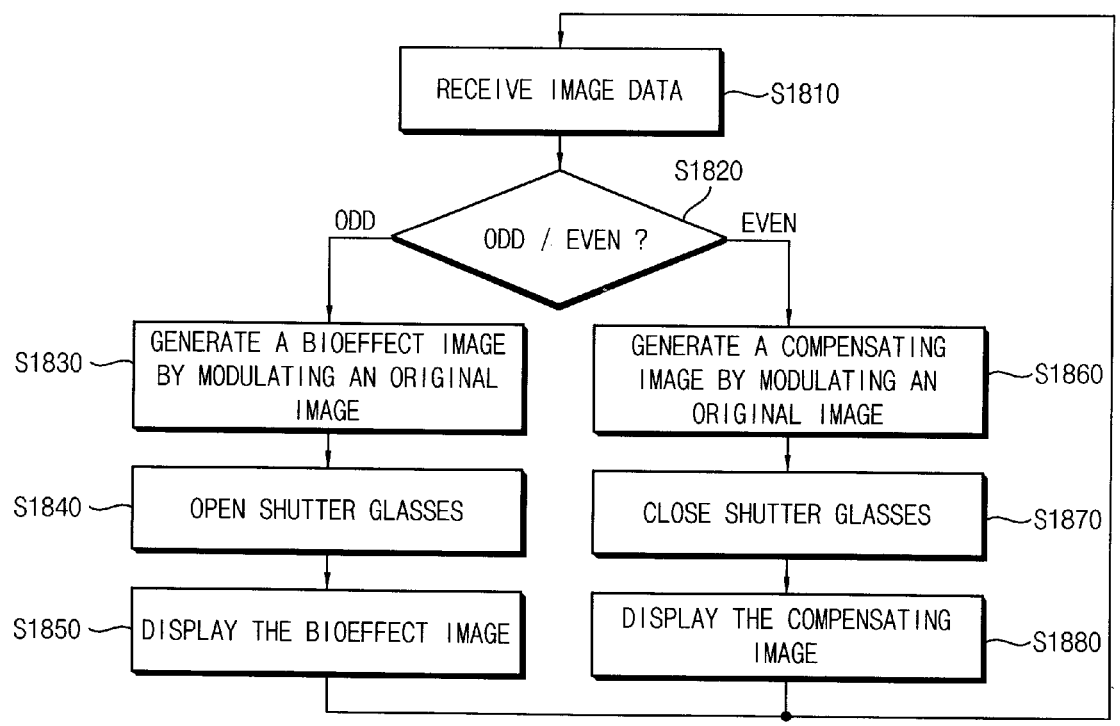
FIG. 35 is a flowchart illustrating an exemplary embodiment of a method of operating a display device to selectively provide a bioeffect image or an original image to users by using shutter glasses, in accordance with the invention.
Figure 36A:
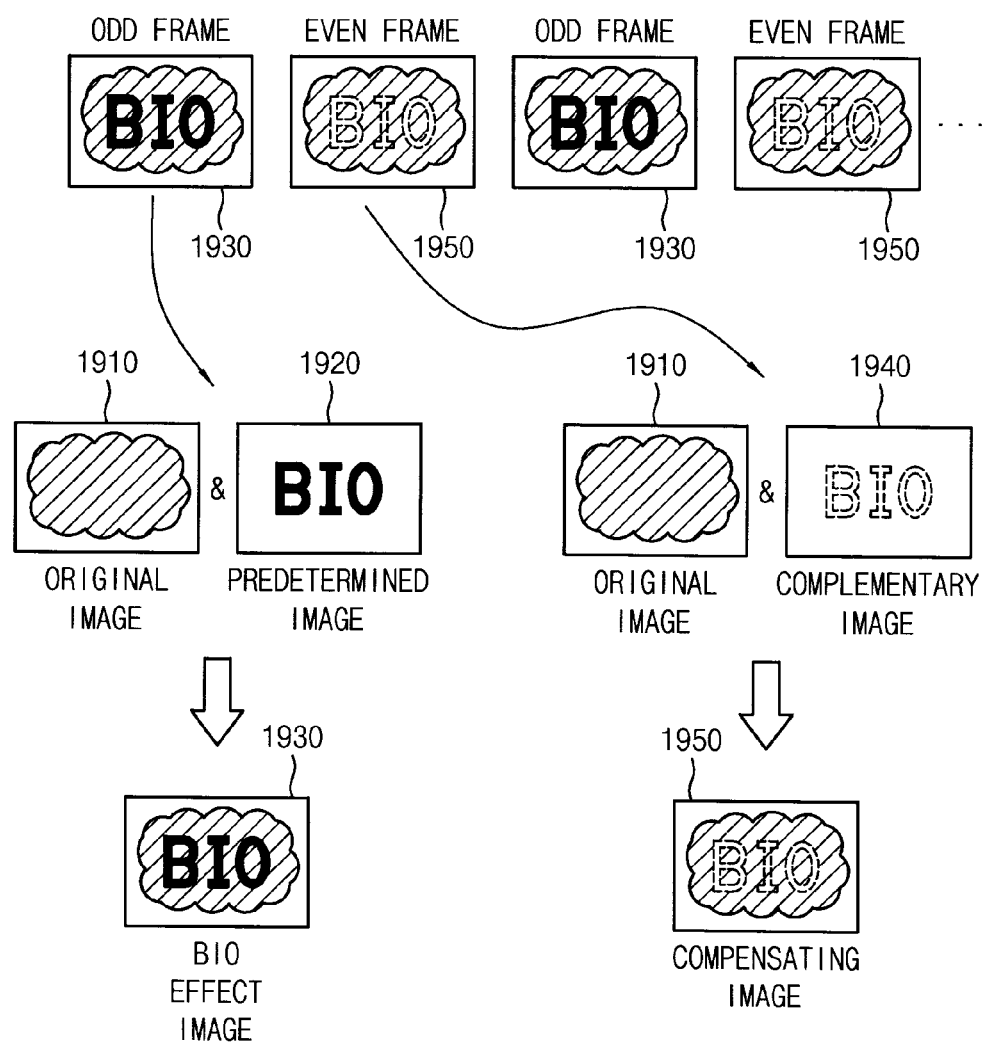
FIG. 36A is a diagram illustrating an exemplary embodiment of image frames displayed by the method of FIG. 35.
Figure 36B:
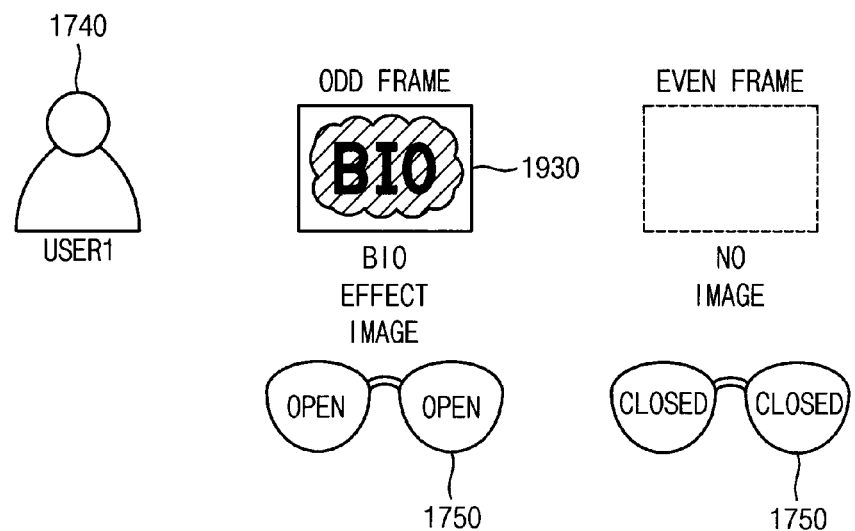
FIG. 36B is a diagram illustrating an exemplary embodiment of image frames provided to a first user by the method of FIG. 35.
Figure 36C:
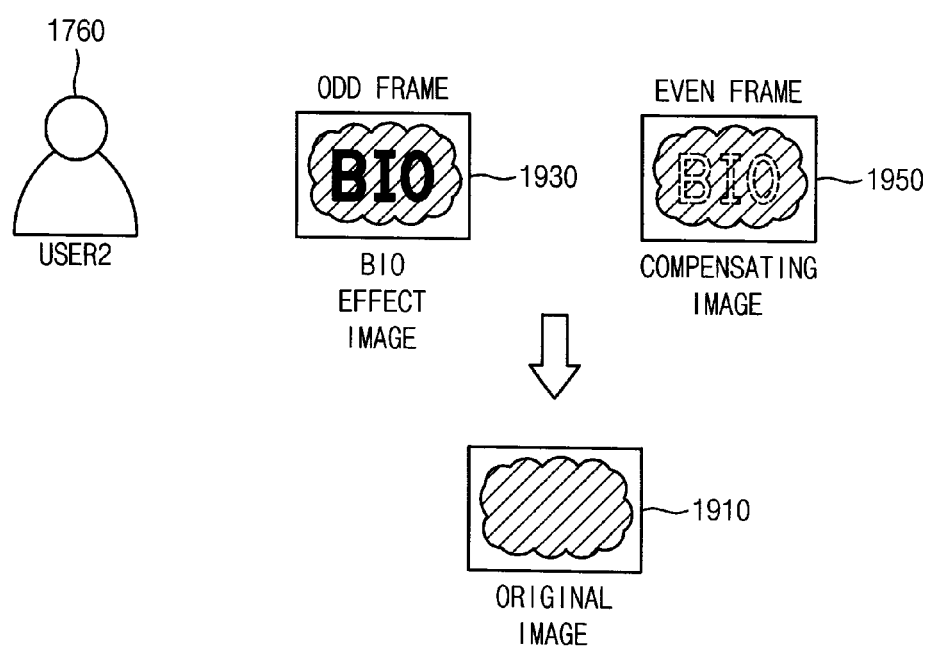
FIG. 36C is a diagram illustrating an exemplary embodiment of image frames provided to a second user by the method of FIG. 35.

FIG. 34 is a diagram illustrating an exemplary embodiment of an electronic device that selectively provides a bioeffect image or an original image to users by using shutter glasses, in accordance with the invention, FIG. 35 is a flowchart illustrating a method of operating a display device to selectively provide a bioeffect image or an original image to users by using shutter glasses, in accordance with the invention, FIG. 36A is a diagram illustrating an exemplary embodiment of image frames displayed by the method of FIG. 35, FIG. 36B is a diagram illustrating an exemplary embodiment of image frames provided to a first user by the method of FIG. 35, and FIG. 36C is a diagram illustrating an exemplary embodiment of image frames provided to a second user by the method of FIG. 35.

Referring to FIGS. 34 and 35, an exemplary embodiment of a display device 1720 in an electronic device 1700 may receive image data corresponding to a frame, e.g., every frame (S1810). In such an embodiment, the electronic device 1700 may be a mobile device or a computing device, for example.

In such an embodiment, when a current frame is an odd-numbered frame (S1820: ODD), the electronic device 1700 may generate a bioeffect image by modulating an original image (S1830). According to exemplary embodiments, the bioeffect image may be a behavior inducing image, a biorhythm control image, a color weakness compensation image or a photo-therapy image, or may be a synthesized image where the original image and one of the behavior inducing image, the biorhythm control image, the color weakness compensation image and the photo-therapy image are synthesized.

In some exemplary embodiments, as illustrated in FIG. 26A, the electronic device 1700 may generate the bioeffect image 1930 by synthesizing the original image 1910 and a predetermined image 1920 (e.g., the behavior inducing image, the biorhythm control image, the color weakness compensation image or the photo-therapy image). In other exemplary embodiments, the electronic device 1700 may generate the bioeffect image by adjusting at least one of red luminance, green luminance and blue luminance. According to exemplary embodiments, the bioeffect image may be generated by a display driver of the display device 1720, may be generated by a GPU or a graphic card, or may be generated by a predetermined code executed by a processor.

The electronic device 1700 may provide a control signal to shutter glasses 1750 via predetermined wired or wireless communication to control, e.g., open, the shutter glasses 1750 (S1840). The display device 1720 may display the bioeffect image 1930 where the original image 1910 and the predetermined image 1920 are synthesized (S1850). Accordingly, at the odd-numbered frame, the bioeffect image 1930 may be provided to a first user 1740 wearing the shutter glasses 1750 and a second user 1760 who does not wear the shutter glasses 1750.

In such an embodiment, when the current frame is an even-numbered frame (S1820: EVEN), the electronic device 1700 may generate a compensating image by modulating the original image (S1860). According to exemplary embodiments, the compensating image may be generated by the display driver, the GPU, the graphic card, the predetermined code executed by the processor, or the like.

In some exemplary embodiments, as illustrated in FIG. 36A, the compensating image 1950 may be generated by synthesizing the original image 1910 and a complementary image 1940 that is complementary to the predetermined image 1920. In other exemplary embodiments, the electronic device 1700 may generate the compensating image by adjusting the at least one of red luminance, green luminance and blue luminance inversely proportional to the adjustment of the bioeffect image.

Figure 37:
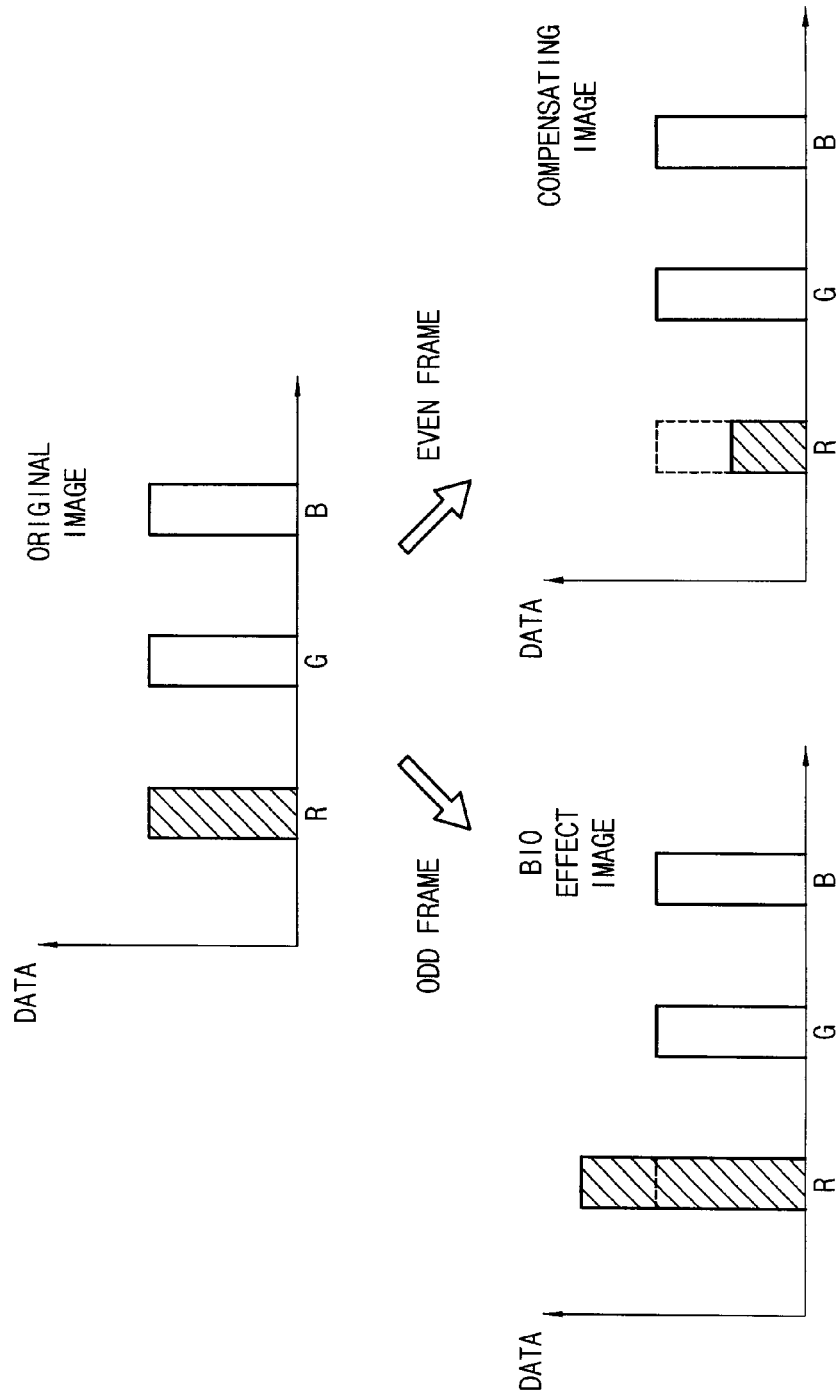
FIG. 37 is a diagram for describing an exemplary embodiment of a bioeffect image and a compensating image displayed by the method of FIG. 35.

In one exemplary embodiment, for example, as illustrated in FIG. 37, the bioeffect image 1930 at the odd-numbered frame may be generated by increasing red sub-pixel data of image data for the original image 1910, for example, to provide color weakness compensation, anti-inflammatory therapy, pimple therapy, wrinkle therapy, etc. In such an embodiment, the compensating image 1950 at the even-numbered frame may be generated by decreasing the red sub-pixel data of the image data for the original image 1910 such that the increase of the red sub-pixel data at the bioeffect image 1930 is compensated. Thus, in such an embodiment, where the compensating image 1950 is generated by increasing the decreased data of the bioeffect image 1930 or by decreasing the increased data of the bioeffect image 1930, and the bioeffect image 1930 and the compensating image 1950 are alternately provided to a user, the user may perceive the original image 1910 based on the alternately provided bioeffect and compensating images 1930 and 1950.

The electronic device 1700 may provide a control signal to shutter glasses 1750 via predetermined wired or wireless communication to close the shutter glasses 1750 (S1870). The display device 1720 may display the compensating image 1950 where the original image 1910 and the complementary image 1940 are synthesized (S1880). Accordingly, at the odd-numbered frame, the compensating image 1950 may be provided only to the second user 1760 that does not wear the shutter glasses 1750.

Accordingly, as illustrated in FIG. 36B, the first user 1740 wearing the shutter glasses 1750 may be provided with the bioeffect image 1930 at the odd-numbered frame, and may not be provided with any image at the even-numbered frame. In one exemplary embodiment, for example, the bioeffect image 1930 may be a color weakness image, or a synthesized image where the original image and the color weakness image are synthesized, and the first user 1740 having color weakness may be provided only with the color weakness image by wearing the shutter glasses 1750.

Further, as illustrated in FIG. 36C, the second user 1760 that does not wear the shutter glasses 1750 may be provided with the bioeffect image 1930 at the odd-numbered frame, and may be provided with the compensating image 1950 at the even-numbered frame. Accordingly, in such an embodiment, the bioeffect image 1930 and the compensating image 1950 are alternately provided to the second user 1760, such that the second user 1760 may substantially perceive the original image 1910.

In other exemplary embodiments, the electronic device 1700 may not employ the shutter glasses 1750, and may display at least one bioeffect image 1930, at least one compensating image 1950 and a plurality of original images 1910 with a fixed or variable period. In such an embodiment, although the electronic device 1700 provides the bioeffect image 1930 to a user, the user may substantially perceive the original image 1910.

Figure 38:
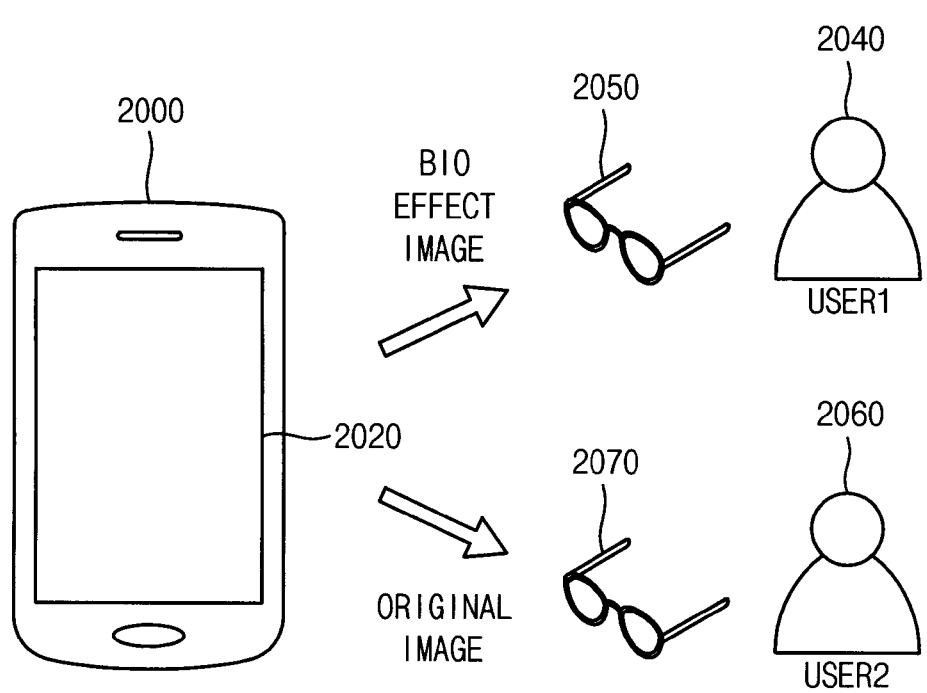
FIG. 38 is a diagram illustrating another exemplary embodiment of an electronic device that selectively provides a bioeffect image or an original image to users by using shutter glasses, in accordance with the invention.
Figure 39:
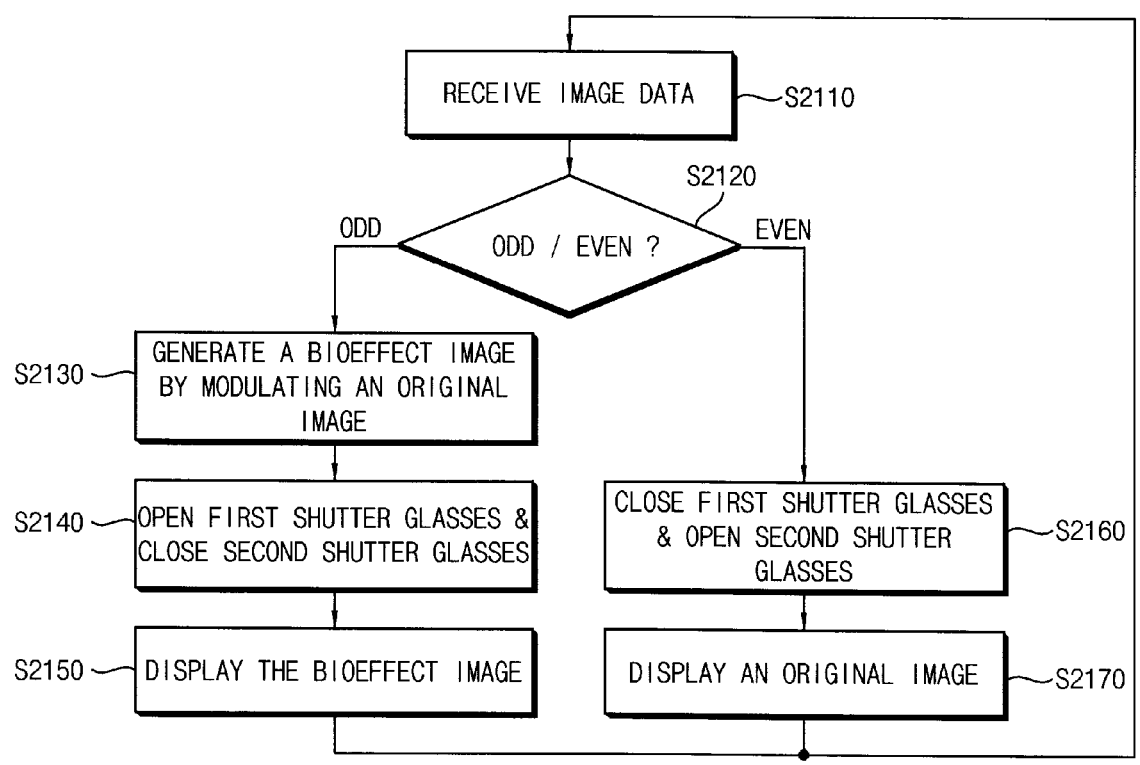
FIG. 39 is a flowchart illustrating another exemplary embodiment of a method of operating a display device to selectively provide a bioeffect image or an original image to users by using shutter glasses, in accordance with the invention.
Figure 40:
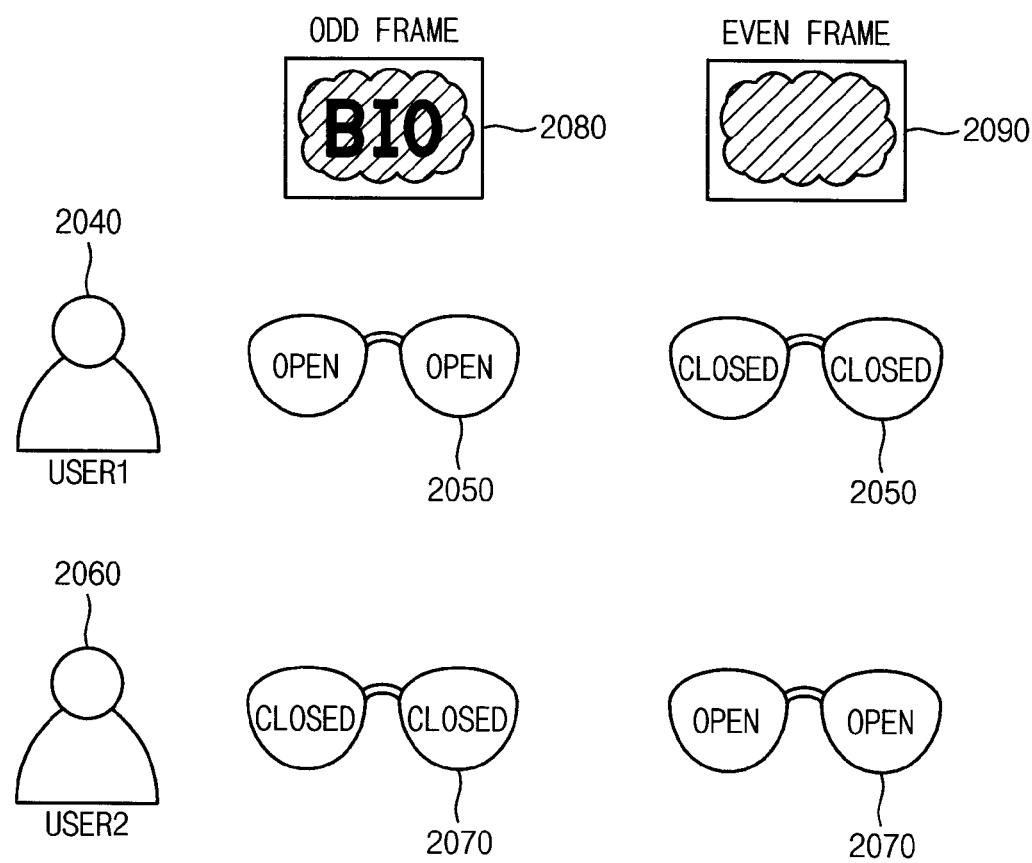
FIG. 40 is a diagram illustrating an exemplary embodiment of image frames provided to first and second users by the method of FIG. 39.

FIG. 38 is a diagram illustrating another exemplary embodiment of an electronic device that selectively provides a bioeffect image or an original image to users by using shutter glasses, in accordance with the invention, FIG. 39 is a flowchart illustrating another exemplary embodiment of a method of operating a display device to selectively provide a bioeffect image or an original image to users by using shutter glasses, in accordance with the invention, and FIG. 40 is a diagram illustrating an exemplary embodiment of image frames provided to first and second users by the method of FIG. 39.

Referring to FIGS. 38, 38 and 40, an exemplary embodiment of a display device 2020 included in an electronic device 2000 may receive image data corresponding to a frame (S2110). In such an embodiment, the electronic device 2000 may be a mobile device or a computing device, for example.

In such an embodiment, when a current frame is an odd-numbered frame (S2120: ODD), the electronic device 2000 may generate and/or display a bioeffect image 2080 as illustrated in FIG. 40 (S2130). According to exemplary embodiments, the bioeffect image 2080 may be a behavior inducing image, a biorhythm control image, a color weakness compensation image or a photo-therapy image, or may be a synthesized image where the original image and one of the behavior inducing image, the biorhythm control image, the color weakness compensation image and the phototherapy image are synthesized. According to exemplary embodiments, the bioeffect image 2080 may be generated by a display driver, a GPU, a graphic card, a predetermined code executed by a processor, or the like. In such an embodiment, the electronic device 2000 may control first shutter glasses 2050 and second shutter glasses 2070, e.g., open the first shutter glasses 2050 and close the second shutter glasses 2070, via predetermined wired or wireless communication (S2140). The display device 2020 may display the bioeffect image 2080 (S2150). Accordingly, at the odd-numbered frame, the bioeffect image 2080 may be provided to a first user 2040 wearing the first shutter glasses 2050, and may not be provided to a second user 2060 wearing the second shutter glasses 2070.

In such an embodiment, when the current frame is an even-numbered frame (S2120: EVEN), the electronic device 2000 may not perform a modulation operation for an original image 2090. In such an embodiment, the electronic device 2000 may close first shutter glasses 2050 and open second shutter glasses 2070 via predetermined wired or wireless communication (S2160). The display device 2020 may display the original image 2090 (S2170). Accordingly, at the even-numbered frame, the original image 2090 may not be provided to the first user 2040 wearing the first shutter glasses 2050, and may be provided to the second user 2060 wearing the second shutter glasses 2070. Accordingly, only the bioeffect image 2080 may be provided to the first user 2040 wearing the first shutter glasses 2050, and only the original image 2090 may be provided to the second user 2060 wearing the second shutter glasses 2070.

Exemplary embodiments of the invention as described herein may be applied to any mobile device or any computing device, for example, a cellular phone, a smart phone, a tablet computer, a PDA, a PMP, a digital camera, a music player, a portable game console, a navigation system, a video phone, a PC, a server computer, a workstation, a tablet computer, a laptop computer, etc.

The foregoing is illustrative of exemplary embodiments, and is not to be construed as limiting thereof. Although some exemplary embodiments have been described, those skilled in the art will readily appreciate that many modifications are possible in the exemplary embodiments without materially departing from the novel teachings and advantages of exemplary embodiments. Accordingly, all such modifications are intended to be included within the scope of exemplary embodiments as defined in the claims. Therefore, it is to be understood that the foregoing is illustrative of exemplary embodiments and is not to be construed as limited to the specific embodiments disclosed, and that modifications to the disclosed exemplary embodiments, as well as other exemplary embodiments, are intended to be included within the scope of the appended claims. The invention is defined by the following claims, with equivalents of the claims to be included therein.

What is claimed is:

1. An electronic device comprising:
a processor which controls an operation of the electronic device;
a memory device coupled to the processor, wherein the memory device operates as a main memory of the electronic device; and
a display device coupled to the processor, wherein the display device displays an original image based on first image data for the original image at a first frame, displays a bioeffect image, which is different from the original image, based on second image data for the bioeffect image at a second frame, and displays a compensating image based on third image data for the compensating image at a third frame,
wherein the display device comprises:
a display panel; and
a display driver comprising:
an image processor which receives the first image data, outputs the first image data at the first frame, generates the second image data by increasing a value of at least one of red sub-pixel data, green sub-pixel data and blue sub-pixel data included in the first image data from the first image data at the second frame, and generates the third image data for the compensating image by decreasing a value of the at least one of the red sub-pixel data, the green sub-pixel data and the blue sub-pixel data from the first image data at the third frame adjacent to the second frame; and a driver which drives the display panel based on the first image data output from the image processor at the first frame, drives the display panel based on the second image data to display, as the bioeffect image, a photo-therapy image where a value of at least one of red luminance, green luminance and blue luminance is increased from a value of the original image at the second frame, and drives the display panel based on the third image data to display the compensating image where the value of the at least one of the red luminance, the green luminance and the blue luminance is decreased from the value of the original image at the third frame, and wherein the original image is perceived based on the photo-therapy image displayed at the second frame and the compensating image displayed at the third frame.

2. The electronic device of claim 1, wherein the processor comprises a graphic processor which controls the display device.

3. The electronic device of claim 1, further comprising:
a graphic card coupled between the processor and the display device, wherein the graphic card controls the display device.

4. The electronic device of claim 1, wherein the display device further comprises:
an internal memory disposed on the display panel, and which stores information about a modulation operation and an image processing code, and
wherein the image processing code stored in the internal memory of the display device is executed by the image processor to provide the display panel with the first image data at the first frame, to generate the second image data by modulating the first image data based on the information about the modulation operation and to provide the display panel with the generated second image data at the second frame.

5. The electronic device of claim 1, wherein
the display driver further comprises a memory unit which stores information about a modulation operation comprising image data for a behavior inducing image,
the image processor generates fourth image data by synthesizing the first image data and the image data for the behavior inducing image at a fourth frame, and
the driver drives the display panel based on the fourth image data where the first image data and the image data for the behavior inducing image are synthesized to display, as the bioeffect image, an image where the original image and the behavior inducing image are synthesized at the fourth frame.

6. The electronic device of claim 5, wherein the image, in which the original image and the behavior inducing image are synthesized, is displayed for a predetermined duration shorter than a duration perceptible by a user.

7. The electronic device of claim 1, wherein
the image processor generates fourth image data by decreasing a value of the blue sub-pixel data from the first image data at a fourth frame, and
the driver drives the display panel based on the fourth image data where the value of the blue sub-pixel data is decreased to display, as the bioeffect image, a biorhythm control image where the blue luminance is decreased from the value of the original image to prevent suppression of melatonin secretion of a user at the fourth frame.

8. The electronic device of claim 1, wherein
the image processor generates fourth image data by increasing a value of the blue sub-pixel data from the first image data at a fourth frame, and
the driver drives the display panel based on the fourth image data where the value of the blue sub-pixel data is increased to display, as the bioeffect image, a biorhythm control image where the blue luminance is increased from the value of the original image to suppress melatonin secretion of a user at the fourth frame.

9. The electronic device of claim 1, wherein
the image processor generates fourth image data by increasing a value of the red sub-pixel data from the first image data at a fourth frame, and
the driver drives the display panel based on the second image data where the value of the red sub-pixel data is increased to display, as the bioeffect image, a color weakness compensation image where the value of the red luminance is increased from the value of the original image to increase a visibility of a user having red color weakness at the fourth frame.

10. The electronic device of claim 1, wherein
the image processor generates fourth image data by increasing a value of the green sub-pixel data from the first image data at a fourth frame, and
the driver drives the display panel based on the second image data where the value of the green sub-pixel data is increased to display, as the bioeffect image, a color weakness compensation image where the value of the green luminance is increased from the value of the original image to increase a visibility of a user having green color weakness at the fourth frame.

11. The electronic device of claim 1, wherein the second image data is generated by modulating the first image data based on information about a modulation operation stored therein to display the bioeffect image, and
wherein the information about the modulation operation comprises positions of modulated data in a frame, values of data to be added or multiplied, indication of which one of the red, green and blue sub-pixel data are modulated, or coefficients of the modulation operation.

12. An electronic device comprising:
a processor which controls an operation of the electronic device;
a memory device coupled to the processor, wherein the memory device operates as a main memory of the electronic device;
a display device coupled to the processor, wherein the display device displays an original image based on first image data for the original image at a first frame, and displays a bioeffect image based on second image data for the bioeffect image at a second frame; and
a sensor which senses incident light,
wherein the sensor measures chromaticity of the incident light, and
wherein, when the measured chromaticity of the incident light indicates a yellow color, the display device displays, as the bioeffect image, a biorhythm control image which prevents suppression of melatonin secretion of a user.

13. The electronic device of claim 12, wherein
the sensor detects an eye blink of a user, and
if the user does not blink during a predetermined time, the display device displays a blinking inducing image as the bioeffect image.

14. The electronic device of claim 12, wherein
the sensor senses infrared light as the incident light, and
the electronic device initiates or terminates a bioeffect mode in response to the infrared light.

15. The electronic device of claim 12, wherein the sensor is disposed in at least one of an active region of a display panel included in the display device, a peripheral region of the display panel, a printed circuit board coupled to the display panel, and an outside of the display device.

\* \* \* \* \*